United States Patent [19]

Ottow et al.

[11] Patent Number: 5,446,178
[45] Date of Patent: Aug. 29, 1995

[54] PROCESS FOR PREPARING 19,11β-BRIDGED STEROIDS

[75] Inventors: Eckhard Ottow; Rudolf Wiechert; Gunter Neef; Sybille Beier; Walter Elger; David A. Henderson, all of Berlin, Germany

[73] Assignee: Schering Aktiengesellschaft, Berlin and Bergkamen, Germany

[21] Appl. No.: 111,315

[22] Filed: Aug. 2, 1993

Related U.S. Application Data

[60] Continuation of Ser. No. 793,880, Nov. 18, 1991, abandoned, which is a division of Ser. No. 283,632, Dec. 9, 1988, Pat. No. 5,095,129, which is a continuation-in-part of Ser. No. 415,359, Sep. 18, 1989, abandoned.

[30] Foreign Application Priority Data

Mar. 18, 1987 [DE] Germany ............... 37 08 942.0

[51] Int. Cl.⁶ .............................................. C07J 63/00
[52] U.S. Cl. ................................................. 552/510
[58] Field of Search ...................................... 552/510

[56] References Cited

U.S. PATENT DOCUMENTS

| | | | |
|---|---|---|---|
| 4,447,424 | 5/1984 | Teutsch et al. | 552/519 |
| 5,095,129 | 3/1992 | Otton et al. | 552/510 |
| 5,232,915 | 8/1993 | Otton et al. | 514/63 |

FOREIGN PATENT DOCUMENTS

| | | | |
|---|---|---|---|
| 188396 | 7/1987 | European Pat. Off. | 552/519 |
| 8303099 | 9/1983 | WIPO | 552/510 |
| 9014354 | 11/1990 | WIPO | 552/510 |

OTHER PUBLICATIONS

Grant and Hackh's Chemical Dictionary McGraw-Hill Book Company, New York, 1987 P. 14.
Hutchinson, et al. Tetrahedron Letters, 28(12) pp. 1313–1316, 1987.
Begley, et al. Tetrahedron Letters, 28(12), pp. 1317–1320, 1987.
Stork, et al. JACS, 1982, 104, 2321–2323.
Morrison and Boyd, 3rd Ed. Organic Chemistry (1979, Allyn and Bacon, Inc. Boston,) pp. 631 and 622.

*Primary Examiner*—Nicholas Rizzo
*Attorney, Agent, or Firm*—Millen, White, Zelane, & Branigan

[57] ABSTRACT

A process of cyclizing compounds of formula II

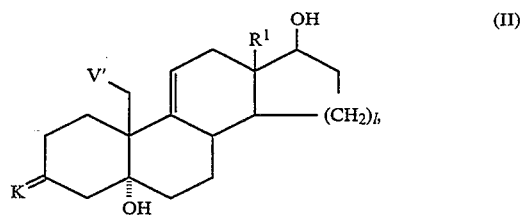

wherein K, V', R¹ and 1 are as herein defined, is described whereby a compound of formula IVa is produced

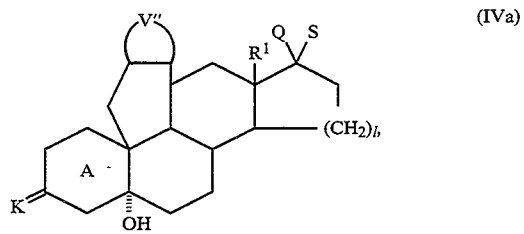

wherein K, V', R¹, Q, S and 1 are as herein defined. The compounds of formula IVa are useful intermediates in the production of compounds of formula I

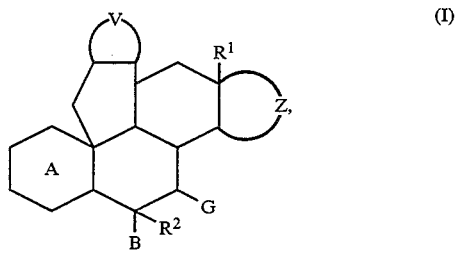

wherein ring A, B, G, V, Z, R¹ and R² are as herein defined.

35 Claims, 2 Drawing Sheets

PROCESS FOR PREPARING 19,11β-BRIDGED STEROIDS

This application is a continuation of application Ser. No. 07/793,880 (now abandoned), filed Nov. 18, 1991, which in turn is a division of application Ser. No. 07/283,632, filed Dec. 9, 1988 (now U.S. Pat. No. 5,095,129), which in turn is a continuation-in-part of Ser. No. 07/415,359, filed Sep. 18, 1989 (now abandoned).

CROSS-REFERENCE TO RELATED APPLICATION

SUMMARY OF THE INVENTION

The invention relates to the subject matter designated patent claims, i.e., new 19,11β-bridged steroids, methods for the manufacture of these compounds, pharmaceutical preparations containing these compounds, their use in the manufacture of pharmaceuticals as well as the new intermediate products required for this purpose.

The 19,11β-bridged steroids in accordance with the invention are described by general formula I

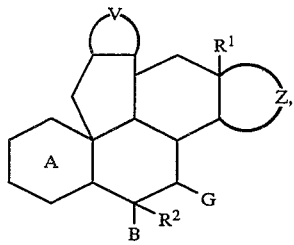

(I)

where
- $R^1$ stands for a methyl or ethyl radical,
- $R^2$ stands for a hydrogen, chlorine atom, a $C_1$-$C_4$-alkyl radical,
- B and G, which are the same or different, are each a hydrogen atom, a $C_1$-$C_4$-alkyl radical or, together, can also be a second bond between carbon atoms 6 and 7,
- B and $R^2$, together for a methylene or ethylene group,
- Z stands for the radical of a pentagonal or hexagonal ring, which is possibly substitued and possibly unsaturated,
- V stands for a possibly substituted carbocyclic or heterocyclic aryl radical,
- ring A strands for

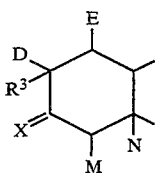   a)

M and N together are a second bond or M is a hydrogen atom and N is a hydroxy group in which case , B, $R^2$, G, $R^3$, D and E are then hydrogen atoms, and X is an oxygen atom, two hydrogen atoms or one hydroxyimino grouping N~OH, $R^3$ and D, which are the same or different, are each a hydrogen atom, a nitrile radical or a $C_1$-$C_4$-alkyl radical or, together, a methylene or ethylene group, E is a hydrogen atom, a $C_1$-$C_4$-alkyl radical, D and E together meaning a second bond between carbon atoms 1 and 2 or together a methylene group or

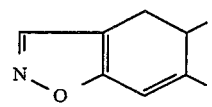 b)

or

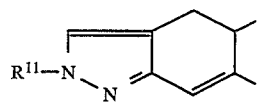 c)

wherein $R^{11}$ is a hydrogen atom or a $C_1$-$C_8$-alkyl radical, as well as, possibly, their pharmaceutically tolerated addition salts with acids.

Aryl radical V can be substituted and unsubstituted carbocyclic or heterocyclic radicals like, for example, phenyl, naphthyl, furyl, thienyl, pyridyl, pyrazolyl, pyrrolyl, pyrimidinyl, oxazolyl, pyridazinyl, pyrazinyl.

The invention relates in particular to compounds of general formula I, in which V implies the radical of a phenyl ring of general formula

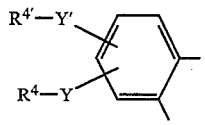

where
$R^4$ $R^{4'}$ which are the same or different, mean respectively a hydrogen atom, a cyanide radical, an —$OR^{11}$—, —S $(O)_kR^{11}$—, $N(O)_nR^{11}R^{12}$, —, —O—$SO_2R^{13}$, —, —$P(O)(OR^{14})_2$—, $SiR_3^{14}$—or $SnR_3^{14}$—group with k in the meaning of number 0, 1 or 2, n in in the meaning of number 0 or 1,
$R^{11}$ in the meaning of a hydrogen atom or $C_1$-$C_8$-alkyl radical,
$R^{12}$ in the meaning of $R^{11}$, a cyanide or $C_1$-$C_{10}$-acyl radical,
$R^{13}$ in the meaning of a perfluorated $C_1$-$C_4$-alkyl radical,
$R^{14}$ in the meaning of a $C_1$-$C_4$-alkyl radical,
$R^{11}$ and $R^{12}$ in an —$N(O)_nR^{11}R^{12}$ group can also together, with the inclusion of N, a 5- or 6-member heterocyclic ring, it being possible for another heteroatom N, O or S to be contained in the ring,
Y and Y', which are the same or different, mean respectively a direct bond, a straight-chain or branched alkylene group, possibly containing double or triple bond(s), with as many as 20 carbon atoms, which, as the case may be, is substituted with one or more more oxo—, C—, —$C_{1-0}$—acyloxy—, —$OR^{11}$—, $S(O)_kR^{11}$—and/or —$N(O)_nR^{11}R^{12}$— group(s) or possibly a substituted aryl radical, or $R^{4}$-Y and $R^{4'}$-y' together mean the radical of a possibly substituted, saturated, unsaturated or aromatic 5- or 6-member ring with 0 to 2 oxygen, sulfur atoms and/or $NR^{11}$ groups, provided that k and n are greater than 0 only if $R^{11}$ imply a $C_1C_8$—alkyl radical.

If Y-R$^4$=H and Y' is the ethylene group replaced with an oxo group in position 1 and R$^4$=H, then Y'—R-4'is the acetyl group that plays a preferential role within the scope of the invention.

In the substitution of the phenyl ring preference is given to monosubstitution in position 3, 4 or 5 and to disubstitution in position 4 and 5 or 3 and 4, with the formation of a second ring condensed on, e.g. a cyclohexene, pyrrole, furyl, pyrroline, 1,3-dioxacylopentene, pyrazoline, didehydromorpholine, didehydropiperidine, dideydropiperazine, dehydropyrane, pyrimidine, pyridine, pyrazine, 1,4- dioxacyclohexane ring. The alkyl radicals standing for R$^1$ and R$^{11}$ respectively, R$^2$R$^3$, B, G and D are to carry 1 or 2 carbon atoms in the case of R$^1$, 1 to 8 in the case of R$^{11}$ and otherwise 1 to 4, the methyl, ethyl, propyl, isopropyl, butyl respectively methyl, ethyl, propyl groups being preferred. R$^{12}$ implies an acyl radical, the formyl, acetyl, propionyl, butyryl and benzoyl group is preferred. R$^{11}$ and R$^{12}$ also imply together, with the inclusion of the nitrogen atom, a heterocyclic five- or six-member ring that can contain an O or S atom in addition to the N and C atoms; examples being the pyrrole, pyrrolidine, piperidine, piperazine, morpholine, oxa and thiazolidine as well as the thiadiazolidine rings.

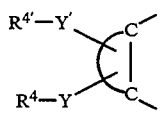

Moreover, the invention also relates in particular to compounds of general formula I, in which Z implies the radical of a ring of the formula

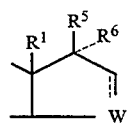

where
R$^1$ is methyl or ethyl the broken line originating at W. means the possible presence W means a CH$_2$—, CH—, CH$_2$CH$_2$— or CHCH$_2$—radical,

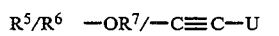
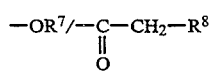
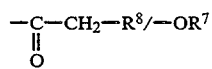
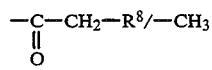
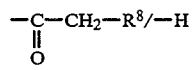
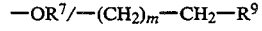
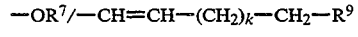
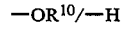
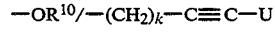

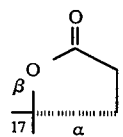

with R$^7$ in the meaning of a hydrogen atom or acyl radical with to 4 carbon atoms, U in the meaning of a hydrogen atom, an alkyl, hydroxyalkyl, alkoxyalkyl, acyloxyalkyl group with resspectively 1 to 4 carbon atoms in the alkyl and acyl radicals, R$^9$ in the meaning of a hydrogen atom, a hydroxy or cyanide radical, an O-alkyl or O-acyl group with respectively 1 to 4 carbon atoms, R$^8$ in the meaning of a hydrogen atom, a hydroxy group, an alkyl, O-alkyl or O-acyl group with respectively 1 to 4 carbon atoms, R$^{10}$ in the meaning of a hydrogen atom, an alkyl or acyl with respectively 1 to 10 carbon atoms, m in the meaning of 0, 1, 2 or 3, k in the meaning of 0, 1 or 2.

The alkyl, alkoxy and acyloxy groups contained in R$^5$ and R$^6$, respectively R$^7$, R$^8$, R$^9$, R$^{10}$ and U, can contain respectively 1 to 4 carbon atoms, the methyl, ethyl, propyl, isopropyl, methoxy, ethoxy, propoxy, isopropoxy, formyl, acetyl, propionyl and isopropionyl group being preferred.

Of the alkenyl radiclas R$^6$ in the propenyl and butenyl group, which can be present in the E or Z configuration, are prefered, i.e. if R$^6$ implies —CH=(CH$_2$)—CH$_2$—R$^9$, k should preferably mean 0 or 1.

The new compounds of general formula I are manufactured in accordance with the invention by the method
wherein the compounds of formula II

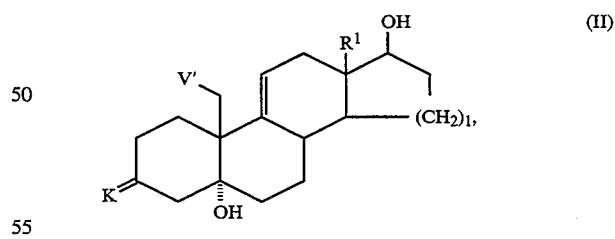

where
R$^1$ means a methyl or ethyl radical, 1 numbers 1 or 2,
K a blocked keto group in the form of the ketal or thioketal,
V' the radical of a possibly substituted carbocyclic or heterocyclic aromatic compound that carries a fluorine, chlorine, bromine, or iodine atom in the α-position to the point of attachment, any hydroxy, mercapto, amino, oxo and/or terminal acetylene groups present in V' being protected, are cyclized to form intermedate products of general formula IVa

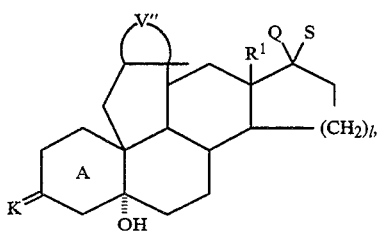

(IVa)

where Q is exculsively a β-hydroxy group and S exclusively an α-hydrogen atom, and in that then either first
a) the
  a) C-17 hydroxy group is, as the case may be, ozidized and subsequently,
  b) as the case may be, a hydroxy group in V' containing a protective group is liberated from said protective group, if desired a corresponding perfluoroalkyl sulfonate is produced from the hydroxy compound, optionally the perfluoroalkyl sulfonate is converted either directly or by exchangign the perfluoroalkyl sulfonate-leaving group for a tin trialkyl group via the corresponding tin trialkyl compound into a compound that displays, possibly after further reactions, the desired substitution pattern in V″, or first b) and then a) are carried out and afterwards c) ring D is functionalized in the desired way according to methods known per se, the product thus obtained is subjected to the effect of a dehydrating agent capable of releasing the 3-oxo group, in order to split off the water while simultaneously forming the 4(5) double bond, and the desired functions of rings A and B are subsequently introduced in the steriod structure, possibly after renewed protection of intermediately released functional groups contained in V and/or Z or
d) the product thus obtained is subjected to the effect of a dehydrating agent capable of releasing the 3-oxo group, in order to split off the water while simultaneously formign the 4(5) double bond, the desired functions of rings A and B are introduced in the steroid structure, and ring D is subsequently functionalized in the desired fashion after protecting the 3-oxo group, or in that steps a) and b) are performed after step c) or d), the product thus obtained liberates, as the case may be, from protective groups, the hydroxy, mercapto and/or amino group(s) possibly contained in V are, if desired, alkylized or acylized, a cyanide radical, if desired, introduced into the aryl substituent(s), the amino and/or sulfide group(s) possibly contained in the aryl substituent(s), are oxidized if desired and converted, if desired, with hydroxylamine hydrochloride into the product of general formula I, with X in the mean of a hydroxyimino group N∼OH and, as the case may be a pharmaceutically tolerated acid-addition salt is prepared.

To manufacture the intermediate products of general formula

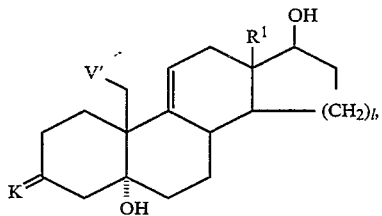

(II)

where
R¹ means a methyl or ethyl radical, 1 number 1 or 2,
K a blocked keto group in the form of the ketal or thioketal, V' the radical of a possibly substituted carbocylic or heterocylic aromatic compound that carries a fluorine, chlorine, bromine, or iodine atom in the α-position to the point of attachment, any hydroxy, mercapto, amino, oxo and/or terminal actylene groups being protected, as well as, in particular, to manufacture the compounds of general formula II, which are likewise the subject matter of the invention and in which V' implies the radical of a phenyl ring of the formula

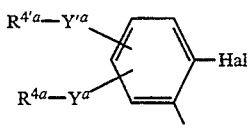

where
Hal means a fluorine, chlorine, bromine or iodine atom, Rhd 4a, $R^{4'a}$, $Y_a$ and $Y'^a$ have the same meaning as $R^4$, $R^{4'}$, Y and Y', with the exclusion of the cyanide radical, any hydroxy, mercapto, amino, oxo and/or terminal acetylene groups being protected, V' can also be a 5- or 6-member heteroaromatic ring with 0 to 2 N, O or S atoms of the formula

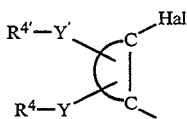

where Hal means a fluorine, chlorine, bromine or iodine atom,
$R^{4a}$, $R^{4'a}$, $Y^a$ and $Y'^a$ have the same meanings as $R^4$, $R^{4'}$, Y and Y', with the exclusion of the cyanide radcal, any hydroxy, mercapto, amino, oxo and/or terminal acetylene groups being protected. one proceeds from the epoxides of general formula III obtained in accordance with the prescriptions in, for example, European Patent Application Publication No. 0110434, DE 34 38 484 or European Patent Application Publication No-0127864,

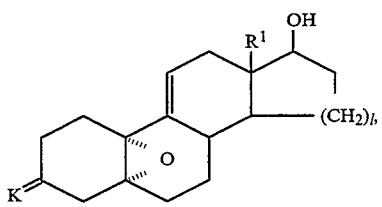

(III)

where $R^1$, l and K have the aforementioned meaning The intermediate products of general formula II in accordance with the invention are yielded by Grignard addition to the aforementioned epoxides (Tetrahedron Letters 1979 2051) of arylmethyl halogenides of general formula V V'CH₂Hal (V), where Hal implies a chlorine, bromine or iodine atom, which carry a fluorine, chlorine, bromine or iodine atom in position 2 where the aromatic compound (carbocyclic or heterocyclic) is attached to the methyl group.

The new compounds of general formula II are cyclized after protection of the functional groups possibly present in V'. The protective hydroxy, mercapto and keto groups subsumed by V' and K are groups that are easy to split off in an acid medium, examples being the methoxymethyl, ethoxymethyl, tetrahydropyranyl, ethylenedioxyketal, ethylenedithioketal or 2,2-dimethyltrimethylendioyletal group. Protective groups for amino and terminal acetylene groups (e.g. the trimethylsilyl and terp.-butyldimethylsilyl group) are likewise familiar to the expert and are also separated by methods described in the literature after tile desired sequence of reactions [Synthesis 1980, 627, J. Org. Chem. 46 (1986) 2280].

Conversion of the compounds in accordance with II into the new 19,11β-bridged steroids of general formula IVa

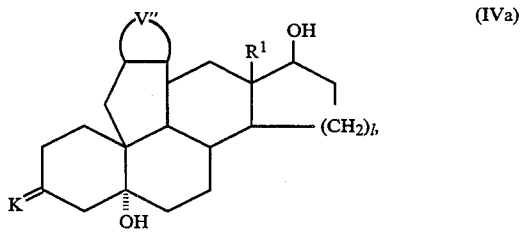

which are likewise the subject matter of the invention and where $R^1$ K and l have the aforementioned meaning and V''' the same meaning as V, but any hydroxy, mercapto, amino, oxo and/ or terminal acetylene groups present in V are protected, is achieved, in the event that the β-halogen substituent in V' is a bromine or iodine atom, by methods known per se (Tetrahedron Letters 1982, 2575; 1985, 6001; 1986, 2833; J. Am. Chem. Soc. 1982, 104, 2321; Radicals in Organic Synthesis: Formation of Carbon-Carbon Bonds, Pergamon Press, 1986) by reductive radical cyclization.

A corresponding method for fluorine and chlorine-substituted aromatic compounds has been unknown hitherto. It was now discovered that this cyclization is surprisingly successful, with a good yield, when the educt is treated with an electropositive metal, e.g sodium, potassium, lithium or calcium, in liquid ammonia, mixed with one or more suitable organic solvent(s), e.g. diethyl ether, dimethoxyethane (DME), dioxane, or tetrahydrofurnae at temperatures between −10020 and −30° C., preferably −78° to −60° C. That this cyclization is also feasible with the fluoride ion as the leaving group must be viewed as especially surprising.

This new method is also to be applied in the case of bromine and iodine-replaced aromatic compounds.

The cyclization products yielded thereby are converted into the final products of general formula I, which are desired in the end, by analogous methods described in the literature (e.g., J. Fried, J.A. Edwards, "Organic Reactions in Steroid Chemistry", Van Nostrand Reinhold Company, 1972, Vol. 1 and 2; "Terpenoids and Steroids", Specialist Periodical-Report, The Chemical Society, London, Vol. 1-12 ), in as much as one either first a) oxidizes the C-17-hydroxy group, as the case may be, and subsequently, b) as the case may be, a hydroxy group in V' containing a protective group is liberated from said protective group, if desired a corresponding perfluoralkyl sulfonate is produced from the hydroxy compound, optionally the perfluoroalkyl sulfonate is converted either directly or by exchanging the perfluoroalkyl sulfonate-leaving group for a tin trialkyl group via the corresponding tin trialkyl compound into a compound that displays, possibly after further reactions, the desired substitution pattern in V''' or first carries out b) and then a) and afterwards c) functionalizes ring D in the desired way according to methods known per se, subjects the product thus obtained to the effect of a dehydrating agent capable of releasing the 3-oxo group, in order to split off the water while simultaneously forming the 4(5) double bond, and subsequently introduces the desired functions of rings A and B in the steroid structure, possibly after renewed protection of intermediately released functional groups contained in V and/or Z or d) subjects the product thus obtained to the effect of a dehydrating agent capable of releasing the 3-oxo group, in order to split off the water while simultaneously forming the 4(5) double bond, introduces the desired functions of rings A and B in the steroid structure and subsequently functionalizes ring D in the desired fashion after protecting the 3-oxo group, or performs steps a) and b) after step c) or d), liberates, as the case may be the product thus yielded from protective groups, alkylizes or acylizes if desired the hydroxy, mercapto and/or amino group(s) contained in V, introduces if desired a cyanide radical into the aryl substituent(s), oxidizes if desired time amino and/or sulfide group(s) possibly contained in the aryl substituent(s), converts it if desired with hydroxylamine hydrochloride into the product of general formula I, with X in the meaning of a hydroxyimino grouping N∼OH and, as the case may be, prepares a pharmaceutically tolerated acid-addition salt.

In the course of these reactions it might become necessary to introduce intermediately protective groups into intermediate products once again, e.g. for functional groups contained in Z, with subsequent functionalization of rings A and B, or for the 3-keto group with subsequent construction of ring D.

The oxidation of the 17-hydroxy group, which is required for the manufacture of nearly every final product, is effected in the way known per se, e.g. by Oppenauer, oxidation or chromic acid reagents (Jones reagent or chromic acid pyridine). The 3-keto function is released at the same time as the water is split off and the 4(5) double bond created by treatment with acid or an acid ion exchanger. The acid treatment is carried out in the way known per se by dissolving the corresponding 5α-hydroxy-3-ketal in a solvent miscible with water, such as aqueous methanol, ethanol or acetone, and subjecting the solution to catalytic quantities of mineral or sulfonic acid like hydrochloric acid, sulfuric acid, phosphoric acid, perchloric acid or p-toluene sulfonic acid, or an organic acid like acetic acid, until any protective groups have been removed and any water has been split off. The conversion, which takes place at temperatures from 0° to 100° C., can also be done with an acid ion exchanger. The 6ourse of the conversion can be followed by analytical methods, e.g., by thin-layer chromatography of specimens.

In general, the protective groups are removed and water split off in a one-step reaction by letting the corresponding 5α-hydroxy-3-ketal respectively 5-en-ketal react in a strongly acid medium for a certain period of time, as described in example 1c). But it is just as possible, in accordance with the invention, to remove the protective groups and split off the water in two separate reaction steps by first obtaining and, as the case may be, isolating the corresponding 5=-hydroxy-3-keto compound by first treating the corresponding 5-hydroxy-3ketal for a short while in a moderately acid medium. The 5-hy- droxy-3-keto compound is then converted into the 3-keto-4-en compound by further reaction with acid, the water being split off.

A very special advantage of this invention is to be seen in the great bandwidth of substituents that can be introduced in the carbocyclic or heterocyclic aryl radical V (M. Pereyre, J.-P. Quintard, A. Rahm, Tin in Organic Synthesis; Butterworths, 1987). For one, the substituents $R^4$-Y and respectively, $R^{4'}$-Y' present in the later final product can be directly introduced by coupling an arylmethyl halogenide of general formula V, V'CH$_2$Hal, which arylmethyl halogenide is correspondingly substituted in the aryl radical, by Grignard's reaction with a suitable 5α,10α-epoxide of general formula III and processing the intermediate product of general formula II in the way already described.

The number of compounds substituted in V that can be manufactured in this way is relatively limited, since not all the substituents desired in the final product do withstand unharmed the conditions for Grignard's reaction, which has to take place at V'CH$_2$Hal prior to coupling with the respective 5α, 10α-epoxide III, and, in particular, the reductive conditions during cyclization of intermediate product II into a 19,11β-bridged steroid of general formula IV.

In another practical embodiment of the method in accordance with the invention, however, it is possible to vary the substituent(s) in aryl radical V throughout a wide range by only introducing the substituent(s) after cyclization, namely before, simultaneously with or only after completion of the structure of rings A, B, and D. For this purpose at least one of the protected hydroxy groups present in radical V" respectively V is liberated from its protective group and the corresponding perfluoroalkylsulfonate compound produced from the free OH-compound by conversion with perfluoroalkylsulfonic acid anhydride (alkyl=$C_1C_4$) by methods known per se [P. J. Stang, M. Hanack and L.R. Subramanian, Synthesis 85 (1982).]

In this connection is necessary to proceed either in such a way that in a reaction catalyzed by transition metals (preferably Pd°) the perfluoro transition group is displaced by the desired substituent or its preceding stage, the substitution to take place, essentially, almost simultaneously (J.E. McMurry and S- Mohanraj, Tetrahedron Letters, 24, No. 27, p. 2723-2726, 1983; X. Lu and J. Zhu, Communications, p. 726-727, 1987; Q.-Y. Chen and Z.-Q. Yang, Tetrahedron Letters 27, No. 10, p. 1171-1174, 1986; S. Cacchi, P.G. Ciattini, E. Morera and G. Ortar, Tetrahedron Letters, 27, No. 33, p. 3931-3934, 1986; A. M. Echavarren and J. K. Stille, J. Am. Chem. Soc. 1987, 109, p. 5478-5486), or a corresponding tri-organylstannyl compound, preferably tri-n-alkylstannyl compound, is produced intermediately from the perfluoroalkylsulfonate compound by catalysis with transition metals [J. K. Stille, Angew. Chem. 98 (1986), pp. 504–519]. In a single-pot reaction with a halogensubstituted, preferably bromine- or iodine-substituted carbocyclic or heterocyclic aromatic compound [Y. Yamamoto, Y. Azuma, H. Mitoh, Communications, pp. 564–565, 1986; T.J. Bailey, Tetrahedron Letters, 27, No. 37, pp. 4407–4410), 1986J, which can, as the case may be, also carry further substituents, this is converted into a 19,11β-bridged steroid; aryl radical V and respectively V" therein contains the desired substituent or a predecessor.

The intermediately occurring tri-n-alkylstannyl compounds can also be isolated as a substance, as is substitutionally demonstrated by example 39a)α) in the case of the 11β, 19-(4-tri-n-butylstannyl-O-phenylene)-3,3-(2.2-dimethyltrimethylenedoxy)- -androstan-5α, 17β-diol.

1,2 and/or 6,7 double bonds are introduced in addition to the 3,4 double bond by familiar methods, e.g., with dehydrating agents like selenium dioxide, chlotanil, thalliumtriacetate or dichlorodicyanobenzoquinone (DDQ) respectively, by allyl or dienol ether bromination and subsequent separation of the hydrogen bromide [J. Fried, J. A. Edwards, Organic Reactions in Steroid Chemistry, Van Nostrand Reinhold Company, 1972, p. 265–374), 1; Tetrahedron 42, (1986) 2971].

The allyl bromination is done, for example, with N-bromosuccinimide, N-bromoacetamide, 1,3-dibromo-5,5-dimetbylhydantoin or dibromotetrachlorethane in the presence of a radical former like dibenzcylperoxide in a solvent. Possible solvents are aprotic solvents like dioxane and chlorated hydrocarbons, e.g. carbon tetrachloride, chloroform or tetrachloroethylene. Conversion takes place between 0° C. and the boiling temperature of the solution.

The dienol ether bromination is effected, for example, analogous to the specification in Steroids I, 233.

The hydrogen bromide is split off, and the Δ$^6$ double bond established, by heating the 6-bromine compound with alkaline agents, preferably with lithium bromide and lithium carbonate or with lithium bromide and calcium carbonate in an aprotic solvent like dimethylformamide at temperatures between 50° and 120° C. Another possibility of splitting off the HBr is to heat the 6-bromine compound in collidine or lutidine.

Proceeding from a staturated ring A it is possible to introduce double bonds in the 1,2 and 4,5 positions at the same time, e.g., by brominating to form 2,4-dibromo-3-ketone and dehydrobromination of the dibromide with, for example, lithium or calcium carbonate and lithium bromide in dimethylformamide.

The 6-methylene group can be introduced for example, by proceeding from a 3-amino-3(4),5(6)-diene derivative through conversion with formalin in an alcoholic solution (Helv. Chim. Acta. 56 (1973) 2396) into a 6α-hydroxymethyl group and subsequent acid separation of the water, e.g. with hydrochloric acid in dioxane/water, or by proceeding from a 3-alkoxy3(4),5(6)-diene derivative, analogous to the method described in U.S. Pat. No. 4,544,555 or directly by proceeding from a 3-oxo4(5)-ene derivative analogous to the specification in Synthesis (1982) 34.

The 6-methylene compound is methylenated with dimethylsulfoxoniummethylide to form the 6,6-ethylene compound. To do so, the 6-methylene steroid is added to a suspension of trimethylsulfoxoniumiodide with sodium hydride in mineral oil and dimethylsulfoxide or to a solution of trimethylsulfoxonoumiodide and sodium hydroxide in dimethylsulfoxide. The reaction is completed after 15 to 60 minutes at 20° to 40° C. (J. Am. Chem. Soc. 84 (1962) 866; European patent application on 0150157).

A 2-methylene group is introduced analogous to the method of A.J. Manson and D. Wood [J. Org. Chem. 32 (1367) 34343]or the methods cited there.

The 2-methylene compound is methylenated to form the 2,eethylene compound analogous to the methylenation of the 6methylene compound [cf. also Chem. Ber. 98 (1965) 1470]. .

Monoalkylated and, respectively dialkylated compounds in position 2 can, for example, be obtained analogous to the method of L. Nedelec, Tetrahedron 30 (1974) 3263.

Alkylated compounds in position 1 and respectively position 7 are obtained by 1,4 and respectively 1,6 addition to the corresponding enones by familiar methods [J. Fried, J. A. Edwards: Organic Reactions in Steroid Chemistry, Van Nostrand Reinhold Company, 1972, pp 75 to 82, 2; and J. Am. Chem. Soc. 99 (1977) 16733.

Alkylated compounds in position 6 can, for example, be obtained by opening the corresponding 5α,6α-epoxides and subsequent reactions (J. Fried, J.A. Edwards: Organic Reactions in Steroid Chemistry, Van Nostrand Reinhold Company, 1972, pp 82 to 86, 2).

1α,2α-, 6α, 7α-, 6β, 7β-methylene compounds or a combination of the 1α, 2α-methylene structural element with the two 6,7-methylene structural elements can be obtained by the addition of diazomethane or dimethylsulfoxoniummethylide to the corresponding enones by the Simmons-Smith reaction (J. Fried, J. A. Edwards: Reactions in Steroid Chemistry, Van Nostrand Reinhold Company, 1972, pp 100–126; Rev. Soc. Quim. Mex. (1969) ]71A; Chem. Ber. 101 (1986) 935; Chem. Ber. 99 (1966) 1118; Zeitschr. f. Naturf. 19b (1964) 944) of the corresponding allyl alcohols.

The isoxazole ring annellated to positions 2 and 3 is produced by synthesis of the 2-hydroxymethylene compounds [Steroids 6 (1962) 178; J. Amer. Chem. Soc. 83 (1961) 1478]and their conversion with hydroxylamine [J. Med. Chem. 6 (1963) 1].

[2,3-d]isoxazoles are also good starting materials for the synthesis of 2-cyano-steroids [J. Med. Chem. 6 (1963) 13.

The pyrazole ring annellated to positions 2 and 3 is produced by conversion of 2-hydroxymethylene-3-oxo educts with $R^{11}$-substituted hydrazine (U.S. Pat. No. 3,704,295).

The chlorine and, respectively, the methyl substituents are introduced into C-6 of the steroid structure by, for example, the methods indicated in German patent specification 1,158,966 and, respectively in U.S. Pat. No. 4,544,555 and 4,196,203 via the corresponding 6,7-epoxides and, respectively, 6-methylene derivatives as well as by oxidation of the 6-chloro-3,5-dienol ether with dichlorodicyanobenzoquinone (DDQ) in acid conditions [Belgian patent 621,197 (1962)].

The 3-oxo group can be removed to form a final product of general formula I, with X in the meaning of two hydrogen atoms, e.g., by thioketalization and subsequent reductive separation in accordance with the specification set out in DOS 2805490.

Educts with á D-homo steroid structure can also be obtained, for example, by Tiffeneau's rearrangement analogous to the specification published in Australian J. Chem 8 (1955), 519, and in "Organic Reactions in Steroid Chemistry" Vol. 2, 388. The requisite 17α-aminomethyl-17β-hydroxy compounds are, for example, rendered accessible by opening the 17,20-spiroepoxides with ammonia or also by lithium-aluminum reduction of acetylated 17β-hydroxy-17α-cyano compounds. The spiroepoxides are rendered accessible by converting the corresponding 17ketones with dimethylsulfoniummethylide in dimethylformamide [Journal f. prakt. Chemie 314 (1972), 667–668. The acetylated cyanohydrins are rendered accessible by adding hydrocyanic acid to the corresponding 17-ketones and subsequent acetylation in accordance with known specifications (e.g. Australian J. Chem. 8 (1955), 519).

Educts with an unsaturated D ring are, for example, accessible by modified Saegusa oxidation (Tetrahedron 42(1986) 2971) of the corresponding enol compounds of the 17-ketone. For example, the trimethylsilylenol ether can be obtained by converting the 17-ketone into the corresponding enolate with lithiumdiisopropylamide in tetrahydrofuran and recovery with trimethylchlorosilane (Synthesis 1983, 1).

The substituents $R^5$ and $R^6$ are introduced by the customary methods used to build up the C-17 side chain by nucleophile addition to the 17-ketone - obtained, for example, by Oppenauer's oxidation of the C-17-hydroxy group - and subsequent reactions ("Terpenoids and Steroids", Specialist Periodical Report, The Chemical Society, London, Vol. 1–12).

The substituent -C≡C-U, with U in the aforementioned meaning, is introduced as $R^6$ with the help of a compound of general formula MC≡C-U', in which U'πis the radical U protected by, for example, trimethylsilyl or tert.-butyldimethylsilyl, or if U is an alkyl group with 1–4 C atoms, U' itself is the radical U.

The organometallic compound can also be formed in situ and made to react with the 17-ketone. Thus, for example, the 17ketone can be allowed to react in a suitable solvent with acetylene and an alkali metal, in particular potassium, sodium or lithium, in the presence of an alcohol or in the presence of ammonia. The alkali metal can also be allowed to react the form of, for example, methyl- or buty]l]th]um. Suitable solvents are, in particular, dialkyl ether, tetrahydrofuran, dioxane, benzene and toluene.

The 3-hydroxy-propine, -propene and, respectively -propane can be introduced into position 17 by converting the i7-ketone with the dianion of the propargyl alcohol (3-hydroxypropine), e.g., with the dipotassium salt of the propargyl alcohol generated in situ, to form the 17α-(3chydroxyprop-l-inyl)-17β-hydroxy derivative or with metallized derivatives of the 3-hydroxypropine, e.g. with 1-lithium-3-(tetrahydropyran-2'-yl- oxy)-prop-l-in-l-ide, to form the 17-[3-(tetrahydropyran-2'-yloxy)-prop-l-inyl]-17β-hydroxy derivative, which can subsequently be hydrated to form the 17-(3-hydroxypropyl- and respectively. hydroxy-propenyl)-17β-hydroxy compounds. This is effected, for example, by hydration at room temperature and normal pressure in solvents like methanol, ethanol, propanol, tetrahydrofurane (THF) or acetic ether with the addition of precious-metal catalysts like platinum or palladium.

Homologous hydroxyalkine, hydroxyalkene and hydroyalkane groups are introduced in a similar way with homologues of the propargyl alcohol.

The compound with the Z-configured double bond in the hydroxypropenyl group is obtained by hydration of the acetylenic triple bond with a disactivated precious-metal catalyst (J. Fried, J. A. Edwards: Organic Reactions in Steroid Chemistry, Van Nostrand Reinhold Company, 1972, p. 134; and H. O. House: Modern Synthetic Reactions, 1972, p. 19). Possible disactivated precious-metal catalysts are, for example, 10% palladium on barium sulfate in the presence of an amine or 5% palladium on calcium carbonate with the addition of lead(II) acetate. Hydration is discontinued after one equivalent of hydrogen has been taken up. The compound with the E-configured double bond in the hydroxypropenyl group is obtained by reduction of the acetylenic triple bond in a manner known per se. A large number of methods for the conversion of alkines into trans-olefines are described in the literature, e.g. reduction with sodium in liquid ammoniac (J. Am. Chem. Soc. 63 (1941) 216), with sodium amide in liquid ammonia (J. Chem. Soc. 1955, 3558), with lithium in low-molecular amines (J. Am. Chem. Soc. 77 (1955) 3378), with boranes (J. Am. Chem. Soc. 93 (1971) 3395 and 94 (1972) 6560), with diisobutyl aluminum hydride and methyl-lithium (J. Am. Chem. Soc. 89 (1967) 5085) and, in particular, with lithium aluminum hydride/alcoholate (J. Am. Chem. Soc. 89 (1967) 4245). Another possibility is reduction of the triple bond with chromium(II) sulfate in the presence of water or dimethylformamide in a slightly acid medium (J. Am. Chem. Soc. 86 (1964) 4358) as well as, in general, reduction by reaction with transition-metal compounds with a change of the oxidation stage.

The hydroxyalkenes can also be introduced directly by addition of a corresponding metallized hydroxyalkenyl compound, e.g. 1-1lithium-3-(tetrahydropyran-2'-yloxy)-prop-l(E)-ene (J. Org. Chem. 40, 2265) or 1-1lithium-3-tetrahydropyran-2'-yloxy)-prop-l(Z)-ene. (Synthesis 1981, 999). Homologues can likewise be introduced in this manner.

The introduction of 3-hydroxypropane in position 17 can likewise be effected by converting the 17-ketone with metallized derivatives of 3-halogen-propanols - the hydroxy group being present in the metallization stage-in the form of an alcoholate (Tetrahedron Letters 1978, 3013) or in the form of a protected function (J. Org. Chem. 37, 1947) - to form the 17-(3-hydroxypropyl)-17β-hydroxy compound respectively the compound protected at the terminal hydroxy group. Possible protective groups are, for example, the ethoxyethyl, tetrahydropyranyl and methoxymethyl groups. If final products of formula I are desired with $R^5/R^6$ in the meaning of

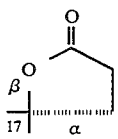

then the 17-(3-hydroxypropyl)-compound is oxidized in the known manner, e.g. with Jones' reagent, manganese dioxide, pyridinium dichromate, pyridinium chlorochromate, chromic acid pyridine or the Fetizon reagant silver carbonate/celite (Compt. rend. 267 [1968]900).

The final products of formula I with $R^5/R^6$ in the meaning of

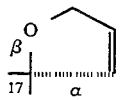

are yielded by the ring-closure reaction of the corresponding 17- ( 3-hydroxyprop-1- ( Z ) -enyl-17B -hydroxy educt.

The 17-cyanomethyl side-chain is built from the 17-ketone in the way known per se, e.g., by way of the 17-spiroepoxide and separation of the spiroepoxide with HCN in accordance with Z. Chem 18 (1978) 259-260.

The 17-hydroxyacetyl side-chain is also introduced by methods known per se, e.g., in accordance with the methods described in J. Org. Chem. 47 (1982), 2993-2995, Chem. Ber. 113 (1984), 1184, or U.S. Pat. No. 4,600,538.

To introduce the groups

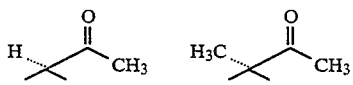

the 17-ketone is converted with tosylmethylisocyanide (Chem. Ind. 1972, 213) to form the 17-nitrile compound (Tetrahedron 31 (1975), 2151), which can be converted directly with methyl lithium or methylmagnesium bromide into the 17-acetyl compound, which yields the desired 17α-methyl-17β-acyl group after enolization with K-tert.-butylate in tetrahydrofuran and reaction with methyl iodide. This sequence involving the addition of methyl to the nitrile and subsequent alkylation can also be performed in the reverse order.

Free hydroxy and, respectively hydroxy, mercapto, and/or amino groups present in Z and, respectively, V can be alkylated or acylated in the way known per se.

Sulfides and/or dialkylamines contained in V can be converted by means of suitable oxidants (e.g., hydrogen peroxide or peracids) into the desired sulfoxides (n=1), N-oxides (n=1) [see, for example, Kontakte (Darmstadt) 1986, 3, p. 123 respectively sulfones (n=2). Compounds with a dialkylamine substituent in V can be converted into the corresponding (N-cyano-N-alkylaminoaryl) derivatives with a good yield by reaction with cyanogen bromide in aprotic solvents like, for example, dioxane, benzene or toluene at a raised temperature (amine separation by Braun's method) analogous to the specifications in, for example, Org. Reactions 7, 198 (1953), K. W. Bentley, Techniques of Organic Chemistry 11, 773 (1963) and Houben-Weyl, 5/4,151 (1960). Depending on the meaning $R^{12}$ is to have in the final product the latter are reduced in the way known per se to form the corresponding dialkylamine compounds (e.g., with diisobutyl aluminum hydride in toluene to form the N-formyl-N-alkyaminophenyl intermediate products and subsequently with lithium aluminum hydride)and, respectively, N—H—N—alkyl compounds (e.g., with lithium aluminum hydride or with lithium in liquid ammonia). If desired, the latter are subsequently acylated in the way known from the literature and, as the case may be, subsequently reduced with, for example, lithium aluminum hydride in the way known to yield the new dialkylamine derivative (cf. DE 36 23 038).

The compounds of general formula I yielded with X in the meaning of an oxygen atom can, if desired, be converted by reaction with hydroxylamine hydrochloride in the presence of tertiary amines at temperatures between $-20°$ and $+40°$ C. to form the oximes (formula I with X in the meaning of the hydroxyimino grouping N~OH, it being possible for the hydroxy group to be in the syn- or anti-position). Suitable tertiary bases are, for example, trimethylamine, triethylamine, pyridine, N,N-dimethylaminopyridine, 1,5-diazabicyclo[4.3.0]nonene-5 (DBN) and 1,5-diazabicyclo[5.4.0]-undecene-5 (DBU), pyridine being preferred.

The new compounds of general formula I and their addition salts with pharmaceutically tolerated acids are valuable pharmaceuticals. Thus, they have great affinity for the gestagen receptor and have a suprisingly wide range of gestagenic, antigestagenic, antiglucocorticoid, antimineralcorticoid and antiandrogenic properties. These important biological effects can be used for medical purposes.

Active ingredients of this kind, with marked antigestagenic activity, are suitable for initiating abortions since they displace the progesterone required to maintain pregnancy from the receptor. They are therefore valuable and in[eresting with regard to their use in postcoital control of fertility. They can also be used against hormonal disorders, to provoke menstruation and induce labor. Moreover, they can be used to treat hormone-dependent carcinomas.

The compounds of general formula I and their addition salts with pharmaceutically tolerated acids also display antiglucocorticoid activity and can therefore be used as pharmaceuticals for the treatment of corticoid-induced disorders (glaucoma) and to combat the side effects occurring during long-term treatment with glucocorticoids (Cushing's syndrome). Thus, they also permit to combat disorders attributable to a supersecretion of glucocorticoids, above all obesity, areteriosclerosis, hypertension, osteoporosis, diabetes and insomnia. The compounds of general formula I and their addition salts with pharmaceutically tolerated acids displaying gestagenic activity can be used, for example, in the treatment of amenorrhoe, dysmenorrhoe, hypermenorrhoe and luteal insufficiency, and those with antimineralcorticoid properties in the treatment of diseases involving hyperaldosteronism.

The compounds of general formula I and their addition salts with pharmaceutically tolerated acids displaying antiandrogenic activity can be used to treat hypertrophy and carcinoma of the prostate. Moreover, they permit specific therapy of androgenization symptoms in women: pathological growth of hair in the case of hirsutism, androgenetic alopecia and an elevated sebaceous gland function in the case of acne and seborrhoe can be influenced favorably.

The invention thus relates also to pharmaceuticals based on pharmaceutically tolerated compounds of general formula I, i.e., non-toxic compounds in the doses used, as well as their addition salts with pharmaceutically tolerated acids, possibly in cojunction with customary adjuvants and vehicles.

The compounds in accordance with tile invention and their salts can be processed by galenical methods known per se to yield pharmaceutical preparations for enteral, percutaneous, parenteral or local application. They can be administered in the form of tablets, coated tablets, gelatine capsules, granulates, suppositories, implants, injectable, sterile, aqueous or oleaginous solutions, suspensions or emul.sions, ointments, creams and gels.

In this connection the active ingredient(s) can be mixed with adjuvants customary in galenicals, e.g arabic gum, talcum, starch, mannitol, methylcellulose, lactose, tensides like Tweens$^{(R)}$ or Myrj$^{(R)}$ magnesium stearate, aqueous or non-aqueous vehicles, paraffin derivatives, wetting agents, dispersing agents, emulsifiers, preservatives and aromatic substances for adjustment of the taste (e.g., essential oils).

The invention thus relates also to pharmaceutical compositions that contain at least one compound in accordance with the invention as the active ingredient or one of its addition salts with pharmaceutically tolerated acids. Hydrochlorides and methane sulfonates must be especially mentioned as addition salts of the invented products with acids. A unit of dose contains approx. 1–100 mg of active ingredient(s). The dosage of the compounds in accordance with the invention is approx. 1–1000 mg per day in the case of humans.

The abortive effect was selected to identify the antigestagenic effect. The tests were carried out on female rats weighing approx. 200 g. After copulation the beginning of pregnancy was ascertained by demonstrating the presence of sperm in vaginal smears. The day on which sperm are verified is considered tile first day of pregnancy (=dl p.c). The animals were treated with the respective substance to be tested or the solvent after nidation of the blastocysts from d5 p.c. to d7 p.c. The animals were killed on d9 p.c. and the uteri examined for implants and points of resorption. Photographs were made of all the uteri. The lack of implants, pathological hemorrhagic or otherwise abnormal points of nidation were evaluated to be an abortion.

The test substances are dissolved in a mixture of benzylbenzoate and castor oil (ratio of 1+4). The vehicle volume per individual dose amounted to 0.2 ml. The treatment was subcutaneous.

The superiority of the compounds in accordance with the invention is to be shown by a comparison of the abortive action of 17α-(prop-1-inyl)-17β-hydroxy-11β, 19-(4-dimethylamino-o-phenylene)-4-androsten-3-one (A), 17α-(prop-l-inyl)-17β-hydroxy-11β,19-(4-acetyl-o-phenylene)-4-adrosten-3-one (B), 17β-(3-hydroxyprop-1-(Z)-enyl)-17β-hydroxy-11β, -19-(4-dimethyl-amino-o-phenylene)-4-androsten-3-one (C) and 17α(3-hydroxy-prop-1-(Z)-enyl)-17β-hydroxy-11β, 19-(4-methylthio-o-phenyl- ene)-4-androsten-3-one (D) with the 11β-(4-dimethylaminophen- yl)-17β-hydroxy-17α-(propin-l-yl)-4,9(10)-estradien-3-one (E) described in European patent specification 0 057 115 and the 11B-(4-dimethylaminophenyl)-17β-hydroxy-17α(-(3-hydroxy-prop-1-Z)-enyl)-4,9(10)-estradien-3-one (F) found in European patent specification 84730147.0.

From Table 1 it can be seen that only compounds A - D in accordance with the invention and compound F, which also goes back to the applicant, are still fully abortive at a dose of 1.0 mg/d s.c. The comparative substance E displayed only 50 % effectiveness at this dose. Compound B in accordance with the invention still displays full effectiveness even at a dose of 0.3 mg/d s.c. while F is no longer effective at this dose.

TABLE 1

Abortifacient activity of anti-progestatiolial compounds in early pregnant rats - Treatment on day 5-7 of gestation, autopsy on day 9 p.c.

| Compound | Dose mg/animal/day s.c. | Abortion rate n aborting/n treated rats | (%) |
|---|---|---|---|
| A | 3.0 | 4/4 | (100) |
|   | 1.0 | 4/4 | (100) |
|   | 0.3 | 1/4 | (25) |
| B | 3.0 | 4/4 | (100) |
|   | 1.0 | 4/4 | (100) |
|   | 0.3 | 4/4 | (100) |
| C | 3.0 | 4/4 | (100) |
|   | 1.0 | 4/4 | (100) |
|   | 0.3 | 0/4 | (00) |
| D | 3.0 | 4/4 | (100) |
|   | 1.0 | 4/4 | (100) |
|   | 0.3 | 1/4 | (25) |
| E | 3.0 | 4/4 | (100) |
|   | 1.0 | 2/4 | (50) |
| F | 3.0 | 4/4 | (100) |
|   | 1.0 | 4/4 | (100) |
|   | 0.3 | 0/4 | (0) |
| Vehicle controls: 0.2 ml benzyl benzoate + castor oil (1 + 4) | — | 0/5 | (0) |

To evaluate the antiglucocortoid activity the anti-thymolysis test was performed on the rat with 17α-(3-hydroxyprop-1-(Z)-enyl)-17β-hydroxy-11β,19-(4-dimethyamino-o-phenylene)-4-androsten-3-one (C), as representative of all compounds of general formula I, and the results were compared in turn with comparative substances E and F.

There is a great decline in the weight of the rat's thymus (=thymolitic effect) under the influence of glucocorticoids. If substances antagonistic to glucocorticoids are administered at the same time, inhibition respectively cancellation of the glucocorticoid-induced suppression of the thymus can be expected.

The tests were performed on adrenalectomized, juvenile, male rats weighing 100 to 130 g. Conditions in which the rats were kept: conventional, illumination rhythm: 10 hours of darkness/14 hours of light, average temperature 20°±2° C., standard rat diet (pellets), supply of tap water and 0.9 % NaCl solution via separate drinking bottles.

For subcutaneous application the substances were dissolved in a mixture of benzyl benzoate and castor oil (ratio of 1+4) and the respective daily dose injected in a vehicle volume of 0.2 ml. The dosages selected can be seen from Table 2.

The standard glucocorticoid substance used was dexamethasone in a dose of 0.01 mg/animal/day s.c. This dose induces—as related to the solvent control—an approximatley 75 % reduction in the weight of the thymus gland. Solvent: benzyl benzoate/castor oil (1+4), vehicle volume per daily dose: 0.2 ml.

Approx. 5 days prior to be commencement of treatment the animals were adrenalectomized under ether narcosis. They are assigned to the different test groups on a random basis; the extent of the random test can be seen from Table 2.

Groups treated:
dexamethasone control
solvent control
test-substance dose+dexamethasone The treatment lasted for 4 days (day1-4). On day 5 the animals were killed with $CO_2$. The weight of the thymus was determined and converted for mg/100 g of body weight.

To evaluate the antiglucocorticoid effect of a substance the difference between the solvent control and dexamethasone (0.01 mg/animal/day s.c.) is set at 100%.

The anti-glucocorticoid effect in mean percentage (cancellation of the thymus suppression induced by dexamethasone expressed in %) is calculated on the basis of the mean random-sample values by the following formula:

$$A = \frac{MV_s - MV_{Dexa}}{MV_{sol} - MV_{Dexa}} \cdot 100$$

In this connection $\left. \begin{array}{l} MV_s \\ MV_{Dexa} \\ MV_{sol} \end{array} \right\} = $ mean value for $\left\{ \begin{array}{l} \text{substance dosage + dexamethasone} \\ \text{dexamethasone} \\ \text{solvent control} \end{array} \right.$ As can be seen from Table 2, compound C produces a slight cancellation of the dexamethasone-induced suppression of the thymus only with the maximum test dose of 30.0 mg/d s.c. At lower doses (3.0; 10.0 mg/d s.c.) it was not possible to ascertain any antiglucocorticoid effect.

In comparison with compounds E (FIG. 2) and F (FIG. 1) the antiglucocorticoid activity of compound C is thus clearly reduced.

It is true that structurally similar steroids with a substituted aryl radical in position 10 and a 9(11) double bond are known from French patent application 86 400 057.5; but the known compounds always have an alkyl, alkenyl or alkinyl group in position 17α. These compounds, however, display considerable antiglucocorticoid activity, while their activity with regard to the progesterone receptor, and thus their antigestagenic effectiveness, is negligible.

With the compounds in accordance with the invention substances are thus made available which possess a new profile of effectiveness compared with the nearest state of the art, namely much higher antigestagenic effectiveness with only moderate antiglucocorticoid activity.

TABLE 2

Figure 1:
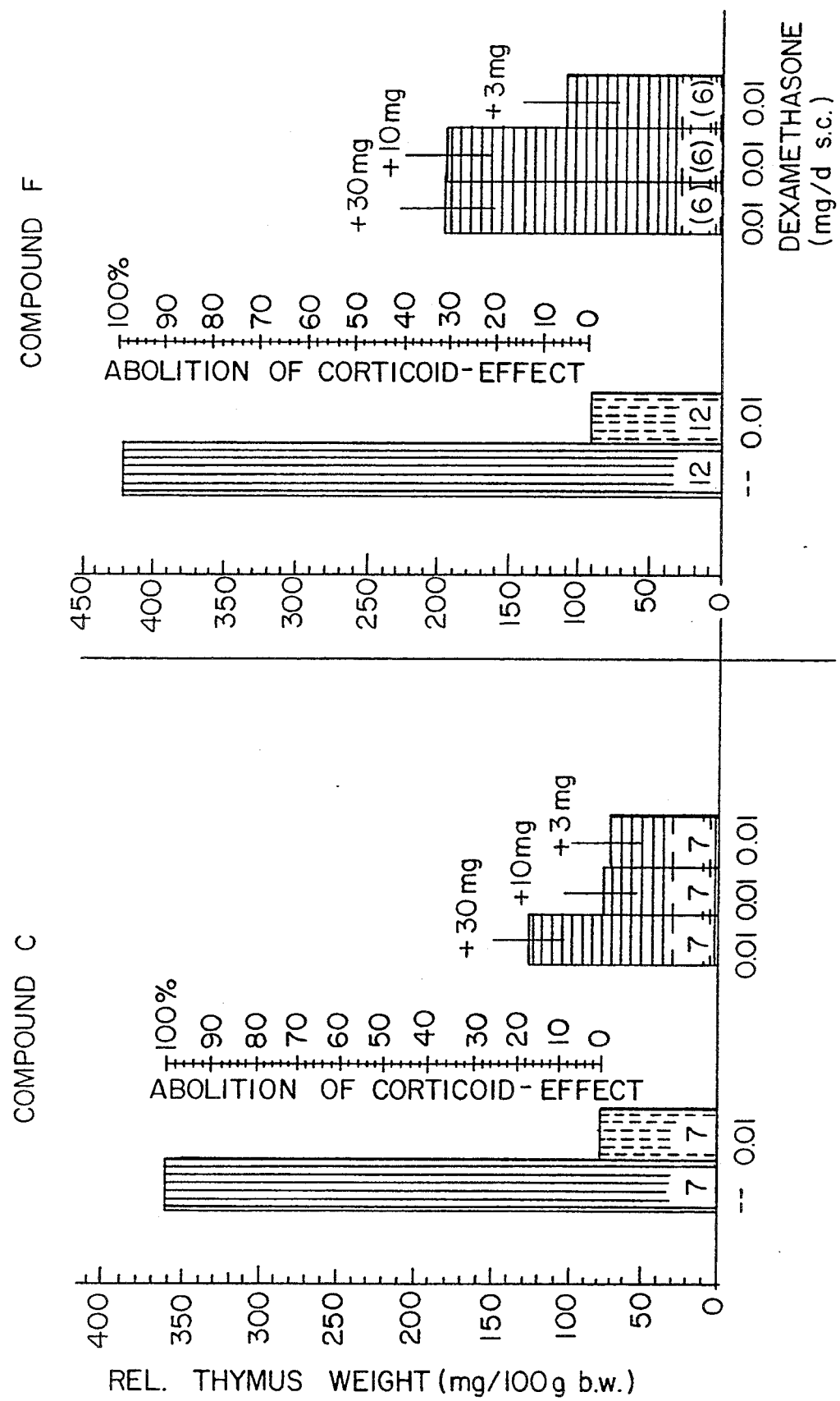
FIG. 1 illustrates the influence of selected compounds given s.c. upon dexamethason-induced thymus suppression in adrenal-ectomized male rats (b.w. 100-130 g). The graphs show treatment for four days (dose mg/d with thymus weight determined on day 5 [( )=n rats/group, |=95% confidence-interval for %-abolution].
Figure 2:
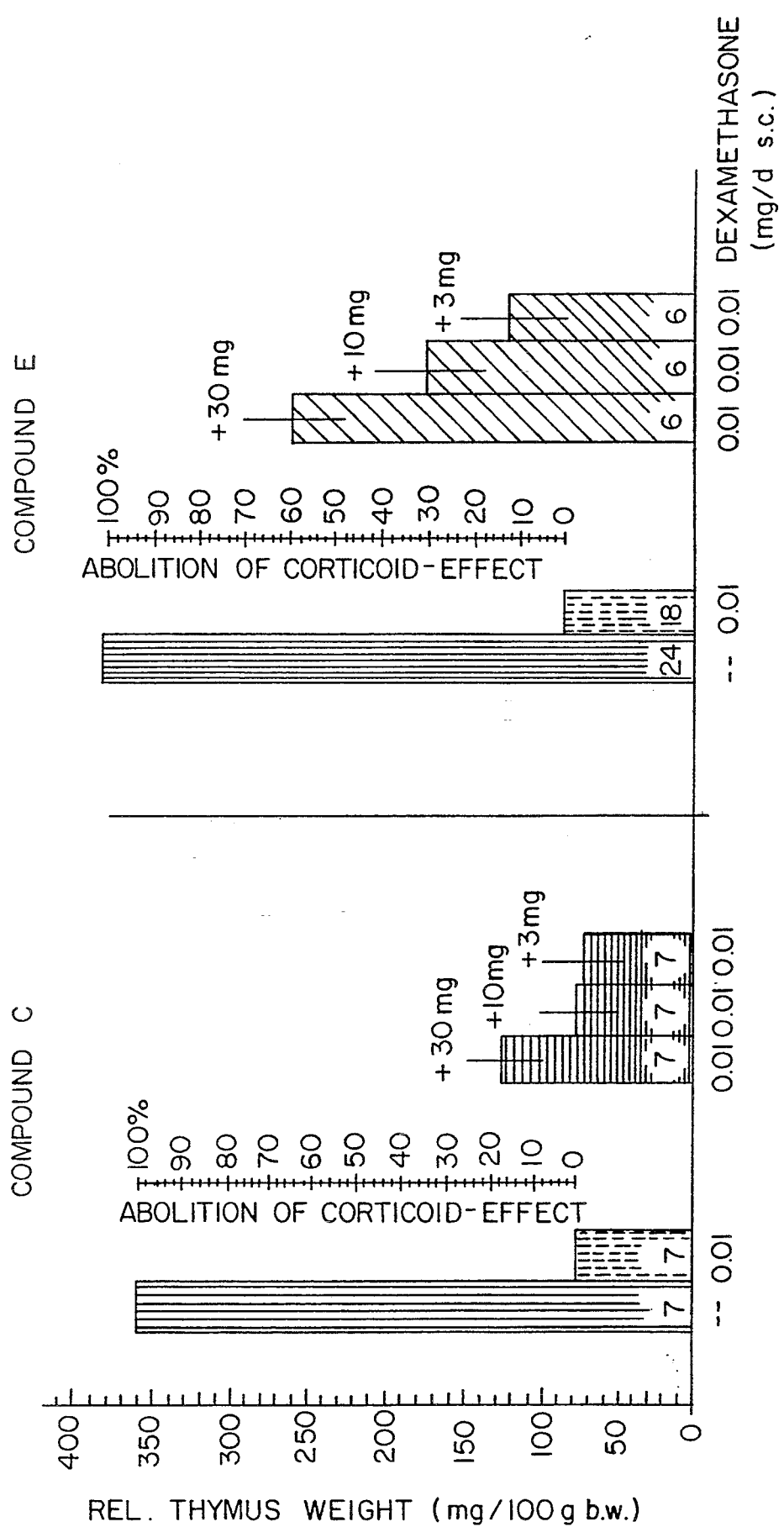
FIG. 2 also shows the influence of selected compounds given s.c. upon dexamethason-induced thymus suppression in adrenal-ectomized male rats (b.w. 100-130 g). Treatment again was for 4 days (dose (mg/d) with thymus weight determined on day 5 [( )=n rats/group, |=95% confidence-interval for %-abolition]

THYMOLYSIS TEST FOR ANTIGLUCOCORTICOID EFFECT
Cancellation of the dexamethasone-induced thymus suppression
(Treatment of adrenalectomized male rats (b.w. 100-130 g)
for 4 days, autopsy on day 5

| Dexamethason (mg/d s.c.) | Compound C | n | rel. thymus weight (mg/100 g b.w.) average ± diff. | Cancellation % |
|---|---|---|---|---|
| a)— | — | 7 | 361,0 ± 51,5 | |
| 0,01 | — | 7 | 77,4 ± 7,8 | |
| 0,01 | 3,0 | 7 | 72,4 ± 10,9 | −1,8(−12,1–7,5) |
| 0,01 | 10,0 | 7 | 76,9 ± 6,6 | −0,2(−10,4–9,1) |
| 0,01 | 30,0 | 7 | 125,0 ± 16,4 | 16,8(7,5–25,5) |

| Dexamethason (mg/d s.c.) | Compound F | n | rel. thymus weight (mg/100 g b.w.) aver. ± diff. | Cancellation % |
|---|---|---|---|---|
| a)— | — | 12 | 419,8 ± 61,9 | |
| 0,01 | — | 12 | 91,2 ± 16,6 | |
| 0,01 | 3,0 | 6 | 110,6 ± 16,3 | 5,9(−4,1–15,4) |
| 0,01 | 10,0 | 6 | 194,4 ± 27,9 | 31,4(22,1–40,5) |
| 0,01 | 30,0 | 6 | 197,3 ± 49,6 | 32,3(23,0–41,3) |

| Dexamethason (mg/d s.c.) | Compound E | n | rel. thymus weight (mg/100 g b.w.) aver. ± diff. | Cancellation % |
|---|---|---|---|---|
| a)— | — | 24 | 385,4 ± 51,3 | |
| 0,01 | — | 18 | 87,2 ± 13,2 | |
| 0,01 | 3,0 | 6 | 125,6 ± 19,9 | 12,9(0,5–,4) |
| 0,01 | 10,0 | 6 | 178,1 ± 44,8 | 30,5(18,6–42,0) |
| 0,01 | 30,0 | 6 | 264,7 ± 41,0 | 59,5(48,0–71,0) | a)Control group: benzyl benzoate + castor oil (1 + 4) 0.4 ml/d s.c.
( ) = 95% confidence interval for % cancellation
n = rats per group

EXAMPLES

In the following examples the chromatography is performed with a mixture of acetic ester and hexane, unless otherwise indicated.

Example 1

17β-hydroxy-11β,19-(o-phenylene)-4-androsten-3-one a) 19-(2-chlorophenyl)-3,3-(2,2-dimethyltrimethylenedioxy)-9(11)-androstene-5α,17β-diol 4.9 g of magnesium chips are added to 40 ml of abs. diethyl ether under inert gas, then mixed with 0.5 ml of 2-chlorobenzyl chloride and subsequently carefully mixed with 0.4 ml of 1,2-dibromomethane. After the reaction starts the remaining amount (18.4 ml) of the 2-chlorobenzyl chloride, dissolved in 135 ml of abs. diethyl ether, is added dropwise in the course of 40 minutes time without the temperature inside the reaction vessel rising above 30° C. After Grignard's reagent is formed the reaction mixture is cooled to 0° C. and 5α,10α-epoxy-3,3-(2,2-dimethyltrimethylenedioxy)-9(11)-estren-17β-ol (13.6 g), dissolved in 75 ml of abs. tetrahydrofurane, is slowly added dropwise. After subsequent stirring in an ice bath the reaction mixture is slowly heated overnight to room temperature and then poured over diluted ammonium chloride solution. The aqueous phase is extracted several times with acetic ester. The combined organic phases are washed neutral with a sodium-chloride solution, dried with sodium sulfate and concentrated in vacuo. The residue is chromatographed over aluminum oxide (neutral, stage III). This yields 14.8 g of the above compound.

$[\alpha]_D^{22} = -2°$ (CHCl₃; c=0.51)

Flashpoint: 188°-191° C. (ethylacetate)

b) 11β,19-(o-phenylene)-3,3-(2,2-dimethyltrimethylenedioxy)-androstane-5α,17β-diol 600 ml of anhydrous ammonia are concentrated in the reaction flasks at −65° C., with all moisture excluded, and mixed with 970 mg of freshly cut lithium chips. Immediately after development of the characteristic blue color a solution of 14 g of the product obtained in accordance with a) are added dropwise to 450 ml of abs. tetrahydrofuran in such a way that the reaction solution alternates between a colorless and a blue state. After addition, the surplus lithium is eliminated by adding ethanol dropwise, most of the ammonia removed by evaporation and the reaction mixture poured into water. The aqueous phase is extracted with acetic ester. The combined organic phases are washed neutral with a sodium-chloride solution, dried with sodium sulfate and concentrated in vacuo. Chromatography over aluminum oxide (neutral, stage III). This yields 10.3 g of the above compound.

$[\alpha]_D^{22} = +13°$ (CHCl₃; c=0.52)

Fp.:=164°-167° C. (ethylacetate)

¹H-NMR (CDCl₃) [δ]: 7.0-7.45 (4H, m, aromatic protons); 3.13 (1H, d J=16 Hz, proton on C-19); 2.68 (1H, d J=16 Hz, proton on C-19); 0.98 (3H, s, protons of a ketalmethyl group); 0.95 (3H, s, protons of a ketalmethyl group); 0.25 (3H, s, protons on C-18).

The title compound indicated in b) can also be prepared in the following way:

α) 19-(2-bromophenyl)-3,3-(2,2-dimethyltrimethylenedioxy)-9(11)-androstene-5α,17β-diol Analogous to Example 1a) 5 g of 5α,10α-epoxy-3,3-(2,2-dimethyltrimethylenedioxy)-9(11)-estren-17β-ol are allowed to react with 26.7 g of 2-bromobenzyl bromide. After chromatography this yields 5.9 g of the above compound in-the form of white foam.

¹H-NMR (CDCl₃) [α]: 6.95-7.55 (4H, m, protons on the aromatic compound); 5.45 (1H, s wide, proton on C-11); 3.7-3.82 (1H, m, proton on C-17); 3.4-3.6 (4H, m, protons of the ketalmethylene groups); 3.16 and 3.07

(each [1H, d with 15 Hz cleavage], A,B system of protons on C-19); 0.98 (3H, s, protons of a ketalmethyl group); 0.9 (3H, s, protons of a ketalmethyl group); 0.55 (3H, s, protons on C-18).

β)  11β,19-(o-phenylene)-3,3-(2,2-dimethyltrimethylenedioxy)-androstane-5α,17β-diol 2.5 g of the compound obtained in accordance with α) are dissolved in 250 ml of absolute toluene, mixed with 2.25 ml of tributyltin hydride and 250 mg of α,α-azoisobutyronitrile and heated for 3 hours under reflux. The solvent is then removed in vacuo, the residue taken up in tetrahydrofuran and stirred with 50 ml of saturated aqueous potassium-fluoride solution for one hour. The aqueous phase is then extracted with acetic ester and eliminated. The organic phases are combined, dried over sodium sulfate and concentrated in vacuo. The residue is chromatographed over aluminum oxide (neutral, stage III). This yields 1.75 g of the title compound.

The title compound indicated in b) can also be prepared from the following compound:

γ) 19-(2-fluorophenyl)-3,3-(2,2-dimethyltrimethylenedioxy)-9(11)-androstene-5α,17β-diol Analogous to Example 1a) 750 mg of 5α,10α-epoxy-3,3-(2,2-dimethyltrimethylenedioxy)-9(11)-estren-17β-ol are allowed to react with 2 g of 2-fluorobenzyl chloride. After chromatography this yields 798 mg of the above compound in the form of white foam.

$^1$H-NMR (CD$_2$Cl$_2$) [α]: 6.92–7.33 (4H, m, protons on the aromatic compound); 5.09 (1H, m, proton on C-11); 3.62–3.72 (1H, m, proton on C-17); 3.45–3.58 (4H, m, protons of the ketalmethylene groups); 2.97 and 2.9 (each [1H, d with 15 Hz cleavage], A,B system of protons on C-19); 0.99 (3H, s, protons of a ketalmethyl group); 0.9 (3H, s, protons of a ketalmethyl group); 0.61 (3H, s, protons on C-18).

δ11β,19-(o-phenylene)-3,3-(2,2-dimethyltrimethylenedioxy)-androstane-5α,17β-diol Analogous to Example 1b) 750 mg of 19-(2-fluorophenyl)-3,3-(2,2-dimethyltrimethylenedioxy)-9(11)-androstene-5α,17β-diol are allowed to react with 60 mg of lithium. After chromatography 585 mg of the above compound are isolated in the form of white foam.

c) 17β-hydroxy-11β,19-(o-phenylene)-4-androsten-3-one 2 g of the product obtained in accordance with b) are dissolved in 100 ml of acetone and mixed with 5 ml of 4n hydrochloric acid. After stirring for four hours at room temperature the reaction mixture is poured over saturated sodium hydrogen carbonate solution and the aqueous phase extracted with methylene chloride. The combined organic phases are dried with sodium sulfate and concentrated in vacuo- The residue is chromatographed over silica gel. This yields 1.13 g of the above compound. ps $[α]_D^{22} = +84°$ (CHCl$_3$; c=0.5)

$^1$H-NMR (CDCl$_3$) [α]: 7–7.5 (4H, m, protons on the aromatic compound); 5.88 (1H,s, proton on C-4); 3.68 (1H, d J=9 Hz, proton on C-17); 3.3 (1H, m, proton on C-11); 3.26 (1H d J=17 Hz, proton on C-19); 2.74 (1H, d J$_1$=17 Hz, proton on C-19); 0.29 (3H, s, protons on C-18)

Example 2

17β-hydroxy, 17-(prop-1-inyl)-11β,19-(o-phenylene)-4-androsten-3-one a) 11β,19-(o-phenylene)-5α-hydroxy-3,3-(2,2-dimethyltrimethylenedioxy)-androsten-17-one 11.28 g of chromium trioxide are added in portions to a mixture of 34.3 ml of pyridine and 287 ml of methylene chloride at 0° C. The steroid obtained in accordance with Example 1b) (8 g) is subsequently dissolved in 50 ml of methylene chloride, slowly added dropwise to the reaction mixture at the same temperature and the latter stirred for another two hours at the temperature of an ice bath. After the stirring is finished the solid constituents of the reaction are precipitated, the supernatant decanted and the precipitate washed out thoroughly several times with methylene chloride. The combined organic phases are liberated from remaining inorganic constituents by washing with an aqueous 0.5 m potassium-hydroxide solution, washed neutral with water, dried over sodium sulfate and concentrated in vacuo. 7 g of raw 11β,19-(o-phenylene)-5α-hydroxy-3,3-(2,2-dimethyltrimethylenedioxy)-androstan-17-one are isolated, the purity of which is suitable for further reactions (see below). 500 mg are purified for analytical purposes by chromatography over aluminum oxide (neutral, stage III). 432 mg of the desired product are isolated.

$[α]_D^{22} = +31°$ (CHCl$_3$; c=0.505)

Fp.:=206°–210° C. (ethylacetate)

b) 17-(prop-1-inyl)-11β,19-(o-phenylene)-3,3-(2,2-dimethyltrimethylenedioxy)-androstane-5α,17β-diol 225 ml of abs. tetrahydrofuran are saturated with propine at 0° C. 1.6 m of n-butyllithium solution (hexane) (27.7 ml) is subsequently slowly added dropwise to this solution without significantly raising the temperature. After subsequent stirring for fifteen minutes a solution of 2 g of the raw product obtained in accordance with a), in 45 ml of abs. tetrahydrofuran, are slowly added dropwise to this reaction solution and subsequently stirred for 30 minutes. Afterwards the reaction mixture is poured into water, the aqueous phase extracted with acetic ester and the combined organic phases washed with a solution of sodium chloride. Drying over sodium sulfate and concentration in vacuo yield 2.44 g of the raw product. Chromatography over aluminum oxide (neutral, stage III) yields 1.8 g of the above compound.

IR(KBr): 2230 cm$^{-1}$ triple bond c) 17β-hydroxy-17-(prop-1-inyl)-11β,19- (o-phenylene)-4-androsten-3-one Analogous to the acid cleavage described in Example 1c) 1.5 g of the product obtained in accordance with b) are converted to yield 738 mg of the title compound.

Example 3

17β-hydroxy-17-(prop-1-inyl)-11β,19-(o-phenylene)-4,6-androstadien-3-one a) 11β,19-(o-phenylene)-4-androstene-3,17-dione 20 g of the product obtained by the reaction steps in Example 1a), Example 1b) and Example 2a) are separated analogous to the specification in Example 1c) forming 8.69 g of the title compound.

$[\alpha]_D^{22} = +116°$ (CHCl$_3$; c=0.51)

Fp.:=284°-288° C.

b) 11β,19-(o-phenylene)-3-ethoxy-3,5-androstadien-17-one 8 g of the product obtained in accordance with a) are placed in a mixture of 85 ml of abs. methylene chloride, 25 ml of ethanol and 6.7 ml of triethyl orthoformate and mixed with 170 mg of p-toluene sulfonic acid (monohydrate) at 0° C. The mixture is subsequently stirred overnight at the temperature of an ice bath, then mixed with a surplus of sodium-hydrogen-carbonate solution and the aqueous phase extracted with methylene chloride. The combined organic phases are washed with a saturated solution of sodium chloride, dried over sodium sulfate and concentrated in vacuo. This yields 11.3 g of impure raw product. Crystallization from ethanol (mixed with a few drops of pyridine) yields 5.43 g of the title compound in crystalline form.

Fp.:=182°-186° C.

$[\alpha]_D^{22} = +39°$ (CHCl$_3$; c=0.5)

c) 17-(prop-1-inyl)-11β,19-(o-phenylene)-3-ethoxy-3,5-androstadien-17β-ol 5 g of the raw product obtained in accordance with b) are converted analogous to Example 2b) to form 5.4 g of the raw product, the purity of which is sufficient for further reactions. Crystallization of 400 mg of the raw product from ethanol yields 268 mg of the title compound in crystalline form.

Fp.:= +203°-207° C.

$[\alpha]_D^{22} = -91°$ (CHCl$_3$; c=0.5 )

d) 17-(prop-1-inyl)-17β-hydroxy-11β,19-(o-phenylene)-4,6-androstadien-3-one 5 g of the raw product obtained in accordance with c) are suspended in a mixture of 50 ml of 80% aqueous dioxane solution and 24 ml of 10% aqueous sodium acetate solution. 1.6 g of 1,3-dibromo-5,5-dimethylhydantoin are added to this suspension in portions at 0° C., the steroid slowly going into solution. After two hours of reaction the reaction mixture is poured into water and the aqueous phase extracted with methylene chloride. The combined organic phases are washed with a saturated solution of sodium thiosulfate and water, dried over sodium sulfate and concentrated in vacuo. The impure 17 -(prop-1- inyl)- 17β-hydroxy -11β19-(o-phenylene)-6β-bromo-4-androsten-3-one thereby obtained is dissolved in 48 ml of abs. dimethylformamide, mixed with 2.4 g of lithium bromide and 1.65 g of lithium carbonate under inert gas and stirred for one hour at 100° C. After the reaction mixture has cooled down to room temperature it is poured into water, the aqueous phase neutralized with 4n hydrochloric acid, cooled to the temperature of an ice bath, subsequently stirred for one hour at this temperature and the precipitated steroid sucked off. This yields 4.14 g of slightly impure raw product, the purity of which is adequate for further reactions. Starting with 1.14 g of the raw product, crystallization from diisopropyl ether yields 638 mg of the above compound.

$[\alpha]_D = +80°$ (CHCl$_3$; c=0.5)

Fp.:=215°-217 ° C.

Example 4

17-(prop-1-inyl)-17β-hydroxy-11β,19-(4-methoxy-o-phenylene)-4-androsten-3-one a) 19-(2-chloro-5-methoxyphenyl)-3,3-(2,2-dimethyl-trimethylenedioxy)-9(11)-androstene-5α,17β-diol Analogous to the specification in Example 1a) 15.5 g of the above compound are obtained when 15 g of 5α,1-0α-epoxy-3,3(2,2-dimethyltrimethylenedioxy)-9(11)-estren-17β-ol are allowed to react with 2-chloro-5-methoxybenzyl chloride.

b) 11β,-19-(4-methoxy-o-phenylene)-3,3-(2,2-dimethyl-trimethylenedioxy)-androstane-5α,17β-diol Analogous to the specification in Example 1b) 15 g of the compound obtained in accordance with a) yield 11.6 g of the title compound in the form of white foam.

$[\alpha]_D^{22} = +21.1°$ (CHCl$_3$; c=0.52)

Fp.:=223°-224 ° C. (diisopropyl ether)

The title compound b) can also be produced by way of the following synthesis.

α) 19-(2-bromo-5-methoxyphenyl)-3,3-(2,2-dimethyl-trimethylenedioxy)-9(11)-androstene-5α,17β-diol 150 g of 2-bromo-5-methoxy-benzyl bromide are suspended in 1 liter of abs. diethyl ether under inert gas and mixed with 13.3 g of magnesium chips. After Grignard's reaction has begun the reaction temperature is held beneath 30 ° C. by cooling. After complete formation of Grignard's reagent 50 g of 5α,10α-epoxy-3,3-(2,2-dimethyltrimethylenedioxy)-9(11)-estrene-5α,17β-diol dissolved in 330 ml of abs. tetrahydrofuran are added dropwise while stirring. The reaction mixture is subseqently stirred for 1.5 h and processed as described in Example 1a). After chromatography 66.5 g of the above compound are obtained in the form of white foam.

Fp.: 128°-130° C. (diisopropyl ether/hexane)

11β,19-(4-methoxy-o-phenylene)-3,3-(2,2-dimethyl-trimethylenedioxy)-androstane-5α,17β-diol Analogous to Example 1β) 66 g of 19-(2-bromo-5-methoxyphenyl)-3,3-(2,2-dimethyltrimethylenedioxy)-9(11)-androstene-5α,17β-diol in 1.7 l of absolute toluene are allowed to react with 34 ml of tributyltin hydride by using 660 mg of 2,2-azoisobutyric acid nitrile as the radical starter. After complete reaction the solvent is drawn off in vacuo and the residue crystallized from the diisopropyl ether. This yields 49 g of the above compound in crystalline form.

c) 11β,-19-(4-methoxy-o-phenylene)-5α-hydroxy-3,3-(2,2-dimethyl trimethylenedioxy)-androstan-17-one Analogous to Example 2a) 11 g of the compound obtained in accordance with b) are converted into the corresponding keto compound. This yields 9.53 g of the above compound in the form of white foam.

$[\alpha]_D^{22} = +33°$ (CHCl$_3$, c=0.55)

Fp.:=235°-238 ° C.

d) 17-(prop-1-inyl)-11β,19-(4-methoxy-o-phenylene)-3,3-(2,2-dimethyltrimethylenedioxy)-androstane-5α,17β-diol Analogous to Example 2b) 4 g of the compound obtained in accordance with c) are converted into the corresponding 17α-propinyl compound. After chromatography 3.3 g of the above compound are isolated in the form of white foam.

IR (KBr): 2230 cm$^{-1}$ triple bond e) 17-(prop-1-inyl)-17β-hydroxy-11β,19-(4-methoxy-o-phenylene)-4-androsten-3-one Analogous to Example 1c) 3g of the compound obtained in accordance with d) are converted into the corresponding 4-ene-keto compound. 1.5 g of the title compound are isolated in the form of white foam.

$[\alpha]_D^{22} = +18°$ (CHCl$_3$; c=0.465)

Example 5

17-(3-hydroxyprop-1-(Z)-enyl)-17βhydroxy-11β,19-(4-methoxy-o-phenylene)-4-androsten-3-one a) 17-[3-(tetrahydropyran-2-yloxy)-prop-1-inyl]-11β,19-(4-methoxy-o-phenylene)-3,3 -(2,2 -dimethyltrimethylenedioxy)-androstane-5α,17β-diol 28.3 ml of a 15% solution of n-butyllithium in hexane are slowly added dropwise to a solution of 5.7 g of 3-(tetrahydropyran-2-yloxy)-prop-1-ine in 100 ml of abs. tetrahydrofuran under inert gas at 0° C. The mixture is subsequently stirred for 15 minutes at 0 ° C., and then a solution containing 4 g of the product obtained in accordance with Example 4c) in 60 ml of abs. tetrahydrofuran is added dropwise at 0° to +5° C. The mixture is subsequently stirred for 3 hours at room temperature, then poured into ice water and extracted with acetic ester. After drying of the organic phase over sodium sulfate and concentration in vacuo the raw product is chromatographed over aluminum oxide (neutral, stage III). This yields 4.36 g of the above compound in the form of white foam.

Fp.:=150°-153° C. (diisopropyl ether) [as a 1:1 mixture of epimers as regards the tetrahydropyranyl ether]

b) 17-[3-(terahydropyran-2-yloxy)-prop-1(Z)-enyl]-11β,19-(4-methoxy-o-phenylene)-3,3-(2,2-dimethyl-trimethylenedioxy)-androstane-5α,17β-diol A solution of 4 g of the product obtained in accordance with a) is hydrogenated in 75 ml of tetrahydrofuran after the addition of 5 ml of pyridine and 400 mg of palladium/barium sulfate (10% Pd) at room temperature and normal pressure. When no more water is taken up the mixture is filtered off from the catalyst and the filtrate concentrated. This yields 3.91 g of the above compound in the form of a yellowish foam.

c) 17-[3-hydroxyprop-1(Z)-enyl]-17β-hydroxy-11β,19-(4-methoxy-o-phenylene)-4-androsten-3-one Analogous to Example 1c) 3.5 g of the compound obtained in accordance with b) are cleaved. This yields 1.5 g of the title compound in the form of white foam.

$[\alpha]_D^{22} = +60°$ (CHCl$_3$, c=0.5)

Example 6

17-(cyanomethyl)-17β-hydroxy-11β,19 -(4 methoxy-o-phenylene)-4-androsten-3-one a) 11β,19-(4-methoxy-o-phenylene)-3,3-(2,2- dimethyltrimethylenedioxy)-androstan-[17(β-1')-spiro-3']-oxiran-5α-ol 1 g of the ketone obtained in accordance with specification 4c) is dissolved in 20 ml of absolute dimethylformamide under inert gas and mixed at 0° C. first with 2.04 g of trimethylsulfonium iodide and then 1.40 g of potassium tert.-butylate. The reaction mixture is subsequently heated slowly to room temperature overnight with constant stirring, then poured into a saturated solution of ammonium chloride and the aqueous phase extracted several times with acetic ester. The combined organic phases are dried over sodium sulfate, concentrated in vacuo and the residue chromatographed over aluminum oxide (neutral, stage III). 895 mg of the above compound are isolated in the form of white foam.

b) 17-cyanomethyl-11β,19-(4-methoxy-o-phenylene)-3,3-(2,2 - dimethyltrimethylenedioxy)-androstane-5α,17β-diol 850 mg of the epoxide obtained in accordance with a) are dissolved in 17 ml of absolute ethanol under inert gas and mixed with a solution of 1.7 g of potassium cyanide in 3.4 ml of water. The reaction mixture is subsequently heated to 50° C. overnight, then poured into ice water and the aqueous phase extracted several times with acetic ester. The combined organic phases are dried over sodium sulfate and concentrated in vacuo until dry. The residue is chromatographed over aluminum oxide (neutral, stage III). 815 mg of the above compound are isolated.

IR (KBr): 2250 cm$^{-1}$ C≡N triple bond c) 17-cyanomethyl-17β-hydroxy-11β,19-(4 methoxy-o-phenylene)-4-androsten-3-one 800 mg of the compound obtained in accordance with b) are converted into the corresponding 4-ene-3-keto compound analogous to Example 1c). 575 mg of the title compound are isolated.

$[\alpha]_D^{22} = 59°$ (CHCl$_3$; c=0.505)

Fp.:=155°-156° C. (acetic ester/hexane)

Example 7

17- (prop-1-inyl) -17β-hydroxy-11β,19-(4-methoxy-o-phenylene)-4,6-androstadien-3-one a) 11β,19-(4-methoxy-o-phenylene)-4-androstene-3,17-dione Analogous to Example 1c) 11.2 g of the substance obtained by specification c) in Example 4 are converted to form the corresponding 4-ene-3-keto compound. 7.6 g of the above compound are isolated.

$[\alpha]_D^{22} = 130°$ (CHCl$_3$; c=0.5)

Fp.:=184°-187° C. (acetic ester)

b) 11β,19-(4-methoxy-o-phenylene)-3-ethoxy-3,5,-androstadien-17-one

Analogous to Example 3b) 5 g of the substance obtained in accordance with a) are allowed to react with ethanol. 2.45 g of the title compound are yielded in crystalline form.

$[\alpha]_D^{22} = 57°$ (CHCl$_3$; c=0.5)

Fp.:=174°-176 ° C.

c) 17-(prop-1-inyl)-11β,19-(4-methoxy-o-phenylene)-3-ethoxy-3,5-androstadien-17β-ol Analogous to Example 3 c) 2.4 g of the keto compound obtained in accordance with b) are converted. 2.45 g of the raw product are isolated.

$[\alpha]_D^{22} = +86°$(CHCl$_3$; c=0.505 )

Fp.=168°-171° C. (ethanol)

d) 17-(prop-1-inyl)-17β-hydroxy-11β,19-(4-methoxy-o-phenylene)-4,6-androstadien-3-one Analogous to Example 3d) 2.35 g of the raw product obtained in accordance with c) are converted to form the corresponding 4,6-diene-3-keto compound. Chromatography over silica gel yields 1.43 g of the title compound.

$[\alpha]_D^{22} = 132°$ (CHCl$_3$; c=0.5)

Fp.:=237°-242° C. (acetic ester)

Example 8

17-(3-hydroxyprop-1(Z)-enyl)-17β-hydroxy-11β,19-(4-methylthio-o-phenylene)-4-androsten-3-one a) 19-(2-chloro-5-methylthiophenyl)-3,3-(2,2-dimethyl-trimethylene-dioxy)-9(11)-androstene-5α,17β8-diol Analogous to Example 1 a), an amount of 34 g of 5α,10α-epoxy-3,3-(2,2-dimethyltrimethylenedioxy)-9(11)-androsten-17β-ol is allowed to react with. 94.5 g of 2-chloro-5-methylthiobenzyl chloride. After chromatography an amount of 43.2 g of the above compound is obtained as white foam.

b) 11β,19-(4-methylthio-o-phenylene)-3,3-(2,2-dimethyltrimethylenedioxy)-androstane-5α,17β-diol 40 g of the substance obtained in accordance with a) is dissolved in 750 ml of absolute tetrahydrofuran and added dropwise at −78C.° to a mixture of 3.79 g of lithium and 3.4 l of liquid ammonia. After 45 minutes of stirring, a mixture of 200 ml of methanol, 200 ml of tetrahydofuran and 4.6 ml of methyl iodide is added slowly drop by drop at the same temperature. After completion of this addition the mixture is treated in a manner analogous to Example 1b). From the crude product, 18.37 g of the pure title compound is crystallized out.

Fp.=173°-176°C. (acetic ester)

c) 11β,19-(4-methylthio-o-phenylene)-5α(-hydroxy-3,3-(2,2-dimethyltrimethylenedioxy)-androstan-17-one Analogous to Example 13c), an amount of 18 g of the compound obtained in accordance with b) is allowed to react with 21.47 g of aluminum triisopropylate and 156 ml of cyclohexanone in 780 ml of absolute toluene to form the corresponding 17-keto compound. After chromatography over aluminum oxide (neutral, stage III), an amount of 13.98 g of the above compound is obtained as white foam.

$[\alpha]_D^{22} = 41.8°$ (CHCl$_3$; c=0.5)

Fp.=224°-225° C. (acetic ester/hexane)

d) 17-[3-(tetrahydropyran-2-yloxy)-prop-1-inyl]-11β,19-(4-methylthio-o-phenylene)-3,3-(2,2-dimethyltrimethylenedioxy)-androstane-5α,17β-diol Analogous to example 5 a), 13.8 g of the substance obtained in accordance with c) is allowed to react with 19 g of 3-(tetra-hydropyran-2-yloxy)-prop-1-ine. After chromatography an amount of 15.65 g of the above compound is isolated as white foam.

IR (KBr): 2230 cm$^{-1}$ triple bond e) 17-[3-(tetrahydropyran-2-yloxy)-prop-1(Z)-enyl]-11β,19-(4-methylthio-o-phenylene)-3,3-(2,2-dimethyltrimethylenedioxyoxy)-androstane-5α,17β-diol Analogous to Example 5 b), 15.5 g of the substance obtained in accordance with d) is hydrogenated with hydrogen using 1.51 g of palladium on barium sulfate (10% Pd), poisoned with 18.9 ml of pyridine, as a catalyst. After chromatography an amount of 14.15 g of the title compound is isolated as white foam.

f) 17-(3-hydroxyprop-1(Z)-enyl)-17β-hydroxy-11β,19-(4-methylthio-o-phenylene)-4-androsten-3-one 5.5 g of the olefin obtained in accordance with e) are allowed to react in a manner similar to Example 1 c with 5 ml of 4 n aqueous hydrochloric acid in 200 ml of acetone to form the 4-ene-3-keto compound- After chromatography over silica gel, an amount of 2.34 g of the title compound is isolated as white foam.

$[\alpha]_D^{22} = 86°$ (CHCl$_3$); c=0.51)

Fp.=146°-148° C. (acetic ester/hexane)

Example 9

17-(3-hydroxyprop-1(Z)-enyl)-5α,17β-dihydroxy-11β,19-(4-methylthio-o-phenylene)-androstan-3 -one a) 17-(3-hydroxyprop-1(Z)-enyl)-5α,17β-dihydroxy-11β,19-(4-methylthio-o-phenylene)-androstan-3-one 5 g of the substance obtained in accordance with Example 8 e) is converted in 50 ml of 70% acetic acid at room temperature to the required 3-keto compound. The reaction mixture is subsequently diluted with water and the aqueous phase is extracted with methylene chloride. The united organic phases are washed in sequence with saturated sodium hydrogen sulfate and saturated common salt solution, subsequently being dried over sodium sulfate. After evaporation of the solvents in vacuo, the residue is chromatographed over silica gel and 2.66 g of the above compound is isolated as white foam.

$[\alpha]_D^{22} = -5°$ (CHCl$_3$); c=0.5)

Fp.=193°-195° C. (acetic ester)

Example 10

17-(3-hydroxyprop-1(Z)-enyl)-17β-hydroxy-11β,19-(4-methylsulfenyl-o-phenylene)-4-androsten-3-one a) 17-[3-(tetrahydropyran-2-yloxy)-prop-1(Z)-enyl]-11β,19-(4-methylsulfinyl-o-phenylene)-3,3-(2,2-dimethyltrimethylenedioxy)-androstane-5α,17β-diol 5 g of the substance obtained in accordance with Example 8e) is dissolved in a mixture of 45 ml of tetrahydrofuran, 45 ml of methanol and 10 ml of water and treated with 5.1 g of sodium periodate. The reaction mixture is stirred overnight at room temperture, filtered over Celite and the filtrate diluted with acetic ester. The organic phase is washed with saturated sodium hydrogen sulfate solution, dried over sodium sulfate and concentrated in vacuo. The residue is chromatographed over aluminum oxide (neutral, stage III). 3.94 g of the above compound is obtained as white foam.

b) 17-(3-hydroxyprop-1(Z)-enyl)-17β-hydroxy-11β,19-(4-methylsulfenyl-o-phenylene)-4-androsten-3-one Analogous to Example 1 c), 3.8 g pf the substance obtained in accordance with a) is converted to the 4-ene-3-keto compound. After chromatography over silica gel, an amount of 1.66 g of the title compound is isolated.

$[\alpha]_D^{22} = 51°$ (CHCl$_3$; c=0.5)

Example 11

17-(3-hydroxyprop-1-inyl)-17β-hydroxy-11β,19-(4-methylthio-o-phenylene)-4-androsten-3-one a) 17-(3-hydroxyprop-1-inyl)-17β-hydroxy-11β,19-(4-methylthio-o-phenylene)-4-androsten-3-one Analogous to Example 1 c), 2.5 g of the substance obtained in accordance with Example 8 d) is split to form the corresponding 4-ene-3-keto compound. After chromatography over silica gel, an amount of 1.13 g of the title compound is isolated as white foam.

Example 12

17-(3-hydroxyprop-1(Z)-enyl)-17β-hydroxy-11β,19-(4-ethylthio-o-phenylene)-4-androsten-3-one a) 11β,19-(4-ethylthio-o-phenylene)-3,3-(2,2-dimethyltrimethylenedioxy)-androstane-5α,17β-diol Analogous to Example 8b), 10 g of the substance produced in accordance with Example 8a) are allowed to react with 620 mg of lithium and 14.7 ml of ethyl iodide instead of methyl iodide. From the crude product, an amount of 4.62 g of the above-mentioned compound is obtained as a crystalline product from acetic ester|hexane.

$[\alpha]_D^{22} = 39°$ (CHCL$_3$; c=0.5)

Fp.=164° C.

11β,19-(4-ethylthio-o-phenylene)-5α-hydroxy-3,3-(2,2-dimethyltrimethylenedioxy)-androstan-17-one Analogous to Example 13 c), 4.5 g of the substance produced in accordance with a) is converted into the corresponding 17-keto compound. After chromatography, an amount of 3.4 g of the above-mentioned compound is isolated.

$[\alpha]_D^{22} = 44°$ (CHCl$_3$; c=0.505);

IR (KBr): 1740 cm$^{-1}$ pentacyclic ketone c) 17-[3-(tetrahydropyran-2-yloxy)-prop-1-inyl]-11β,19-(4-ethylthio-o-phenylene)-3,3-(2,2-dimethyltrimethylenedioxy)-androstane-5α,17β-diol Analogous to Example 5 a), an amount of 3.2 g of the ketone produced in accordance with b) is allowed to react with 4.31 g of 3-(tetrahydropyran-2-yloxy)-prop-1-ine. After chromatography, an amount of 3.25 g of the above-mentioned compound is isolated as white foam.

IR (KBr): 2230 cm$^{-1}$ triple bond d) 17-[3-(tetrahydropyran-2-yloxy)-prop-1(Z)-enyl]-11β,19-(4-ethylthio-o-phenylene)-3,3-(2,2-dimethyltrimethylenedioxy)-androstane-5α,17β-diol Analogous to Example 5 b), an amount of 3.1 g of the substance obtained in accordance with c) is hydrogenated with 300 mg of palladium on barium sulfate (10% Pd), poisoned with 3.75 ml of pyridine, as a catalyst. After chromatography, an amount of 2.85 g of the title compound is isolated as white foam.

e) 17-(3-hydroxyprop-1(Z)-enyl)-17β-hydroxy-11β,19-(4-ethylthio-o-phenylene)-4-androsten-3-one 2.7 g of the olefin obtained in accordance with d) is converted in a manner analogous to Example 1 c) with 2.5 ml of 4 n aqueous hydrochloric acid in 100 ml of acetone to the corresponding 4-ene-3-keto compound. After chromatography over silica gel, an amount of 1.35 g of the above compound is isolated as yellowish foam.

$[\alpha]_D^{22} = 85°$ (CHCl$_3$; c=0.5).

Example 13

17-(prop-1-inyl)-17β-hydroxy-11β,19-(4-dimethylamino-o-phenylene)-4-androsten-3-one a) 19-(2-chloro-5-dimethylaminophenyl)-3,3-(2,2-dimethyltrimethylenedioxy)-9(11)-androstene-5α,17β-diol Analogous to Example 1a), an amount of 14.39 g of the above-mentioned compound was obtained starting from 15 g of 5α,10α-epoxy-3,3-(2,2-dimethyltrimethylenedioxy)-9(11)-estrene-17β-ol by reaction with 2-chloro-5-dimethylaminobenzyl chloride.

b) 11β,19-(4-dimethylamino-o-phenylene)-3,3-(2,2-dimethyltrimethylenedioxy)-androstane-5α,17β-diol Analogous to Example 1 b), an amount of 9.9 g of the above-mentioned compound is obtained as white foam starting from 14 g of the compound obtained in accordance with a).

c) 11β,19-(4-dimethylamino-o-phenylene)-5α-hydroxy-3,3-(2,2-dimethyltrimethylenedioxy)-androstan-17-one 11.5 g of the compound produced in accordance with b) is dissolved in 500 ml of toluene and treated in sequence with 13.8 g of aluminum triisopropylate and 100 ml of cyclohexanone. Thereafter the reaction mixture is heated under reflux and approximately one third of the solvent is distilled off. After cooling the mixture is poured into ice water, the emulsion arising is filtered over Celite, the filter residue is washed thoroughly with ethyl acetate, the organic phase of the filtrate is separated and dried over sodium sulfate and concentrated in vacuo. After chromatography of the residue over aluminum oxide (neutral, stage III), an amount of 8.13 g of the title compound is obtained.

Crystallization of 130 mg of this compound from acetic ester yields 67 mg of crystalline 11β,19-(4-dimethylamino-o-phenylene)-5α-hydroxy-3,3-(2,2-dimethyltrimethylenedioxy)-androstan-17-one.

Fp.=264°-267° C.

$[\alpha]_D^{22} = 28°$ (CHCL$_3$; c=0.5)

d) 17-(prop-1-inyl)-11β,19-(4-dimethylamino-o-phenylene)-3,3-(2,2-dimethyltrimethylenedioxy)-androstane-5α,17β-diol Analogous to Example 2b), 3 g of the compound obtained in accordance with c) is converted to the corresponding 17α-propinyl compound. After chromatography, an amount of 2.6 g of the above-mentioned compound is isolated as yellowish foam.

IR (KBr): 2235 cm$^{-1}$ triple bond e) 17-(prop-1-inyl)-17β-hydroxy-11β,19-(4-dimethylamino-o-phenylene)-4-androsten-3-one Analogous to Example 1c), an amount of 2.5 g of the product obtained in accordance with d) is converted into the corresponding 4-ene-3-keto compound. An amount of 1.58 g of the above-mentioned compound is isolated as white foam.

$[\alpha]_D^{22} = +28°$ (CHCl$_3$; c=0.51)

Fp.=231°-234° C. (ethyl acetate)

The 2-chloro-5-dimethylaminobenzyl chloride required for reaction stage 7a) is produced in the following way:

α) 2-chloro-5-dimethylaminobenzyl chloride

Under an inert atmosphere, 300 g of lithium aluminum hydride is provided in 3 l of tetrahydrofuran at 0° C. and treated in portions with 500 g of 5-amino-2-chlorobenzoic acid (industrial, 85%). Thereafter the reaction mixture is heated slowly to room temperature and stirred over night at this temperature. For further processing the reaction mixture is cooled to 0° C. and the excessive lithium aluminum hydride is carefuly decomposed with saturated ammonium chloride solution. Thereafter the organic phase is separated from the deposit and this deposit is washed several times with acetic ester and methylene chloride. The united organic phases are washed neutral with saturated sodium chloride solution, dried over sodium sulfate and concentrated in vacuo. A yield of 242 g of crude 2-chloro-5-aminobenzyl alcohol is obtained the purity of which is adequate for subsequent reactions.

$^1$H-NMR (CDCl$_3$) [δ]: 6.3–7.15 (3H, m, aromatic protons); 4.55 (2H, s, benzylic protons)

β) 2-chloro-5-dimethylaminobenzyl alcohol

An amount of 51.8 g of sodium borohydride suspended in a mixture of 30 g of 2-chloro-5-aminobenzyl alcohol and 1 liter of tetrahydrofuran is added dropwise under cooling to a stirred mixture of 235 ml of 2 m sulfuric acid and 88 ml of a 38% solution of formalin in such a way that the temperature remains between −10° C. and 20° C. After completion of this addition, the reaction mixture is made markedly alkaline with solid sodium hydroxide and treated with water. The organic phase is separated off, the aqueous phase extracted several times with methylene chloride and the united organic phases are washed neutral with saturated sodium chloride solution. Thereafter they are dried over sodium sulfate and concentrated in vacuo. A yield of 24 g of 2-chloro-5-dimethylaminobenzyl alcohol is obtained as an oil.

$^1$H-NMR (CDCl$_3$) [δ]: 6.4–7.25 (3H, m, aromatic protons); 4.67 (3H, s, benzylic protons); 2.92 (6H, s, protons of the two methyl groups).

γ) 2-chloro-5-dimethylaminobenzyl chloride 23.8 g of N-chlorosuccinimide provided in 600 ml of absolute methylene chloride is cooled to 0° C. and is slowly mixed with 15.6 ml of dimethyl sulfide. Thereafter the suspension thus produced is cooled to −30° C. and carefully mixed with 20 g of 2-chloro-5-dimethylaminobenzyl alcohol. The reaction mixture is then warmed to 0° C. and stirred at this temperature for 3 hours. Thereafter the mixture is diluted with methylene chloride and poured into ice water. The organic phase is separated, washed with saturated sodium chloride solution, dried over sodium sulfate solution and concentrated in vacuo. The residue is chromatographed with hexane over aluminum oxide (neutral, stage III). A yield of 17.2 g of 2-chloro-5-dimethylaminobenzyl chloride is obtained.

$^1$H-NMR (CDCl$_3$) [δ]: 6.4–7.3 (3H, m, aromatic protons); 4.61 (2H, s, benzylic protons); 2.92 (6H, s, protons of the two methyl groups).

Example 14

17β-hydroxy-17-methoxymethyl-11β,19-(4-dimethylamino-o-phenylene)-4-androsten-3-one a) 11β,19-(4-dimethylamino-o-phenylene)-3,3-(2,2-dimethyltrimethylenedioxy)-androstane-|17(β-1')-spiro-3'|-oxiran-5-ol 2.5 g of the compound prepared in accordance with Example 13 c) is dissolved in an inert atmosphere in 50 ml of abs. dimethyl formamide and cooled to 0° C. This solution is treated in sequence with 5 g of trimethylsulfonium iodide and 3.4 g of potassium tert.-butylate. The reaction mixture is stirred until the reaction is completely finished (DC check). Thereafter the reaction mixture is poured into ice water, the aqueous phase is extracted with acetic ester, the organic phase is washed with sodium chloride solution and dried over sodium sulfate. After evaporation of the solvents, the residue is chromatographed over aluminum oxide (neutral, stage III), an amount of 2.1 g of the above-mentioned compound is isolated as white foam.

17-methoxymethyl-11β,19-(4-dimethylamino-o-phenylene)-3,3-(2,2-dimethyltrimethylenedioxy)-androstane-5-17β-diol 2 g of the compound prepared in accordance with a) is dissolved in 40 ml of 3 m methanolic.sodium methylate solution and then heated under reflux in an inert atmosphere for 5 hours. After cooling, the reaction mixture is poured into ice water, the aqueous phase is extracted with methylene chloride and the organic phase is washed with sodium chloride solution. After drying of the organic phase over sodium sulfate, concentration in vacuo and chromatography of the residue over aluminum hydroxide (neutral. stage III), an amount of 1.41 g of the above-mentioned compound is isolated as white foam.

c) 17β-hydroxy-17-methoxymethyl-11β,19-(4-dimethylamino-o-phenylene)-4-androsten-3-one Analogous to Example 1c), 1.3 g of the product obtained in accordance with b) is converted to the corresponding 4-ene-3-keto compound. An amount of 0.75 g of the title compound is isolated as white foam.

$[\alpha]_D^{22} = 80°$ (CHCl$_3$; c=0.505)

Fp.=124°-127° C.

Example 15

17-cyanomethyl-17β-hydroxy-11β,19-(4-dimethylamino-o-phenylene)-4-androsten-3-one a) 17-cyanomethyl-11β,19-(4-dimethylamino-o-phenylene)-3,3-(2,2-dimethyltrimethylenedioxy)-androstane-5α,17β-diol Analogous to Example 6 b), 2.2 g of the epoxide prepared in accordance with Example 14 a) is allowed to react in 42 ml of ethanol with a solution of 4.22 g of potassium cyanide in 8.4 ml of water. After chromatograpy, an amount of 1.95 g of the above-mentioned compound is isolated.

IR (KBr): 2245 cm$^{-1}$ C≡N triple bond b) 17-cyanomethyl-17β-hydroxy-11β,19-(4-dimethylamino-o-phenylene)-4-androsten-3-one Analogous to Example 1 c), an amount of 1.9 g of the cyanide obtained in accordance with a) is converted into the corresponding 4-ene-3-keto compound. From the crude product an amount of 1.23 g of the title compound is crystallized directly. Chromatography of the mother liquor leads to a further 138 mg of the required cyano compound.

$[\alpha]_D^{22} = 77°$ (CHCl$_3$; c=0.5)

Fp.=172°-176° C.

Example 16

17-(3-hydroxyprop-1-inyl)-17β-hydroxy-11β,19-(4-dimethylamino-o-phenylene)-4-androsten-3-one a) 17-[3-(tetrahydropyran-2-yloxy)-prop-1-inyl]-11β,19-(4-dimethylamine-o-phenylene)-3,3-(2,2-dimethyltrimethylene dioxy)-androstane-5α-17β-diol Analogous to Example 5 a), 10 g of the keto compound prepared in accordance with Example 13 c) is allowed to react with 55.3 g of 3-(tetrahydropyran-2-yloxy)-propine and 247 ml of a 15% solution of n-butyllithium in hexane. After chromatography 11.74 g of the above-mentioned compound is obtained as white foam.

IR (KBr): 2230 cm$^{-1}$ triple bond b) 17-(3-hydroxyprop-1-inyl)-17β-hydroxy-11β,19-(4-dimethylamino-o-phenylene)-4-androsten-3-one Analogous to Example 1 c), 11.74 g of the compound prepared in accordance with a) is converted into 6.97 g of the title compound.

$[\alpha]_D^{22} = 25.6°$ (CHCl$_3$; c=0.5)

Fp.=251°-253° C. (acetic ester)

Example 17

17-(3-hydroxyprop-1(Z)-enyl)-17β-hydroxy-11β,19-(4-dimethylamino-o-phenylene)-4-androsten-3-one a) 17-(3-hydroxyprop-1(Z)-enyl)-17β-hydroxy-11β,19-(4-dimethylamino-o-phenylene)-4-androsten-3-one Analogous to Example 5 b), an amount of 6.5 g of the acetylene compound prepared in accordance with Example 16 b) is converted to the corresponding Z-olefin. After chromatography over silica gel, an amount of 4.76 g of the above-mentioned title compound is isolated as white foam.

$[\alpha]_D^{22} = 71°$ (CHCl$_3$; c=0.5)

Example 18

17β-hydroxy-11β,19-(4-hydroxy-o-phenylene)-4-androsten-3-one a) 11β,19-(4-hydroxy-o-phenylene)-3,3-(2,2-dimethyltrimethylenedioxy)-androstane-5α,17β-diol 50 g of the methoxy compound obtained in a manner analogous to Example 4 a) is dissolved in 500 ml of absolute dimethyl formamide and then treated under an inert gas atmosphere with 28.2 g of sodium methanethiolate. Under this inert gas the reaction mixture is heated under reflux for 3 hours, cooled to room temperature and then poured into 8 l of ice water. The mixture is then stirred at room temperature until the crude product has precipitated as a solid substance. The product is then sucked off, washed with water and dried in vacuo. An amount of 49.2 g of the crude title compound is isolated as a white solid the quality of which is adequate for further reactions.

$[\alpha]_D^{22} = 21°$ (CHCl$_3$; c=0.5)

Fp.=267°-270° C. (acetic ester)

b) 17β-hydroxy-11β,19-(4-hydroxy-o-phenylene)-4-androsten-3-one 2 g of the phenol obtained in accordance with a) is converted into the 4-ene-3-keto compound in a manner analogous to Example 1 c) with 3 ml of 4 n aqueous hydrochloric acid in 60 ml of acetone. An amount of 1.05 g of the above-mentioned compound is isolated as white foam.

Fp.=242°-245° C. (acetic ester)

Example 19

17β-hydroxy-11β,19-(4-trifluoromethyl-sulfonyloxy-o-phenylene)-4-androsten-3-one a) 17β-hydroxy-11β,19-(4-trifluoro-methyl-sulfonyloxy-o-phenylene)-4-androsten-3-one 10 g of the phenol prepared in a manner analogous to Example 18 b) is dissolved in 250 ml of absolute methylene chloride and treated with 17.3 g of 4-dimethylamino-pyridine. In an inert atmopsphere, the solution is then cooled to −50° C. and treated by slowly adding dropwise 4.76 ml of trifluoromethane sulfonic acid anhydride dissolved in 30 ml of absolute methylene chloride. After 15 minutes of stirring at −50° C. the reaction mixture is poured into saturated sodium bicarbonate solution and the aqueous phase is extracted with methylene chloride. The united organic phases are washed with saturated sodium chloride solution, dried over sodium sulfate and concentrated under a vacum. After chromatography of the residue over silica gel, an amount of 11.37 g of the title compound is obtained as yellowish foam.

Fp.=204°-205° C. (diisopropyl ether)

Example 20

17β-hydroxy-11β,19-[4-(2-trimethyl-silyl-ethinyl)-o-phenylene]-4-androsten-3-one a) 17β-hydroxy-11β,19-[4-(2-trimethyl-silyl-ethinyl)-o-phenylene]-4-androsten-3-one 1 g of the triflate compound prepared in accordance with Example 19 a) is dissolved in 10 ml of absolute dimethyl formamide and treated under inert gas with triethylamine, 1.39 ml of trimethylsilyl acetylene and 49 mg of palladium tetrakistriphenyl phosphine. Therafter the reaction mixture is heated for 1 hour at 110° C., then cooled to room temperature and diluted with acetic ester. After filtration over Celite, the filtrate is washed several times with saturated sodium chloride solution, the organic phase separated, dried over sodium sulfate and concentrated in vacuo. Chromatography of the residue over silica gel yields 656 mg of the title compound as white foam.

Fp.=267°-271° C. (diisopropyl ether)

Example 21

17-(prop-1-inyl)-17β-hydroxy-11β,19-[4-(2-trimethyl-silylethiny)-o-phenylene]-4-androsten-3-one a) 11β,19-(4-trifluoromethyl-sulfonyloxy-o-phenylene)-3,3-(2,2-dimethyltrimethylenedioxy)-androstane-5α,17β-diol 40 g of the phenol prepared in accordance with Example 18a) is allowed to react with 14.93 ml of trifluoromethane sulfonic acid anhydride analogous to Example 19a). After chromatography, 37.3 g of the above compound is isolated as white foam.

b) 11β,19-[4-(2-trimethylsilylethinyl)-o-phenylene]-3,3-(2,2-dimethyltrimethylenedioxy)-androstane-5α,17β-diol 15 g of the compound prepared in accordance with Example 20a) is allowed to react with 17.3 ml of trimethylsilyl acetylene. After chromatography over aluminum oxide (neutral, stage III), an amount of 11.7 g of the above compound is isolated as white foam.

IR (KBr): 2150 cm$^{-1}$ triple bond in the aromate c) 11β,19-[4-(trimethylsilylethinyl)-o-phenylene]-5α-(-hydroxy-3,3-(2,2-dimethyltrimethylenedioxy)-androstan-17-one 11.2 g of the substance obtained in accordance with b) is oxidized in a manner analogous to Example 2 a) to the corresponding 17-keto compound with 11.69 g of chromium trioxide. Chromatography over aluminum oxide (neutral, stage III) yields 9.05 g of the above compound as white foam.

$[\alpha]_D^{22}=51°$ (CHCl$_3$; c=0.5)

Fp.=245°-248° C. (diisopropyl.ether)

d) 17-(prop-1-inyl)-11β,19-[4-(2-trimethylsilylethinyl)-o-phenylene]-3,3-(2,2-dimethyltrimethylene-dioxy)-androstane-5α,17β-diol 1 g of the ketone prepared in accordance with c) is treated with propine in a manner analogous to Example 2b). After chromatography over aluminum oxide (neutral, stage III), an amount of 956 mg is isolated as white foam.

IR (KBr): 2250 cm$^{-1}$ triple bond on the aromate
2235 cm$^{-1}$ triple bond e) 17-(prop-1-inyl)-17β-hydroxy-11β,19-[4-(2-trimethylsilylethinyl)-o-phenylene]-4-androsten-3-one 900 mg of the compound produced in accordance with d) is split analogous to Example 1 c) to form the corresponding 4-ene-3-keto compound. After chromatography over silica gel, an amount of 471 mg of the title compound is isolated as white foam.

$[\alpha]_D^{22}=59°$ (CHCl$_3$; c=0.505)

Example 22

17-(prop-1-inyl)-17β-hydroxy-11β,19-(4-ethinyl-o-phenylene)-4-androsten-3-one

11β,19-(4-ethinyl-o-phenylene)-5α-hydroxy-3,3-(2,2-dimethyltrimethylenedioxy)-androstan-17-one 1.5 g of the ketone produced in accordance with Example 21 c) is dissolved in 26 ml of absolute methanol and mixed with 1.1 g of water-free potassium carbonate. In an inert atmosphere the reaction mixture is stirred for 3 hours, then poured into saturated sodium chloride solution, the aqueous phase being extracted several times with methylene chloride. The united organic phases are washed with saturated sodium chloride solution, dried over sodium sulfate and concentrated in vacuo. The quality of the crude product (1.31 g) is adequate for further reactions. Chromatography of 100 mg of the crude product over aluminum oxide (neutral, stage III) yields 67 mg of the pure title compound as white foam.

b) 17-(prop-1-inyl)-11β,19-(4-ethinyl-o-phenylene)-3,3-(2,2-dimethyltrimethylenedioxy)-androstane-5α,17β-diol 1.2 g of the product obtained in accordance with a) is allowed to react with propine in a manner analogous to Example 2 b). After chromatography over aluminum oxide (neutral, stage III), an amount of 1.12 g of the above-mentioned compound is isolated as white foam.

IR (KBr): 2110 cm$^{-1}$ triple bond on the atomate
2235 cm$^{-1}$ triple bond c) 17-(prop-1-inyl)-17β-hydroxy-11β,19-(4-ethinyl-o-phenylene)-4-androsten-3-one 1.1 g of the substance prepared in accordance with b) is converted to the corresponding 4-ene-3-keto compound analogous to Example 1 c). After chromatography over silica gel, an amount of 612 mg of the title compound is isolated as white foam.

$[\alpha]_D^{22}=41°$ (CHCl$_3$; c=0.5)

Example 23

17-(prop-1-inyl)-17β-hydroxy-11β,19-[4-(2-trimethyl-silylethyl)-o-phenylene]-4-androsten-3-one a) 11β,19-[4-(2-trimethyl-silyl-ethyl)-o-phenylene]-5α-hydroxy-3,3-(2,2-dimethyltrimethylenedioxy)-androstan-17-one 1 g of the ketone prepared in accordance with Example 21 c) is dissolved in 10 ml of absolute ethanol and hydrogenated at normal pressure with 100 mg of palladium on carbon (10%) as a catalyst. After absorption of 2 equivalents of hydrogen, the reaction mixture is filtered under suction over Celite. The filter residue is washed with acetic ester and the filtrate is concentrated in vacuo. After chromatography of the residue over aluminum oxide (neutral, stage III), an amount of 884 mg of the above compound is isolated as white foam.

b) 17-(prop-1-inyl)-11β,19-[4-(2-trimethylsilylethyl)-o-phenylene]-3,3-(2,2-dimethyltrimethylenedioxy)-androstane-5α,17β-diol 850 mg of the ketone prepared in accordance with a) is allowed to react with propine in a manner analogous to Example 2 b). After chromatography over aluminum oxide (neutral, stage III), an amount of 845 mg of the above-mentioned compound is isolated as white foam.

IR (KBr): 2235 cm$^{-1}$ triple bond c) 17-(prop-1-inyl) -17β-hydroxy-11β,19-[4-(2-trimethylsilylethyl)-o-phenylene]-4-androsten-3-one 800 mg of the substance prepared in accordance with b) is converted into the corresponding 4-ene-3-keto compound by a sequence analogous to Example 1 c). After chromatography over silica gel, an amount of 512 mg of the above-mentioned compound is isolated as white foam.

$[\alpha]_D^{22} = 23°$ (CHCl$_3$; c=0.505)

Example 24

17-(prop-1-inyl) -17β-hydroxy-11β,19-(4ethyl-o-phenylene)-4470 -androsten-3-one a) 11β,19-(4-ethyl-o-phenylene)-5α-hydroxy-3,3-(2,2-dimethyltrimethylenedioxy)-androstan-17-one 4 g of the acetyl compound obtained in accordance with Example 22 a) is hydrogenated in a manner analogous to Example 23 a) to form the corresponding ethyl compound. After chromatography over aluminum oxide (neutral, stage III), an amount of 3.63 g of the above compound is isolated as white foam.

b) 17-(prop-1-inyl)-11β,19-(4-ethyl-o-phenylene)-3,3-(2,2-dimethyltrimethylenedioxy)-androstane-5α,17β-diol.

1.5 g of the compound prepared in accordance with a) is allowed to react with propine in a manner analogous to Example 2 b). After chromatography over aluminum oxide (neutral, stage III), an amount of 1.43 g of the above-mentioned compound is obtained as white foam.

IR (KBr): 2240 cm$^{-1}$ triple bond c) 17-(prop-1-inyl)-17β-hydroxy-11β,19-(4-ethyl-o-phenylene)-4-androsten-3-one 1.3 g of the substance obtained in accordance with b) is converted in a manner analogous to Example 1 c) into the corresponding 4-ene-3-keto compound. After chromatography over silica gel, an amount of 879 mg of the above-mentioned compound is obtained as white foam.

$[\alpha]_D^{22} = 18°$ (CHCl$_3$; c=0.5)

Fp.=283°-285° C. (acetic ester)

Example 25

17-(3-hydroxy-prop-1(Z)-enyl)-17β-hydroxy-11β,19-(4-ethyl-o-phenylene)-4-androsten-3-one a) 17-[3-(tetrahydropyran-2-yloxy)-prop-1-inyl]-11β,19-(4-ethyl-o-phenylene)-3,3-(2,2-dimethyltrimethelenedioxy)-androstane-5α,17β-diol 2 g of the ethyl compound prepared in accordance with Example 24 a) is allowed to react in a manner analogous to the specifications in Example 5 a) with 3-(tetrahydropyran-2-yloxy)-prop-1-ine. After chromatography over aluminum oxide, an amount of 2.29 g of the title compound is isolated as white foam.

IR (KBr): 2240 cm$^{-1}$ triple bond b) 17-[3-(tetrahydropyran-2-yloxy)-prop-1(Z)-enyl]-11β,19-(4- ethyl-o-phenylene)-3,3-(2,2-dimethyl-trimethelenedioxy)-androstane-5α,17β-diol 2.2 g of the acetyl compound obtained in accordance with a) is hydrogenated to the Z-olefin in a manner analogous to Example 5 b). After chromatography (neutral, stage III), an amount of 1.95 g of the title compound is isolated as white foam.

c) 17-(3-hydroxy-prop-1(Z)-enyl)-17β-hydroxy-11β,19-(4-ethyl-o-phenylene)-4-androsten-3-one 1.9 g of the compound prepared in accordance with b) is split to form the corresponding 4-ene-3-keto compound in a manner analogous to Example 1 c). After chromatography over silica gel, an amount of 706 mg of the above-mentioned title compound is isolated as white foam.

$[\alpha]_D^{22} = 62°$ (CHCl$_3$; c=0.505)

Fp.=127°-129° C. (acetic ester)

Example 26

17-(prop-1-inyl)-17β-hydroxy-11β,19-(4-vinyl-o-phenylene)-4-androsten-3-one a) 11β,19-(4-hydroxy-o-phenylene)-5α-hydroxy-3,3-(2,2-dimethyl-trimethylenedioxy)-androstan-17-one 20 g of the 11β,19-(4-methoxy-o-phenylene)-5α-hydroxy-3,3-(2,2-dimethyltrimethylenedioxy)-androstan-17-one prepared in accordance with Example 4 c) is converted into the corresponding phenol in a manner analogous to Example 18 a). An amount of 16.8 g of the crude product is isolated, the purity of which is adequate for further reactions. 500 mg of the crude product is chromatographed over aluminum oxide for analytical purposes, yielding 412 mg of the title compound.

b) 11β,19-(4-trifluoromethylsulfonyloxy-o-phenylene)-5α-hydroxy-3,3-(2,2-dimethyltrimethylenedioxy)-androstan-17-one 16.3 g of the phenol obtained in accordance with a) is converted into the corresponding trifluarate in a manner analogous to Example 19 a). After chromatography over silica gel, an amount of 15.1 g of the title compound is isolated as white foam.

IR (KBr) 1740 cm$^{-1}$ pentacyclic ketone 1215 and 1420 cm$^{-1}$ triflate c) 11β,19-(4-vinyl-o-phenylene)-5α-hydroxy-3,3-(2,2-dimethyltrimethylenedioxy)-androstan-17-one 1.5 g of the substance prepared in accordance with b) is dissolved in 18 ml of absolute dimethyl formamide and is then treated with 146 mg of palladium tetrakis-triphenyl phosphine and 207 mg of lithium chloride under an inert gas. After stirring for 5 minutes, the reaction mixture is treated with 0.89 ml of tri-n-butylvinyltin and heated to 110° C. After one hour the reaction mixture is cooled to room temperature, diluted with acetic ester and filtered under suction over Celite. The filtrate is washed with saturated sodium chloride, the organic phase is dried over sodium sulfate and concentrated in vacuo. The residue is chromatographed over aluminum oxide (neutral, stage III) yielding an amount of 1.1 g of the title compound as white foam.

d) 17-(prop-1-inyl)-11β,19 -(4-vinyl-o-phenylene)-3,3-(2,2 -dimethyltrimethylenedioxy)-androstane-5α,17β-diol 1 g of the ketone prepared in accordance with a) is allowed to react with propine in a manner analogous to Example 2 b). After chromatography over aluminum oxide (neutral, stage III), an amount of 912 mg of the title compound is isolated as white foam.

IR (KBr): 2240 cm$^{-1}$ triple bond e) 17-(prop-1-inyl)-17β-hydroxy-11β,19-(4-vinyl-o-phenylene)-4-androsten-3-one 850 g of the compound obtained in accordance with d) is converted into the corresponding 4-ene-3-keto compound in a manner analogous to Example 1 c). After chromatography over silica gel, an amount of 485 mg of the title compound is isolated as white foam.

$[\alpha]_D^{22}=50°$ (CHCl$_3$; c=0.505)

Fp.=243°-245° C. (diisopropyl ether)

Example 27

17-(prop-1-inyl)-17β-hydroxy-11β,19-[4-(2-propenyl)-o-phenylene]-4-androsten-3-one a) 11β,19-[4-(2-propenyl)-o-phenylene]-5α-hydroxy-3,3-(2,2-dimethyltrimethylenedioxy)-androstan-17-one 1.5 g of the substance prepared in accordance with Example 26 b) is allowed to react with 0.36 ml of tetraallyl tin in a manner analogous to Example 26 c). After chromatography over silica gel, an amount of 1.06 g of the title compound is isolated as white foam.

b) 17-(prop-1-inyl)-11β,19-[4-(2-propenyl)-o-phenylene]-3,3-(2,2-dimethyltrimethylenedioxy)-androstan-5α,17β-one 1 g of the substance obtained in accordance with a) is allowed to react with propine in a manner analogous to Example 2 b). After chromatography over aluminum oxide (neutral, stage III), an amount of 942 mg of the title compound is isolated as white foam.

IR (KBr): 2240 cm$^{-1}$ triple bond c) 17-(prop-1-inyl)-17β-hydroxy-11β,19-[4-(2-propenyl)-o-phenylene]-4-androstren-3-one 900 mg of the substance prepared in accordance with b) is converted to the corresponding 4-ene-3-keto compound in a manner analogous to Example 1 c). Chromatography over silica gel yields 397 mg of the title compound as white foam.

$[\alpha]_D^{22}=18°$ (CHCl$_3$; c=0.5)

Fp.=275°-277° C. (methylene chloride)

Example 28

17β-hydroxy,11β,19-(4-acetyl-o-phenylene)-4-androsten-3-one a) 11β,19-(4-acetyl-o-phenylene)-3,3-(2,2-dimethyltrimethylenedioxy)-androstane-5α,17β-diol 30 g of the trifluorate prepared in accordance with Example 21 a) is treated with 22.06 g of 1-ethoxy-vinyl-tributyltin in a manner analogous to Example 26 c). After chromatography over silica gel, an amount of 18.75 g of the title compound is isolated as white foam.

Fp.=179°-181 ° C. (diisopropyl ether);

$[\alpha]_D^{22}=146°$ (CHCl$_3$; c=0.5)

b) 17β-hydroxy-11β,19-(4-acetyl-o-phenylene)-4-androsten-3-one 18 g of the substance obtained in accordance with a) is converted into the corresponding 4-ene-3-keto compound in a manner analogous to Example 1 c). After chromatography over silica gel, an amount of 10.8 g of the title compound is isolated as yellowish foam.

Fp.=135°-138 ° C. (acetic ester/hexane)

Example 29

17-(prop-1-inyl)-17β-hydroxy-11β, 19-(4-acetyl-o-phenylene)-4-androsten-3-one a) 11β,19-{4-[1,1-(2,2-dimethyltrimethylenedioxy)-ethyl]-o-phenylene}-3,3-(2,2-dimethyltrimethylenedioxy)-5-androsten-17β-ol 10 g of the substance obtained in accordance with 28 b) is dissolved in 250 ml of absolute toluene and treated in sequence with 25.7 g of 1,3-dimethylpropanediol and 1.86 g of pyridinium para-toluene sulfonate. The reaction mixture is then heated under reflux for 4 hours and the water arising at the same time is removed azeotropically. The reaction mixture is then cooled to room temperature, poured into ice-cold 5% aqueous sodium hydroxide solution and the aqueous phase is extracted with acetic ester. The united organic phases are washed with saturated sodium chloride solution, dried over sodium sulfate and concentrated in vacuo. Chromatography of the residue over aluminum oxide (neutral, stage III) yields 10.7 g of the title compound as white foam.

b) 11β,19-{4-[1,1-(2,2-dimethyltrimethylenedioxy)-ethyl]-o-phenylene}-3,3-(2,2-dimethyltrimethylenedioxy)-5-androsten-17-one 10.5 of the substance obtained in accordance with a) is converted into the 17-keto compound in a manner analogous to Example 2 a). An amount of 10.2 g of the crude product is isolated, the purity of which is adequate for further reactions. 500 mg is chromatographed for analytical purposes over aluminum oxide (neutral, stage III) yielding 443 mg of the title compound as white foam.

$[\alpha]_D^{22}=43°$ (CHCl$_3$; c=0.5)

Fp.=244°-266° C. (acetic ester)

c) 17-(prop-1-inyl)-11β,19-{4-[1,1-(2,2-dimethyltrimethylenedioxy)-ethyl]-o-phenylene}-3,3-(2,2-dimethyltrimethylenedioxy)-5-androsten-17β-ol 1.5 g of the crude product obtained in accordance with b) is allowed to react with propine in a manner analogous to Example 2 b). After chromatography over aluminum oxide (neutral, stage III) with a mixture of acetic ester/hexane, 1.35 g of the title compound is obtained as white foam.

IR (KBr): 2240 cm$^{-1}$ triple bond d) 17-(prop-1-inyl)-17β-hydroxy-11β,19-(4-acetyl-o-phenylene)-4-androsten-3-one 1.3 g of the substance prepared in accordance with c) is split to form the corresponding 4-ene-3-keto compound in a manner analogous to Example 1 c). After chromatography over silica gel, an amount of 747 mg of the title compound is isolated as yellowish foam.

$[\alpha]_D^{22} = 36°$ (CHCl$_3$; c=0.5)

Fp.=186°–187° C. (acetic ester)

Example 30

17-(prop-2-inyl)-17β-hydroxy-11β,19-(4-acetyl-o-phenylene)-4-androsten-3-one a) 17-(3-trimethylsilylprop-2-inyl)-11β,19-{4-[1,1-(2,2-dimethyltrimethylenedioxy)-ethyl]-o-phenylene}-3,3-(2,2-dimethyltrimethylenedioxy)-5-androsten-17β-ol 1.5 g of the compound prepared in accordance with Example 29 b) is allowed to react with 2.3 ml of 1-trimethylsilylprop-1-ine in a manner analogous to Example 5 a). After chromatography over aluminum oxide (neutral, stage III), an amount of 1.31 g of the title compound is isolated as white foam.

IR (KBr): 2170 cm$^{-1}$ triple bond b) 17-(prop-2-inyl)-17β-hydroxy-11β,19-(4-acetyl-o-phenylene)-4-androsten-3-one 1.2 g of the substance prepared in accordance with a) is converted into the corresponding 4-ene-3-keto compound under conditions analogous to those described in Example 1 c). After chromatography over silica gel, 547 mg of the title compound is isolated as white foam.

$[\alpha]_D^{22} = 91°$ (CHCl$_3$; c=0.5)

Fp.=257°–259° C.

Example 31

17-(prop-1-inyl)-17β-hydroxy-11β,19-(4-acetyl-o-phenylene)-4,15-androstadien-3-one a) 11β,19-{4-[1,1-(2,2-dimethyltrimethylenedioxy)-ethyl]-o-phenylene}-3,3-(2,2-dimethyltrimethylenedioxy)-5,15-androstadien-17-one 1.89 g of the compound prepared in accordance with Example 29 b) dissolved in 20 ml of absolute tetrahydrofuran is added dropwise to a solution of 9.9 mmol of lithium diisopropylamide in 40 ml of absolute tetrahydrofuran in an inert atmosphere at 0° C. Thereupon chlorotrimethylsilane (2.39 ml) is added dropwise to the reaction mixture. After having been stirred for 30 minutes the reaction solution is poured into ice-cold saturated sodium bicarbonate solution, the aqueous phase then being extracted with acetic ester and the organic phase being washed with water and saturated ammonium chloride solution. After drying over sodium sulfate, the organic phase is concentrated in vacuo. An amount of 1.96 g of 17-trimethylsilyloxy-11β,19-{4-[1,1-(2,2-dimethyltrimethylenedioxy)-ethyl]-o-phenylene}-3,3-(2,2-dimethyltrimethylenedioxy)-5,16-androstadiene is isolated in a crude state as yellowish foam. This crude product is suspended in 23 ml of absolute acetonitrile and treated with 1 g of palladium (II) acetate. After having been stirred for two hours at room temperature, the reaction mixture is filtered under suction over Celite, the filter residue washed with acetic ester and the filtrate is concentrated under in vacuo. The residue is chromatographed over aluminum oxide (neutral, stage III), an amount of 1.33 g of the title compound being obtained as white foam.

IR (KBr): 1710 cm$^{-1}$ unsaturated pentacyclic ketone b) 17-(prop-1-inyl)-11β,19-{4-[1,1-(2,2-dimethyltrimethylenedioxy)-ethyl]-o-phenylene}-3,3-(2,2-dimethyltrimethylenedioxy)-5,15-androstadien-17β-ol 1.3 g of the substance prepared in accordance with a) are allowed to react with propine in a manner analogous to Example 2 b). After chromatography over aluminum oxide (neutral, stage III), an amount of 1.23 g of the title compound is isolated as white foam.

IR (KBr): 2230 cm$^{-1}$ triple bond c) 17-(prop-1-inyl)-17β-hydroxy-17β,19-(4-acetyl-o-phenylene)-4,15-androstadien-3-one 1.1 g of the substance prepared in accordance with b) is split to form the corresponding 4-ene-3-keto compound in a manner analogous to Example 1 c). After chromatography over silica gel, an amount of 617 mg of the title compound is isolated as yellowish foam.

$[\alpha]_D^{22} = 114°$ (CHCl$_3$; c=0.5)

Fp.=189°–191° C. (acetic ester)

Example 32

17-methoxymethyl-17β-hydroxy-11β,19-(4-acetyl-o-phenylene)-4-androsten-3-one a) 11β,19-{4-[1,1-(2,2-dimethyltrimethylenedioxy)-ethyl]-o-phenylene}-3,3-(2,2-dimethyltrimethylenedioxy)-5-androsten-[17(β-1')-spiro-3']-oxirane 4 g of the compound prepared in accordance with Example 29 b) is allowed to react with 7.13 g of trimethylsulfonium iodide in a manner analogous to Example 14 a). After chromatography over aluminum oxide (neutral, stage III), an amount of 3.76 g of the title compound is isolated as white foam.

b) 17-methoxymethyl-11β,19-{4-[1,1-(2,2-dimethyltrimethylenedioxy)-ethyl]-o-phenylene}-3,3-(2,2-dimethyltrimethylenedioxy)-5-androsten-17β-ol 1.8 g of the substance prepared in accordance with a) is allowed to react with sodium methylate in a manner analogous to Example 14 b). After chromatography over aluminum oxide (neutral, stage III), an amount of 1.55 g of the title compound is isolated as white foam.

c) 17-methoxymethy-17β-hydroxy-11β,19-(4-acetyl-o-phenylene)-4-androsten-3-one 1.5 g of the substance obtained in accordance with b) is split to form the corresponding 4-ene-3-keto compound in a manner analogous to Example 1 c). After chromatography over silica gel, an amount of 561 mg of the title compound is isolated as yellowish foam.

$[α]_D^{22} = 76°$ (CHCl₃; c=0.5)

Example 33

17-cyanomethyl-17β-hydroxy-11β,19-(4-acetyl-o-phenylene)-4-androsten-3-one a) 17-cyanomethyl-11β,19-{4-[1,1-(2,2-dimethyltrimethylenedioxy)-ethyl]-o-phenylene}-3,3-(2,2-dimethyltrimethylenedioxy)-5-androsten-17β-ol 1.8 g of the substance obtained in accordance with Example 32 a) is allowed to react with potassium cyanide in a manner analogous to Example 6 b). After chromatography over aluminum oxide (neutral, stage III), an amount of 1.67 g of the title compound is isolated as white foam.

IR (KBr): 2250 cm⁻¹ C≡N triple bond b) 17-cyanomethyl-17β-hydroxy-11β,19-(4-acetyl-o-phenylene)-4-androsten-3-one 1.5 g of the substance obtained in accordance with a) is split to form the corresponding 4-ene-3-keto compound in a manner analogous to Example 1 c). After chromatography over silica gel, an amount of 732 mg of the title compound is isolated as white foam.

$[α]_D^{22} = 83°$ (CHCl₃; c=0.5)

Fp.=184°-185° C. (methylene chloride)

Example 34

17-(prop-1-inyl)-17β-hydroxy-11β,19 -(4-isopropenyl-o-phenylene)-4-androsten-3-one a) 11β,19-(4-isopropenyl-o-phenylene)-3,3-(2,2-dimethyltrimethylenedioxy)-androstane-5α,17β-diol In an inert atmosphere, 1.94 g of sodium hydride is warmed at 70° C. in 20 ml of absolute dimethyl sulfoxide until no more gas production is detected. The solution is then cooled down to 0° C. and treated dropwise with methyltriphenyl phosphonium bromide dissolved in 61 ml of absolute dimethyl sulfoxide. After stirring at room temperature, 10.3 g of the compound prepared in accordance with Example 28 a) dissolved in 10 ml of absolute dimethyl sulfoxide is added dropwise, the reaction mixture being stirred for 3 hours. Thereafter the reaction mixture is poured into cold saturated sodium bicarbonate solution. The aqueous phase is extracted with acetic ester and the organic phases are washed with saturated sodium chloride solution. The united organic phases are dried over sodium sulfate and concentrated in vacuo. The residue is chromatographed over aluminum oxide (neutral, stage III). This yields 8.3 g of the title compound as white foam.

Fp.=155°-157° C. (diisopropyl ether)

b) 11β,19-(4-isopropenyl-o-phenylene)-5α-hydroxy-3,3-(2,2-dimethyltrimethylenedioxy)-androstan-17-one 8.1 g of the substance prepared in accordance with a) is oxidized with chromium trioxide in a manner analogous to Example 2 a). After chromatography over aluminum oxide (neutral, stage III), an amount of 7.8 g of the title compound is isolated as white foam.

Fp.=238°-240° C. (diisopropyl ether)

c) 17-(prop-1-inyl)-11β,19-(4-isopropenyl-o-phenylene)-3,3-(2,2-dimethyltrimethylenedioxy)-androstane-5α,17β-diol 1.5 g of the substance obtained in accordance with b) is allowed to react with propine in a manner analogous to Example 2 b). After chromatography over aluminum oxide (neutral, stage III), an amount of 1.34 g of the title compound is isolated as white foam.

IR (KBr): 2240 cm⁻¹ triple bond d) 17-(prop-1-inyl) -17β-hydroxy-11β,19- (4-isopropenyl-o-phenylene)-4-androsten-3-one 1.3 g of the compound obtained in accordance with c) is converted to the 4-ene-3-keto compound in a manner analogous to Example 1 c). After chromatography over silica gel, an amount of 706 mg of the title compound is isolated as white foam.

$[α]_D^{22} = 41°$ (CHCl₃; c=0.5)

Fp.=247°-250° C. (diisopropyl ether)

As a by-product 17-(prop-1-inyl)-17β-hydroxy-11β,19-[4-(1-methyl-hydroxyethyl)-o-phenylene]-4-androsten-3-one (354 mg) is isolated as white foam.

$[α]_D^{22} = 17°$ (CHCl₃; c=0.5)

Fp.=222°-224° C.

Example 35

17-(prop-1-inyl)-17β-hydroxy-11β,19-(4-isopropyl-o-phenylene)-4-androsten-3-one a) 11β,19-(4-isopropyl-o-phenylene)-5α-hydroxy-3,3-(2,2-dimethyltrimethylenedioxy)-androstan-17-one 2 g of the substance obtained in accordance with Example 34 b) is hydrogenated as described in Example 23 a) but only up to absorption of one equivalent of hydrogen, with palladium as a catalyst. After chromatography over aluminum oxide (neutral, stage III), an amount of 1.83 g of the title compound is isolated as white foam.

b) 17-(prop-1-inyl)-11β,19-(4-isopropenyl-o-phenylene)-3,3(2,2-dimethyltrimethylenedioxy)-androstene-5α,17β-diol 1.8 g of the substance prepared in accordance with a) is allowed to react with propine in a manner analogous to Example 2 b). After chromatography over aluminum oxide (neutral, stage III), an amount of 1.81 g of the title compound is isolated as white foam.

c) 17-(prop-1-inyl)-17β-hydroxy-11β,19-(4-isopropenyl-o-phenylene)-4-androsten-3-one 1.7 g of the substance prepared in accordance with b) is split to form the 4-ene-3-keto compound in a manner analogous to Example 1 c). After chromatography over silica gel, an amount of 932 mg of the title compound is isolated as white foam.

$[α]_D^{22} = 21°$ (CHCl₃; c=0.505)

Fp.=240°-243° C. (acetic ester)

Example 36

17-(3-hydroxyprop-1(Z)-enyl)-17β-hydroxy-11β,19-(4-isopropenyl-o-phenylene)-4-androsten-3-one a) 17-[3-(tetrahydropyran-2-yloxy)-prop-1-inyl]-11β,19-(4-isopropenyl-o-phenylene)-3,3-(2,2-dimethyltrimethylenedioxy)-androstane-5α,17β-diol 2 g of the substance obtained in accordance with Example 34 b) is allowed to react with 3-(tetrahydropyran-2-yloxy)-prop-1-ine in a manner analogous to Example 5 a). After chromatography over aluminum oxide (neutral, stage III), an amount of 2.1 g of the title compound is isolated as white foam.

b) 17-[3-(tetrahydropyran-2-yloxy)-prop-1(Z)-enyl]-11β,19-(4-isopropenyl-o-phenylene)-3,3-(2,2-dimethyltrimethylenedioxy)-androstane-5α,17β-diol 2 g of the compound obtained in accordance with a) is hydrogenated in a manner analogous to Example 5 b) with Lindlar's catalyst. After chromatography over aluminum oxide (neutral, stage III), an amount of 1.78 g of the title compound is isolated as white foam.

c) 17-(3-hydroxyprop-1(Z)-enyl)-17β-hydroxy-11β,19-(4-isopropenyl-o-phenylene)-4-androsten-3-one 1.7 g of the compound obtained in accordance with b) is split to form the 4-ene-3-keto compound in a manner analogous to Example 1 c). After chromatography over silica gel, an amount of 567 mg of the title compound is isolated as white foam.

$[\alpha]_D^{22} = 79°$ (CHCl$_3$; c=0.5)

Fp.=143°–145 ° C. (acetic ester)

As a by-product 178 mg of 17-(3-hydroxyprop-1(Z)-enyl)-17β-hydroxy-11β,19-[4-(1-methyl-1-hydroxyethyl)-o-phenylene]-4-androstene-3-one is isolated as white foam.

$[\alpha]_D^{22} = 61°$ (CHCl$_3$; c=0.5)

Fp.=208°–211° C. (acetic ester)

Example 37

17-(4-hydroxybut-1(Z)-enyl)-17β-hydroxy-11β,19-(4-isopropenyl-o-phenylene)-4-androsten-3-one a) 17-(4-hydroxybut-1-inyl)-11β,19-(4-isopropenyl-o-phenylene)-3,3-(2,2-dimethyltrimethylenedioxy)-androstane-5α,17β-diol 2 g of the substance obtained in accordance with Example 34 b) is dissolved in 60 ml of absolute tetrahydrofuran and is treated in sequence in an inert atmosphere with 2.27 ml n-but-1-in-4-ol and 4.09 g of potassium methylate. During this process of addition and the subsequent 14 hour period of stirring the reaction mixture is kept at 0° C. Thereafter it is poured into water and the aqueous phase is extracted with acetic ester. The united organic phases are washed with saturated sodium chloride solution, dried over sodium sulfate and concentrated in vacuo. The residue is chromatographed over aluminum oxide (neutral, stage III) and an amount of 1.2 g of the title compound is isolated as white foam.

IR (KBr): 2240 cm$^{-1}$ triple bond b) 17-(4-hydroxybut-1(Z)-enyl)-11β,19-(4-isopropenyl-o-phenylene)-3,3-(2,2-dimethyltrimethylenedioxy)-androstane-5α,17β-diol 1 g of the substance obtained in accordance with a) is hydrogenated using Lindlar's catalyst in a manner analogous to Example 5 b). After chromatography over aluminum oxide (neutral, stage III), an amount of 836 mg of the title compound is obtained as white foam.

c) 17-(4-hydroxybut-1(Z)-enyl)-17β-hydroxy-11β,19-(4-isopropenyl-o-phenylene)-4-androsten-3-one 800 mg of the substance obtained in accordance with b) is split to form the 4-ene-3-keto compound in a manner analogous to Example 1 c). After chromatography over silica gel, an amount of 306 mg of the title compound is isolated as white foam.

$[\alpha]_D^{22} = 78°$ (CHCl$_3$; c=0.515)

Example 38

17-(prop-1-inyl)-17β-hydroxy-11β,19-(4-diethoxyphosphoryl-o-phenylene)-4-androsten-3-one a) 11β,19-(4-diethoxyphosphoryl-o-phenylene)-5α-hydroxy-3,3-(2,2-dimethyltrimethylenedioxy)-androstan-17-one 1.5 g of the trifluorate obtained in accordance with Example 26 b) is dissolved in 10 ml of absolute triethylamine and treated in an inert atmosphere with 122 mg of tetrakistriphenyl phosphine palladium and 0.46 ml of phosphorous acid diethyl ester. Thereafter the reaction mixture is heated for 1.5 hours under reflux. After addition of a further 100 mg of tetrakistriphenyl phosphine palladium and 0.46 ml of phosphorous acid diethyl ester, the reaction mixture is heated under reflux for a further 1.5 hours, allowed to cool to room temperature and concentrated in vacuo. The residue is chromatographed over silica gel and yields 1.05 g of the title compound as white foam.

b) 17-(prop-1-inyl)-11β,19-(4-diethoxyphosphoryl-o-phenylene)-3,3-(2,2-dimethyltrimethylenedioxy)-androstane-5α,17β-diol 1 g of the substance prepared in accordance with a) is allowed to react with propine in a manner analogous to Example 2 b). Chromatography over aluminum oxide (neutral, stage III) yields 832 mg of the title compound as white foam.

IR (KBr): 2240$^{-1}$ cm triple bond c) 17-(prop-1-inyl )-17β-hydroxy-11β,19-(4-diethoxyphosphoryl-o-phenylene)-4-androsten-3-one 800 mg of the substance prepared in accordance with b) is split to form the 4-ene-3-keto compound in a manner analogous to Example 1 c). After chromatography over silica gel, an amount of 440 mg of the title compound is isolated as white foam.

$[\alpha]_D^{22} = 17°$ (CHCl$_3$; c=0.5)

Example 39

17-(prop-1-inyl)-17β-hydroxy-11β,19-[4-(2-thienyl)-o-phenylene]-4-androsten-3-one a) 11β,19-[4-(2-thienyl)-o-phenylene]-3,3-(2,2-dimethyltrimethylenedioxy)-androstane-5α,17β-diol 1.26 g of the substance prepared in accordance with Example 21 a) is dissolved in 36 ml of absolute dioxane and treated in an inert atmosphere with 3.04 ml of hexa-n-butyl-di-tin, 254 mg of lithium chloride and 100 mg of tetrakistriphenyl phosphine palladium. Thereupon the reaction mixture is heated to 110° C. and kept at this temperature for 1 hour before addition of 1.94 ml of 2-bromothiophene. It is then stirred for a further period of 18 hours at 110° C. The reaction mixture is then cooled to room temperature and filtered over Celite. After concentration of the filtrate, the residue is chromatographed over silica gel to yield 545 mg of the title compound as yellowish foam.

As an example of this type of coupling the following tin compound was isolated.

α11β,19-(4-tri-n-butylstannyl-o-phenylene)-3,3-(2,2-dimethyltrimethylenedioxy)-androstane-5α,17β-diol 1.26 g of the substance prepared in accordance with Example 21 a) is allowed to react with 3.04 ml of hexan-butyl-di-tin under conditions analogous to those described under a). After heating for 1 hour at 110° C., the reaction mixture is treated further in a normal manner. Chromatography over silica gel yields 625 mg of the title compound as white foam.

$[\alpha]_D^{22} = 25°$ (CHCl$_3$; c=0.5)

Fp.=137°-139° C. (diisopropyl ether)

b) 11β,19-[4-(2-thienyl)-o-phenylene]-5α-hydroxy-3,3-(2,2-dimethyltrimethylenedioxy)-androstan-17-one 400 mg of N-chlorosuccinimide is provided in 5 ml of absolute methylene chloride at 0° C. After dropwise addition of 0.3 ml of dimethyl sulfide, the mixture is stirred for 30 minutes at 0° C. Thereupon 510 mg of the substance obtained in accordance with a) dissolved in 5 ml of absolute methylene chloride is slowly added drop for drop. After two hours of stirring with exclusion of moisture, 0.6 ml of triethylamine is added dropwise to the reaction mixture. This is then poured into water, the aqueous phase is extracted with methylene chloride and the organic phase is washed with saturated sodium chloride solution. Thereafter it is dried over sodium sulfate and concentrated in vacuo. After chromatography of the residue over aluminum oxide (neutral, stage III), an amount of 387 mg of the title compound is isolated as yellowish foam.

IR (KBr): 1740 cm$^{-1}$ pentacyclic ketone c) 17-(prop-1-inyl) -11β,19-[b 4-(2-thienyl)-o-phenylene]-3,3-(2,2 -dimethyltrimethylenedioxy)-androstane-5α,17β-diol 350 mg of the substance obtained in accordance with b) is allowed to react with propine in a manner analogous to Example 2 b). After chromatography over aluminum oxide (neutral, stage III), an amount of 343 mg of the title compound is isolated as yellowish foam.

IR (KBr): 2240 cm$^{-1}$ triple bond d) 17-(prop-1-inyl)-17β-hydroxy-11β,19-[4-(2-thienyl)-o-phenyl-ene]-4-androsten-3-one 320 mg of the compound obtained in accordance with d) is split to form the 4-ene-3-keto compound in a manner analogous to Example 1 c). After chromatography over silica gel, an amount of 234 mg of the title compound is isolated as yellowish foam.

$[\alpha] = 65°$ (CHCl$_3$; c=0.5)

Example 40

17-( prop-1-inyl)-17β-hydroxy-11β,19-[4-(3-thienyl)-o-phenylene]-4-androsten-3-one a) 11β,19-[4-(3-thienyl)-o-phenylene]-5α-hydroxy-3,3-(2,2-dimethyltrimethylenedioxy)-androstan-17-one 1.26 g of the substance obtained in accordance with Example 26 b) is allowed to react with 2 ml of 3-bromothiophene under conditions analogous to those described under Example 39 a). After chromatography over aluminum oxide (neutral, stage III), an amount of 546 mg is isolated as yellowish foam.

17-(prop-1-inyl)-11β,19-[4-(3-thienyl)-o-phenylene]-3,3(2,2-dimethyltrimethylenedioxy)-androstane-5α,17β-diol 520 mg of the substance prepared in accordance with a) is allowed to react with propine in a manner analogous to Example 2 b). After chromatography over aluminum oxide (neutral, stage III), an amount of 462 mg of the title compound is isolated as yellowish foam.

IR (KBr): 2250 cm$^{-1}$ triple bond c) 17-(prop-1-inyl)-17β-hydroxy-11β,19-[4-(3-thienyl)-o-phenyl-ene]-4-androsten-3-one 410 mg of the substance obtained in accordance with b) is split to form the 4-ene-3-keto compound in a manner analogous to Example 1 c). After chromatography over silica gel, an amount of 287 mg of the title compound is isolated as yellowish foam.

$[\alpha]_D^{22} = 61°$ (CHCl$_3$; C=0.5)

Example 41

17-(prop-1-inyl)-17β-hydroxy-11β,19-[4-(3-furyl)-o-phenylene]-4-androsten-3-one a) 11β,19-[4-(3-furyl)-o-phenylene]-5α-hydroxy-3,3-(2,2-dimethyltrimethylenedioxy)-androstan-17-one 1.26 g of the substance prepared in accordance with Example 26 b) is allowed to react with 1.8.ml of 3-bromofuran in a manner analogous to Example 39 a). After chromatography over silica gel, an amount of 660 mg of the title compound is isolated as white foam.

Fp.=240°-243° C. (acetic ester)

b) 17-(prop-1-inyl)-11β,19-[4-(3-furyl)-o-phenylene]-3,3-(2,2-dimethyltrimethylenedioxy)-androstane-5α-17β-diol 630 mg of the substance obtained in accordance with a) is allowed to react with propine in a manner analogous to Example 2 b). After chromatography over aluminum oxide (neutral, stage III), an amount of 615 mg of the title compound is isolated as white foam.

IR (KBr): 2240 cm$^{-1}$ triple bond c) 17-(prop-1- inyl)-17β-hydroxy-11β,19-[4-(3-furyl)-o-phenylene]-4 - androsten-3-one 590 mg of the substance obtained in accordance with b) is allowed to react to form the 4-ene-3-keto compound in a manner analogous to Example 1 c). After chromatography over silica gel, an amount of 289 mg of the title compound is isolated as white foam.

$[\alpha]_D^{22} = 49°$ (CHCl$_3$; c=0.5 1 )

Example 42

17-(prop -1- inyl)-17β-hydroxy
-11β,19-[4-(3-methoxyphenyl)-o-phenylene]-4-androsten-3-one a)    11β,19-[4-(3-methoxyphenyl)-o-phenylene]-5α-hydroxy-3,3-(2,2-dimethyltrimethylenedioxy)-androstan-17-one 1.26g of the substance prepared in accordance with Example 26 b) is allowed to react with 2.53 ml of 3-bromo-anisol in a manner analogous to example 39 a). After chromatography over silica gel, an amount of 685 mg of the title compound is isolated as white foam.

17-(prop-1-inyl)-11β,19-[4-(3-methoxyphenyl)-o-phenylene]-3,3-(2,2-dimethyltrimethylenedioxy)-androstane-5α,17β-diol 650 mg of the substance prepared in accordance with a) is allowed to react with propine in a manner analogous to Example 2 b). After chromatography over aluminum oxide (neutral, stage III), an amount of 635 mg of the title compound is isolated as white foam.

IR (KBr): 2230 cm$^{-1}$ triple bond c) 17-(prop-1-inyl)-17β-hydroxy-11β,19-[4-(3-methoxyphenyl)-o-phenylene]-4- androsten-3-one 600 mg of the substance prepared in accordance with b) is converted to the 4-ene-3-keto compound under conditions analogous to those described in Example 1 c). After chromatography over silica gel, an amount of 366 mg of the title compound is isolated as white foam.

$[\alpha]_D^{22}=66°$ (CHCl$_3$; c=0.5)

Fp.=158°-162 ° C. (acetic ester/hexane)

Example 43

17-(prop-1-inyl) -17β-hydroxy
-11β,19-[4-(methoxyphenyl)-o-phenylene]-4-androsten-3-one a)    11β,19-[4-(4-methoxyphenyl)-o-phenylene]-5α-hydroxy-3,3-(2,2-dimethyltrimethylenedioxy)-androstan-17-one 1.26g of the substance prepared in accordance with Example 26 b) is allowed to react with 2.53 ml of 4-bromo-anisol in a manner analogous to Example 39. a). After chromatography over silica-gel, an amount of 522 mg of the title compound is isolated as white foam.

Fp.=171°-173 ° C. (acetic ester)

$[\alpha]_D^{22}=48°$ (CHCl$_3$; c=0.5)

b)    17-(prop-1-inyl)-11β,19-[4-(4-methoxyphenyl)-o-phenylene]3,3-(2,2-dimethyltrimethylenedioxy)-androstane-5α,17β-diol 500 mg of the substance prepared in accordance with a) is allowed to react with propine in a manner analogous to Example 2 b). After chromatography over aluminum oxide (neutral, stage III), an amount of 498 mg of the title compound is isolated as white foam.

IR (KBr): 2240 cm$^{-1}$ triple bond c) 17-(prop-1-inyl)-17β-hydroxy-11β,19-[4-(4-methoxyphenyl)-o-phenylene]-4-androsten-3-one 450 mg of the substance prepared in accordance with b) is converted to the 4-ene-3-keto compound in a manner analogous to Example 1 c). After chromatography over silica gel, an amount of 276 mg of the title compound is isolated as white foam.

$[\alpha]_D^{22}=70°$ (CHCl$_3$; c=0 505)

Fp.=165°-169 ° C. (acetic ester/hexane)

Example 44

17-(prop-1-inyl)-17β-hydroxy-11β,19-[4-(2-methoxypheny)-o-phenylene]-4-androsten-3-one a)    11β,19- [4-(2-methoxyphenyl)-o-phenylene]-5α-hydroxy-3,3-(2,2-dimethyltrimethylenedioxy)-androstan-17-one 1.26g of the substance obtained in accordance with Example 26 b is allowed to react with 2.53 ml of 2-bromo-anisol in a manner analogous to Example 39 a). After chromatography over silica gel, an amount of 448 mg of the title compound is isolated as white foam.

b)    17-(prop-1-inyl)-11β,19-[4-(2-methoxyphenyl)-o-phenylene]3,3-(2,2-dimethyltrimethylenedioxy)-androstane-5α,17β-diol 410 mg of the substance prepared in accordance with a) is allowed to react with propine in a manner analogous to Example 2 b). After chromatography over aluminum oxide (neutral, stage III), an amount of 405 mg of the title compound is isolated as white foam.

IR (KBr): 2240 cm$^{-1}$ triple bond c) 17-(prop-1-inyl) -17β-hydroxy-11β,19-[4-(2-methoxyphenyl)-o-phenylene]-4 -androsten-3-one 380 mg of the substance prepared in accordance with b) is converted to the 4-ene-3-keto compound in a manner analogous to Example 1 c) . After chromatography over silica gel, an amount of 205 mg of the title compound is isolated as white foam.

$[\alpha]_D^{22}=49°$ (CHCl$_3$; c=0.51)

Example 45

17-(prop-1-inyl)
-17β-hydroxy-11β,19-(4,5-methylenedioxy-o-phenylene)-4-androsten-3-one a)    19-(2-chloro-4,5-methylenedioxyphenyl)-3,3-(2,2-dimethyltrimethylenedioxy)-9(11)-androstene-5α,17β-diol Analogous to Example 1 a) 10.3 g of 19-(2-chloro-4,5-methylenedioxyphenyl)-3,3-(2,2-dimethyltrimethylenedioxy)-9(11)-androstene-5α,17β-diol is obtained from 10 g of 5α,10α- epoxy-3,3-(2,2-dimethyltrimethylenedioxy)-9(11)-estren-17β-ol by reaction with 6-chloropiperonyl chloride.

b)    11β,19-(4,5-methylenedioxy-o-phenylene)-3,3-(2,2-dimethyltrimethylenedioxy)-androstane-5α,17β-diol Analogous to Example 1 b), an amount of 5.9 g of 11β,19-(4,5-methylenedioxy-o-phenylene)-3,3-(2,2-dimethyltrimethylenedioxy)-androstane-5α,17β-diol is produced as white foam from 10 g of the compound obtained in accordance with a).

c)    11β,19-(4,5-methylenedioxy-o-phenylene)-5α-hydroxy-3,3(2,2-dimethyltrimethylenedioxy)-androstan-17-one Analogous to Example 2a) 5.5 g of the compound obtained in accordance with b) is converted into the corresponding keto compound. An amount of 4.2 g of 11β,19-(4,5-methylenedioxy-o-phenylene)-5α-hydroxy-3,3-(2,2-dimethyltrimethylenedioxy)-androstan-17-one is obtained as white foam.

$[\alpha]_D^{22} = +45°$ (CHCl$_3$; c=0.525)

Fp.=219°-222 ° C. (ethyl acetate.)

d) 17-(prop-1-inyl)-11β,19-(4,5-methylenedioxy-o-phenylene)-3,3-(2,2-dimethyltrimethylenedioxy)-androstane-5α-17β-diol Analogous to example 2 b) 4 g of the compound obtained in accordance with c) is converted into the corresponding 17α-propinyl compound. After chromatography, an amount of 3.5 g of 17-(prop-1-inyl)-11β,19-(4,5-methylenedioxy-o-phenylene)-3,3-(2,2-dimethyltrimethylenedioxy)-androstane-5α,17β-diol is isolated as white foam.

IR (KBr): 2230 cm$^{-1}$ triple bond e) 17-(prop-1-inyl)-17β-hydroxy-11β,19-(4,5-methylenedioxyphenylene)-4-androsten-3-one Analogous to Example 1 c) 3 g of the compound obtained in accordance with d) is converted to the corresponding 4-ene-3-keto compound. An amount of 1.36 g of 17-(prop-1-inyl)-17β-hydroxy-11β,19-(4,5-methylenedioxy-o-phenylene)-4-androsten-3-one is isolated.

$|\alpha|_D^{22} = +2°$ (CHCl$_3$; c=0.485)

Example 46

18-Methyl-17-ethinyl-17beta-hydroxy-11beta,19-(4-methoxy-o-phenylene)-4-androsten-3-one a) 18-Methyl-5alpha,10alpha-epoxy-3,3-(2,2-dimethyltrimethylenedioxy)-9(11)-estren-17beta-ol Sodium borohydride (2.38 g) is put in 100 ml of absolute tetrahydrofuran and the suspension is cooled to 0° C. Under protective gas, 20 g of 18-methyl-5alpha,10alpha-epoxy-3,3-(2,2-dimethyltrimethylenedioxy)-9(11)-estren-17-one (European patent application 0104387A1), dissolved in a mixture of 100 ml of methanol and 100 ml of tetrahydrofuran, is instilled. After 45-minutes additional stirring, saturated sodium bicarbonate solution is slowly instilled to decompose the excess reducing agent, and the aqueous phase is extracted with ethyl acetate. The combined organic phases are washed with saturated sodium chloride solution, dried on sodium sulfate and concentrated by evaporation in a vacuum. The residue is chromatographed on aluminum oxide (neutral, stage III) with a mixture of ethyl acetate/hexane. 18.3 g of the above-mentioned 17beta-hydroxy compound is obtained as white foam.

b) 19-(2-Bromo-5-methoxyphenyl) -18-methyl-3,3-(2,2-dimethyltrimethyenedioxy)-9(11) -androstene-5alpha, 17beta-diol Analogously to directions described under example 4alpha), 3.8 g of the epoxide prepared under a) is reacted with 16.79 g of 2-bromo-5-methoxybenzyl bromide. 3.65 g of the above-mentioned compound is obtained as white foam.

c) 18-Methyl-11beta,19-(4-methoxy-o-phenylene)-3,3-(2,2dimethyltrimethenedioxy)-androstane-5alpha, 17beta-diol 3.5 g of the aryl halide prepared under b), dissolved in 100 ml of absolute toluene, is mixed with 46 mg of alpha,alphaazoisobutyronitrile and then irradiated with an incandescent lamp (300 watts) for 2.5 hours. In this case the irradiation is concentrated by aluminum foil on the reaction vessel and the resulting heat is used for refluxing the reaction mixture. Then the reaction solution is cooled and concentrated by evaporation in a vacuum. The residue is chromatographed on aluminum oxide (neutral, stage III) with a mixture of ethyl acetate/hexane. 2.32 g of the above-mentioned o-phenylene compound is obtained as white foam.

d) 18-Methyl-11beta,19-(4-methoxy-o-phenylene)-5alpha-hydroxy-3,3-(2,2-dimethyltrimethylenedioxy)-androstan-17-one Analogously to the directions described under example 2a), 2.2 g of the 17beta-hydroxy compound prepared under c) is reacted with chromium trioxide. 2.05 g of the above-mentioned compound is obtained as yellowish foam.

e) 18-Methyl-17-ethinyl-11beta,19-(4-methoxy-o-phenylene)-3,3-(2,2-dimethytrimethylenedioxy)-androstane-5alpha,17beta-diol 190 ml of absolute tetrahydrofuran is saturated with ethine at 0° C. Then 30.2 ml of a 1.6-m n-butyllithium solution (hexane) without any considerable increase of temperature is slowly instilled in this solution. After stirring for 15 more minutes, a solution of 2 g of the ketone prepared under d), dissolved in 35 ml of absolute tetrahydrofuran, is instilled slowly with ice-bath cooling into this reaction mixture and stirred for 30 more minutes. Then the reaction mixture is poured onto water, the aqueous phase is extracted with ethyl acetate and the organic phase is washed with sodium chloride solution. After drying on sodium sulfate and concentration by evaporation of the organic phase in a vacuum, the residue is chromatographed on aluminum oxide (neutral, stage III). 1.67 g of above-mentioned compound is obtained as white foam.

f) 18-Methyl-17-ethinyl-17beta-hydroxy-11beta,19-(4-methoxy-o-phenylene) -4-androsten-3-one Analogously to the directions described under example 1c), 1.6 g of the ethinyl compound prepared under e) is reacted. 918 mg of the title compound is obtained as white foam.

$[\alpha]_D^{22} = 48°$ (CHCl$_3$; c=0.5)

Example 47

18-Methy-17-(prop-1-inyl-17beta-hydroxy-11beta,19-(4-dimethylamino-o-phenylene)-4-androsten-3-one a) 19-(2-Chloro-5-dimethylaminophenyl)-18-methyl-3,3-(2,2-dimethyltrimethylenedioxy)-9(11)-androstene-5alpha,17beta-diol Analogously to the directions described under example 1a), 3.8 g of the epoxide prepared under example 46a) is reacted with 16.32 g of 2-chloro-5-dimethylaminobenzyl chloride. 3.1 g of the above-mentioned compound is obtained as white foam.

b) 18-Methyl-11beta,19-(dimethylamino-o-phenylene)-3,3-(2,2dimethyltrimethylenedioxy)-androstane-5alpha, 17beta-diol 115 ml of anhydrous ammonia is condensed, with exclusion of moisture, in a round-bottom flask at −78° C. After addition of 220 mg of lithium and appearance of the characteristic blue color, a solution of 3 g of the aryl halide prepared under a) is slowly instilled in 230 ml of tetrahydrofuran. After addition is completed, it is stirred for 20 more minutes and then the excess lithium is eliminated by instillation of ethanol. Then most of the ammonia is removed by evaporation, the reaction mixture is poured onto water and the aqueous phase is extracted several times with ethyl acetate. The combined organic phases are washed with sodium chloride solution, dried on sodium sulfate and concentrated by evaporation. The residue is chromatographed on aluminum oxide (neutral, stage III) with a mixture of ethyl acetate/hexane. 1.6 g of the above-mentioned compound is isolated as white foam.

c) 18-Methyl-11beta,19-(4-dimethylamino-o-phenylene)-5alpha-hydroxy-3,3-(2,2-dimethyltrimethylenedioxy)-androstan-17-one Analogously to the directions described under example 13c), 1.5. g of the 17beta-hydroxy compound prepared under b) is oxidized. 1.24 g of the above-mentioned compound is obtained.

$[\alpha]_D^{22} = 15°$ (CHCl$_3$; c=0.5); mp=274°–278° C.
(ethyl acetate/hexane)

d) 18-Methyl-17-(prop-1-inyl)-11beta,19-(4-dimethylamino-o-phenylene)-3,3-(2,2-dimethyltrimethylenedioxy)-androstane-5alpha,17beta-diol Analogously to the directions described under example 2b), 1.2 g of the keto compound prepared under c) is converted into the corresponding 17alpha-propinyl compound. 1.14 g of the above-mentioned compound is obtained as white foam.

e) 18-Methyl-17-(prop-1-inyl)-17beta-hydroxy-11beta,19-(4dimethylamino-o-phenylene)-4-androsten-3-one Analogously to the directions described in example 1c), 1.1 g of the propinyl compound prepared under d) is reacted. 602 mg of the title compound is obtained as a yellowish foam.

$[\alpha]_D^{22} = 49°$ (CHCl$_3$; c=0.5)

Example 48

Anti-17beta-hydroxy-17-(3-hydroxyprop-1(Z)-enyl)-11beta,19-(4-dimethylamino-o-phenylene)-4-androsten-3-oxime and Example 49

Syn-17beta-hydroxy-17-(3-hydroxyprop-1(Z)-enyl)-11beta,19-(4-dimethylamino-o-phenylene)-4-androsten-3-oxime Under protective gas, 1.15 g of the ketone prepared under example 17a) is put into 9 ml of absolute methylene chloride and mixed in succession with 28 ml of pyridine and 260 mg of hydroxylaminohydrochloride. After 3-hour stirring at room temperature the reaction mixture is poured onto saturated sodium bicarbonate solution and the aqueous phase is extracted with methylene chloride. The combined organic phases were dried on sodium sulfate and concentrated by evaporation in a vacuum. The residue is chromatographed on silica gel with a mixture of ethyl acetate/hexane and 453 mg of the antioxime and, as by-product, 287 mg of the synoxime are obtained.

48: $^1$H-NMR (CDCl$_3$) [ ]7.26 (1H, d J=9 Hz, proton on C-6 of the aromatic substance); 6.64 (1H, dd J=9 and J=2.5 Hz, proton on C-5 of the aromatic substance); 6.42 (1H,d J=2.5 Hz, proton on C-3 of the aromatic substance);5.9 (1H,s, H-4); 5.62–5.8 (2H,m,H-20 and H-21); 4.23–4.4 (2H,m, protons on C-22); 2.9 (6H,s,protons of dimethylamino group); 0.5 (3H,s,protons on C-18)

49: $^1$H-NMR (CDCl$_3$) [ ]: 7.25 (1H, d J=9 Hz,proton on C-6 of the aromatic substance); 6.6–6.7 (2H,m,H-4 and proton on C-5 of the aromatic substance); 6.42. (1H, d J=2 Hz, proton on C-3 of aromatic substance); 5.6–5.8 (2H,m,H-20 and H-21); 4.2–4.41 (2H, m, protons on C-22); 2.9 (6H,s,protons of the dimethylamino group); 0.5 (3H,s,protons on C-18)

Example 50

17beta-Hydroxy-17-(3-hydroxyprop-1(Z)-enyl)-11beta,19-(4-dimethylamino-o-phenylene)-1,4-androstadien-3-one a) 17beta-Trimethylsilyloxy-17-(3-trimethylsilyloxyprop-1(Z)-enyl) -11beta, 19-(4-dimethylamino-o-phenylene)-3-trimethylsilyloxy-2,4-androstadiene 2 g of the compound prepared according to example 17, dissolved in 60 ml of absolute tetrahydrofuran, is instilled in a solution of 43 mmol of lithium diisopropylamide in 200 ml of absolute tetrahydrofuran under protective gas at 0° C. Then chlorotrimethylsilane (10.6 ml) is instilled in the reaction mixture. After 30-minutes stirring, the reaction solution is poured onto ice-cold saturated sodium bicarbonate solution, the aqueous phase is extracted with ethyl acetate and the organic phase is successively washed with water and ammonium chloride solution. After drying on sodium sulfate, the organic phase is concentrated by evaporation in a vacuum. 3.38 g of silylenol ether is obtained as raw product.

b) 17beta-Trimethylsilyloxy-17-(3-trimethylsilyloxyprop-1(Z)-enyl)-11beta,19-(4-dimethylamino-o-phenylene)-1,4-androstadien-3-one 3.38 g of the silylenol ether prepared under a) is suspended as raw product in 40 ml of absolute acetonitrile and mixed with 1.4 g of palladium(II) acetate. After 1-hour more stirring at room temperature, the reaction mixture is suctioned off over Celite and the filtrate is concentrated by evaporation in a vacuum. 3.3 g of the above-mentioned dienone is obtained as raw product.

c) 17beta-Hydroxy-17-(3-hydroxyprop-1(Z)-enyl)-11beta,19-(4-dimethylamino-o-phenylene)-1,4-androstadien-3-one 3.3 g of the dienone prepared under b) is dissolved in 40 ml of absolute methanol and mixed with 3 g of anhydrous potassium carbonate. Under protective gas, the reaction mixture is stirred for 1 more hour at room temperature, then poured on to saturated sodium chloride solution and the aqueous phase is extracted several times with methylene chloride. The combined organic phases are washed with saturated sodium chloride solution, dried on sodium sulfate and concentrated by evaporation in a vacuum. Chromatography of the residue on silica gel with a mixture of ethyl acetate/hexane results in 752 mg of the title compound as yellowish foam.

$[\alpha]_D^{22} = -95°$ (CHCl$_3$; c=0.44)

Example 51

17beta-Hydroxy-17-ethinyl-11beta,19-(4-methoxy-o-phenylene)-4-androsten-3-one a) 17-Ethinyl-11beta,19-(4-methoxy-o-phenylene)-3,3-(2,2-dimethyltrimethylenedioxy)-androstane-5alpha,17beta-diol Analogously to the directions described under example 46e), 10 g of the keto compound prepared under example 4c) is converted into the corresponding 17alpha-ethinyl compound. 9.7 g of the above-mentioned compound is obtained as white foam.

b) 17beta-Hydroxy-17-ethinyl-11beta,19-(4-methoxy-o-phenylene)-4-androsten-3-one Analogously to the directions described under example 1c), 9.5 g of the ethinyl compound prepared under a) is reacted. 6.3 g of the title compound is obtained.

$[\alpha]_D^{22} = 39°$ (CDCl$_3$; c=0.5); mp=248°-151° C.
(ethyl acetate)

Example 52

17beta-Hydroxy-17-ethinyl-11beta,19-(4-methoxy-o-phenylene)-1,4-androstadien-3-one a) 17beta-Trimethylsilyloxy-17-(2-trimethylsilylethinyl)-11beta,19-(4-methoxy-o-phenylene)-3-trimethylsilyloxy-2,4androstadiene Analogously to the directions described under example 50a), 1 g of the keto compound prepared under example 51 is converted into the corresponding silylenol ether. 1.54 g of the above-mentioned compound is obtained as raw product.

b) 17beta-Trimethylsilyloxy-17-(2-trimethylsilylethinyl)-11beta,19-(4-methoxy-o-phenylene)-1,4-androstadien-3-one Analogously to the directions described under example 50b), 1.54 g of the silylenol ether prepared under a) is converted into the corresponding dienone. 1.32 g of the above-mentioned compound is obtained as raw product.

c) 17beta-Hydroxy-17-ethinyl-11beta,19-(4-methoxy-o-phenylene)-1,4-androsten-3-one Analogously to the directions described under example 50c), 1.34 g of the dienone prepared under b) is converted into the title compound. 720 mg of the above-mentioned compound is isolated as white foam.

$[\alpha]_D^{22} = -131°$ (CHCl$_3$; c=0.5);
mp=decomposition at 300°-304° C. (ethyl acetate)

Example 53

17beta-Hydroxy-17-(2-bromoethinyl-11beta,19-(4-methoxy-o-phenylene)-4-androsten-3-one 0.5 g of the acetylene prepared under example 51 is stirred for 30 minutes together 250 mg of N-bromosuccinimide and 21 mg of silver nitrate in 9 ml of acetone. Then the reaction mixture is filtered over Celite, the filter cake is thoroughly rewashed with methylene chloride, the filtrate is mixed with water and the aqueous phase is extracted several times with methylene chloride. The combined organic phases are washed with saturated sodium chloride solution, dried on sodium sulfate and concentrated by evaporation in a vacuum. The raw product is taken up in ethyl acetate and purified by crystallization. 421 mg of the title compound is obtained.

$[\alpha]_D^{22} = -11°$ (CHCl$_3$; c=0.5); mp 32 223°-225° C.
(ethyl acetate)

Example 54

11beta,19-(4-Dimethylamino-o-phenylene)-4-androsten-[17(beta-1')-spiro-5']-2',5'-dihydrofuran-3-one At 0° C., 1 g of the steroid obtained under example 17 is put into 30 ml of absolute methylene chloride and mixed with 3 ml of triethylamine. After addition of 0.42 ml of methane sulfonic acid chloride the reaction mixture is stirred at 0° C. for one more hour. Then it is poured on saturated sodium bicarbonate solution and the aqueous phase is extracted with methylene chloride. The combined organic phases are dried on sodium sulfate and concentrated by evaporation in a vacuum. The residue is chromatographed on silica gel with a mixture of ethyl acetate/hexane and 752 mg of the title compound is obtained as white foam.

$[\alpha]_D^{22} = 83°$ (CHCl$_3$; c=0.5)

Example 55

17beta-Hydroxy-17-(3-hydroxypropyl)-11beta,19-(4-dimethylamino-o-phenylene)-4-androsten-3-one a) 17-[3-(Tetrahydropyran-2-yloxy)-propyl]-11beta,19-(4-dimethylamino-o-phenylene)-3,3-(2,2-dimethyltrimethylenedioxy)-androstan-5alpha,17beta-diol 5 g of the steroid prepared under example 16a) is put into 100 ml of ethanol and mixed with 0.5 g palladium/carbon (10%). Then it is stirred under normal pressure of a hydrogen atmosphere until one equivalent of hydrogen is taken up. Then the reaction solution is filtered over Celite, the filter cake is thoroughly rewashed with methylene chloride and the filtrate is concentrated by evaporation in a vacuum. The residue is chromatographed on aluminum oxide (neutral, stage III) with a mixture of ethyl acetate/hexane and thus 4.55 g of the above-mentioned compound is obtained as white foam.

b) 17beta-Hydroxy-17-(3-hydroxypropyl)-11beta,19-(4-dimethylamino-o-phenylene)-4-androsten-3-one Analogously to the directions described under example 1c), 4.5 g of the hydroxypropyl compound prepared under a) is reacted. 2.49 g of the title compound is obtained.

$[\alpha]_D^{22} = 81°$ (CHCl$_3$; c=0.5); mp=132°-135° C.
(ethyl acetate)

Example 56

11beta,19-(4-Dimethylamino-o-phenylene)-4-androsten-[17(beta-1')-spiro-5']-tetrahydrofuran-3-one Under 0° C., 1 g of the steroid obtained under example 55 is put into 30 ml of absolute methylene chloride and mixed with 3 ml of triethylamine. After addition of 0.42 ml of methane sulfonic acid chloride the reaction mixture is stirred for 2 more hours at room temperature. Then it is poured onto saturated sodium bicarbonate solution and the aqueous phase is extracted with methylene chloride. The combined organic phases are dried on sodium sulfate and concentrated by evaporation in a vacuum. The residue is chromatographed on silica gel with a mixture of ethyl acetate/hexane and 691 mg of the title compound is obtained.

$[\alpha]_D^{22} = 80°$ (CHCl$_3$; c=0.515); melting point=172°-175° C. (diisopropyl ether)

Example 57

17beta-Hydroxy-17-ethinyl-11beta,19-(4-ethyl-o-phenylene)-4-androsten-3-one a)     11beta,19-(4-Ethyl-o-phenylene)-4-androsten-3,17-one Analogously to the directions described under example 1c), 15 g of the keto compound prepared under example 24a) is reacted. 8.3 g of the above-mentioned compound is obtained as white foam.

b)     11beta,19-(4-Ethyl-o-phenylene)-3-ethoxy-3,5-androstadien-17-one 8.2 g of the dione prepared under a) is dissolved in 500 ml of methylene chloride and, under protective gas, is mixed with 1.32 ml of absolute ethanol, 10 ml of triethylorthoformate and 160 mg of p-toluenesulfonic acid (dihydrate). After 4-hour stirring with ice-bath cooling the mixture is mixed with a little pyridine and then poured onto saturated sodium bicarbonate solution. The aqueous phase is separated and extracted with methylene chloride. The organic phases are washed with saturated sodium chloride solution, dried on sodium sulfate and concentrated by evaporation in a vacuum. 8.3 g of the raw product, whose purity is sufficient for further reaction, is obtained.

c)     17-Ethinyl-11beta,19-(4-ethyl-o-phenylene)-3-ethoxy-3,5-androstadien-17beta-ol Analogously to the directions described under example 46e), 10 g of the keto compound prepared under b) is converted into the corresponding 17alpha-ethinyl compound. 8.3 g of the above-mentioned compound is obtained as white foam.

d)     17beta-hydroxy-17-ethinyl-11beta,19-(4-ethyl-o-phenylene)-4-androsten-3-one Analogously to the directions described under example 1c), 2.8 g of the ethinyl compound prepared under c) is reacted. 1.98 g of the title compound is obtained.

$[\alpha]_D^{22} = 4520$ (CHCl$_3$; c=0.5); melting point=242°-248° C. (ethyl acetate)

Example 58

17beta-Hydroxy-17-ethinyl-11beta,19-(4-ethyl-o-phenylene) -4,6-androstadien-3-one Analogously to the directions described under example 3d), 5.3 g of the ethinyl compound prepared under example 57c) is reacted. 3.45 g of the title compound is obtained as yellowish foam.

$[\alpha]_D^{22} = 161°$ (CHCl$_3$; c=0.52)

Example 59

17beta-Hydroxy-17-ethinyl-11beta,19-(4-ethyl-o-phenylene) -6-chloro-4,6-androstadien-3-one a)     17beta-Hydroxy-17-ethinyl-11beta,19-(4-ethyl-o-phenylene)-6alpha,7alpha-epoxy-4-androsten-3-one 1.86 g of m-chloroperbenzoic acid (68%) is added to a solution of 2 g of the dienone prepared under example 58 in 100 ml of absolute methylene chloride at 0° C. Then the reaction mixture is heated to room temperature and stirred for 24 more hours. It is diluted with methylene chloride, the organic phase is successively washed with saturated sodium thiosulfate solution, 5% sodium hydroxide solution and water, dried on sodium sulfate and concentrated by evaporation in a vacuum. The residue is chromatographed on silica gel with a mixture of ethyl acetate/hexane. 802 mg of the above-mentioned epoxide is obtained as a white foam.

b)     7alpha,17beta-Dihydroxy-17-ethinyl-11beta,19-(4-ethyl-o-phenylene) -6beta-chloro-4,6-androstadien-3-one 750 mg of the epoxide prepared under a) is put into 15 ml of glacial acetic acid, mixed with 1.5 g of lithium chloride and stirred for 30 minutes at room temperature. Then the reaction mixture is poured onto water and the aqueous phase is extracted with methylene chloride. The combined organic phases are washed with saturated sodium chloride solution, dried on sodium sulfate and concentrated by evaporation in a vacuum. Final solvent residues are removed azeotropically with toluene. 947 mg of the above-mentioned compound is obtained as raw product.

c)     17beta-Hydroxy-17-ethinyl-11beta,19-(4-ethyl-o-phenylene)-6-chloro-4,6-androstadien-3-one 1.14 g of 4-dimethylaminopyridine and 0.71 ml of trifluoromethane sulfonic acid anhydride, dissolved in 4.5 ml of absolute methylene chloride, are added to a solution of 900 mg of the chlorohydrin prepared under b) in 25 ml of absolute methylene chloride at −78° C. Then the reaction mixture is heated to 0° C. and stirred for 2 more hours at this temperature. Then it is poured onto saturated sodium bicarbonate solution and the aqueous phase is extracted several times with methylene chloride. The combined organic phases are washed with saturated sodium chloride solution, dried on sodium sulfate and concentrated by evaporation in a vacuum. The residue is chromatographed on silica gel with a mixture of ethyl acetate/hexane and 459 g of the title compound is obtained as yellowish foam.

$[\alpha]_D^{22} = 163°$ (CHCl$_3$; c=0.515)

Example 60

17beta-Hydroxy-17-vinyl-11beta,19-(4-ethyl-o-phenylene)-4,6-androstadien-3-one

Analogously to the directions described under example 5b), 700 mg of the ethinyl compound prepared under example 58 is reacted. 497 mg of the title compound is obtained after chromatography on silica gel with a mixture of ethyl acetate/hexane.

$[\alpha]_D^{22} = 247°$ (CHCl$_3$; c=0.51); melting point=194°-196° C. (ethyl acetate)

Example 61

17beta-Hydroxy-11beta,19-(4-iodo-o-phenylene)-4-androsten-3-one a)     11beta,19-(4-iodo-o-phenylene)-3,3-(2,2-dimethyl-trimethylenedioxy)-androstane-5alpha,17beta-diol 300 mg of the tin compound prepared under example 39alpha) is dissolved in 15 ml of absolute methylene chloride and mixed with 456 mg of iodine. After one more hour stirring, the reaction mixture is poured onto saturated sodium thiosulfate solution and the aqueous phase is extracted with methylene chloride. The combined organic phases are dried on sodium sulfate and concentrated by evaporation in a vacuum. The residue is chromatographed on aluminum oxide (neutral, stage III) with a mixture of ethyl acetate/hexane and 196 mg of the above-mentioned compound is obtained as yellowish foam.

b) 17beta-Hydroxy-11beta,19-(4-iodo-o-phenylene)-4-androsten-3-one

Analogously to the directions described under example 1c) 180 mg of the iodine compound prepared under a) is reacted. 118 mg of the title compound is obtained as yellowish foam.

$^1$H-NMR (CDCl$_3$) [$\delta$]: 7.48 (1H,dd,J=1.5 and J=8 Hz,proton on C-5 of the aromatic substance); 7.42, (1H, s,proton on C-3 of the aromatic substance); 7.19 (1H, d J=8 Hz, proton on C-6 of the aromatic substance); 5.87 (1H,s,H-4); 3.62-3.74 (1H,q, J=7.5 and J =15 Hz, H-17 ); 0.27 (3H, s, protons on C-18)

Example 62

17-(Prop-1-inyl)-17beta-hydroxy-11beta,19-(4-cyano-o-phenylene)-4-androsten-3-one a) 11beta,19-(4-cyano-o-phenylene)-3,3-(2,2-dimethyl-trimethylenedioxy)-androstane-5alpha,17beta-diol 800 mg of the triflate obtained under example 26b) is dissolved in 2.5 ml of absolute tetrahydrofuran and under protective gas is mixed with 15 mg of palladium tetrakistriphenylphosphine and 98 mg of potassium cyanide. The reaction mixture is refluxed for 40 hours, then cooled to room temperature and filtered over Celite. The filter cake is thoroughly rewashed with methylene chloride, the filtrate is concentrated by evaporation in a vacuum and the residue is chromatographed on aluminum oxide (neutral, stage III) with a mixture of ethyl acetate/hexane. 455 mg of above-mentioned compound is isolated as yellowish foam.

b) 17-(Prop-1-inyl)-11beta,19-(4-cyano-o-phenylene)-3,3-(2,2-dimethyltrimethylenedioxy)-androstan-5alpha,17beta-diol Analogously to the directions described under example 2b), 425 mg of the keto compound prepared under a) is converted into the corresponding 17alpha-propinyl compound. 355 mg of the above-mentioned compound is obtained as white foam.

c) 17beta-Hydroxy-17-(prop-1-inyl)-11beta,19-(4-cyano-o-phenylene)-4-androsten-3-one Analogously to the directions described under example 1c) 350 mg of the propinyl compound prepared under b) is reacted. 224 mg of the title compound is obtained.

$[\alpha]_D^{22}=33°$ (CHCl$_3$; c=0.5); melting point=232°-235° C. (ethyl acetate/diisopropylether)

Example 63

17bet a-Hydroxy-17-ethinyl-11beta,19-(4-ethyl-o-phenylene) -7alpha-methyl-androsten-3-one 150 mg of copper(I) chloride is added to 30 ml of a 1-m solution of methylmagnesium iodide solution in diethyl ether in an ice-cold bath. After stirring for 15 more minutes, a solution of 1.24 g of the dienone prepared under example 58 is instilled in 15 ml of absolute tetrahydrofuran. The reaction mixture is stirred for 2 more hours and then poured onto saturated ammonium chloride solution. The aqueous phase is extracted with ethyl acetate, the organic phase is washed with dilute ammonia solution and saturated sodium chloride solution, dried on sodium sulfate and concentrated by evaporation in a vacuum. The residue is chromatographed on silica gel with a mixture of ethyl acetate/hexane. 453 mg of the of the title compound is isolated. $[\alpha]_D^{22}=33°$ (CHCl$_3$; c=0.5); melting point=260°-264° C. (ethyl acetate)

Example 64

17beta-Hydroxy-17-ethinyl-11beta, 19-(4-methoxy-o-phenylene)-6-methylene-4-androsten-3-one 834 mg of the enone obtained according to example 51 is dissolved in 22 ml of absolute chloroform and successively mixed with 738 mg of anhydrous sodium acetate, 14.4 ml of formaldehyde diethyl acetal and 2.8 ml of phosphoryl chloride. The reaction mixture is then refluxed for 1 hour, neutralized with sodium carbonate solution and the aqueous phase is extracted with methylene chloride, the combined organic phases are washed with water, dried on sodium sulfate and concentrated by evaporation in a vacuum. The residue is chromatographed on silica gel with a mixture of ethyl acetate/hexane and 347 mg of the title compound is obtained as yellowish foam.

$^1$H-NMR (CD$_2$Cl$_2$) [$\alpha$]: 7.32 (1H,dJ=9 Hz, proton on C-6 of the aromatic substance); 6.75 (1H, dd J=9 and J=2,5 Hz, proton on C-5 of the aromatic substance ); 6.59 (1H, d J=2.5 Hz, proton on C-3 of the aromatic substance); 6.01 (1H,s,H-4); 5.2 and 5.03 (respectively: 1H,tr J=1.5 Hz, proton of the exomethylene group); 3.75 (3H,s,protons of the methyl ether group; 0.39 (3H,s,protons on C-18)

Example 65

11beta,19-(4-Dimethylamino-o-phenylene)-4-pregnene-3,20-dione a) 17beta-Cyano-11$\beta$,19-(4-dimethylamino-o-phenylene)-3,3-(2,2-dimethyltrimethylenedioxy)-androstan-5alpha-ol 1.9 g of the steroid prepared according to example 13c) is dissolved under protective gas in 250 ml of absolute dimethoxyethane and mixed at room temperature with 12.5 g of potassium-t-butylate and 1.85 ml of t-butanol. 2.16 g of p-tolylsulfonylmethylisocyanide, dissolved in 50 ml of absolute dimethoxyethane, is slowly instilled in this mixture over 2 hours. After stirring for 30 more minutes, the reaction mixture is poured onto cold saturated ammonium chloride and the aqueous phase is extracted with methylene chloride. The combined organic phases are washed with saturated sodium chloride solution, dried on sodium sulfate and concentrated by evaporation in a vacuum. After chromatography on aluminum oxide (neutral, stage III) with a mixture of ethyl acetate/hexane, 1.67 g of the above-mentioned nitrile is obtained as yellowish foam.

b) 11beta, 19-(4-Dimethylamino-o-phenylene)-4-pregnene-3,20-dione 1.5 g of the nitrile obtained under a) is put into 36 ml of absolute tetrahydrofuran under protective gas at 0° C. and mixed with 18 ml of a 1.6 m methyllithium solution (diethyl ether). After stirring for 1.5 more hours, the reaction mixture is poured onto cold saturated ammonium chloride solution and the aqueous phase is extracted with ethyl acetate. The combined organic phases are washed with water, dried on sodium sulfate and concentrated by evaporation in a vacuum. 1.24 g of raw product is obtained.

1.24 g of the obtained raw product is dissolved in 120 ml of acetone and mixed, under protective gas, with 7.5 ml of 4 n of aqueous hydrochloric acid. After 2-hour stirring at 40° C., the reaction mixture is poured onto cold saturated sodium bicarbonate solution and the aqueous phase is extracted several times with methylene chloride. The combined organic phases are dried on sodium sulfate and concentrated by evaporation in a vacuum. The residue is chromatographed on silica gel with a mixture of ethyl acetate/hexane. 764 mg of the title compound is obtained as yellowish foam.

$^1$H-NMR (CD$_2$Cl$_2$) [α]: 7.24 (1H, d J=9 Hz, proton 9 on C-6 of the aromatic substance);6.61 (1h,dd J=9 and J=2,5 Hz,proton on C-5 of the aromatic substance); 6.42 (1H,d J=2, 5 Hz,proton on C-3 of the aromatic substance); 5.8 (1H,s,H-4); 2.9 (6H,s, protons of dimethylamino group); 2.18 (3H,s,protons on C-21); 0.18 (3H,s, protons on C-18)

Example 66

17-(Prop-1-inyl)-17beta-hydroxy-11beta,19-(4-dimethylamino-o-phenylene)-4,6-androstadien-17beta-ol a) 17-(Prop-1-inyl)-11beta,19-(4-dimethylamino-o-phenylene)-3-ethoxy-3,5-androstadien-17beta-ol Starting from 8 g of the keto compound obtained according to example 13c), by acid cleavage, according to directions 1c), of 5.4 g of 11beta,19-(4-dimethylamino-o-phenylene)-4-androstene-3,17-dione, by enol ether formation, according to directions 57b), of 3.14 g of 11beta,19-(4-dimethylamino-o-phenylene)-3-ethoxy-3,5-andostadien-17-one and propine addition, according to the directions of example 2b), 3.56 g of the above-mentioned compound is obtained as raw product.

b) 17-(Prop-1-inyl)-17beta-Hydroxy-11beta,19-(4-dimethylamino-o-phenylene-6beta-bromo-4-androsten-3-one 3.5 g of the steroid obtained under a) is dissolved in 350 ml of methylene chloride and mixed with 1.2 ml triethylamine. Then the solution is cooled to −50° C. and mixed at this temperature with 1.44 g of N-bromosuccinimide. After stirring for 15 more minutes at −50° C., the reaction mixture is heated to 0° C. and mixed with saturated sodium thiosulfate solution. Then the aqueous phase is separated and extracted with methylene chloride. The combined organic phases are washed with saturated ammonium chloride solution, dried on sodium sulfate and concentrated by evaporation in a vacuum. After chromatography on silica gel with a mixture of ethyl acetate/hexane, 1.62 g of the title compound is obtained as white foam.

c) 17(Prop-1-inyl)-17beta-Hydroxy-11beta,19-(4-dimethylamino-o-phenylene)-4,6-androstadien-3-one 1.6 g of the 6beta-bromine compound prepared under b) analogously to the conditions described under example 3d) is converted with lithium carbonate into the dienone. 1.19 g of the title compound is obtained.

$[α]_D^{22}$=177° (CHCl$_3$; c=0.5); melting point=244°-246° C. (ethyl acetate)

Example 67

17beta-Hydroxy-17-ethinyl-11beta,19-(4-ethyl-o-phenylene)-1,4-androstadien-3-one Analogously to example 50, 2 g of the enone obtained according to example 57 is converted into 741 mg of the title compound by way of 17beta-trimethylsilyloxy-17-(2-trimethylsilylethinyl)-11beta,19-(4-ethyl-o-phenylene)-3-trimethylsilyloxy-2,4-androstadiene and 17beta-trimethylsilyloxy-17-(2-trimethylsilylethinyl)-11beta,19-(4-ethyl-o-phenylene)-1,4-androstadien-3-one as intermediate steps.

$[α]_D^{22}$=−144° C. (CHCl$_3$; c=0.5); melting point=262°-270° C. (ethyl acetate)

Example 68

17beta-Hydroxy-17-(prop-1-inyl)-11beta,19-(4-ethyl-o-phenylene)-1,4-androstadien-3-one Analogously to example 50, 1 g of the enone obtained according to example 24 is converted into 306 mg of the title compound by way of 17beta-trimethylsilyloxy-17-(prop-1-inyl)-11beta,19-(4-ethyl-o-phenylene)-3-trimethylsilyloxy-2,4-androstadiene and 17beta-trimethylsilyloxy-17-(prop-1-inyl)-11beta,19-(4-ethyl-o-phenylene)-1,4-androstadine-3-one as intermediate steps.

$[α]_D^{22}$=−142° CHCl$_3$; c=0.52); mp=decomposition at 275°-280° C. (ethyl acetate)

Example 69

17beta-Hydroxy-17-(prop-1-inyl)-11beta,19-[4-(4-cyanophenyl)-o-phenylene]-4-androsten-3-one Analogously to example 43, starting from 1.5 g of the trifluorate prepared according to example 26b), 373 mg of the title compound is obtained as white foam by way of 11beta,19-[4(4-cyanophenyl)-o-phenylene]-5alpha-hydroxy-3,3-( 2,2-dimethyltrimethylenedioxy)-androstan-17-one and 17-(prop-1-inyl)-11beta,19-[4-(4-cyanophenyl)-o-phenylene]-3,3-(2,2-dimethyltrimethylenedioxy)-androstane-5alpha,17beta-diol as intermediate steps.

$[α]_D^{22}$=76° (CHCl$_3$; c=0.5)

Example 70

17beta-Hydroxy-17-(prop-1-inyl)-11beta,19-[4-(2-thiazolyl)-o-phenylene]-4-androsten-3-one Analogously to example 43, starting from 1.5 g of the trifluoate prepared according to example 26b), 173 mg of the title compound is obtained as white foam by way of 11beta,19-[4-(2-thiazolyl)-o-phenylene]-5alpha-hydroxy-3,3-(2,2-dimethyltrimethylenedioxy)-androstan-17-one and 17-(prop-1inyl)-11beta,19-[4-(2-thiazolyl)-o-phenylene]-3,3-(2,2-dimethyltrimethylenedioxy)-androstan-5alpha,17beta-diol as intermediate steps.

$[α]_D^{22}$=41° (CHCl$_3$; c=0.5)

Example 71

17beta-Hydroxy-17-(prop-1-inyl)-11beta,19-[4-(3-pyridyl)-o-phenylene]-4-androsten-3-one Analogously to example 43, starting from 1.5 g of the trifluoate prepared according to example 26b), 254 mg of the title compound is obtained as white foam by way of 11beta,19-[4-(3-pyridyl)-o-phenylene]-5alpha-hydroxy-3,3-(2,2-dimethyltrimethylenedioxy)-androstan-17-one and 17-(prop-1inyl)-11beta,19-[4-(3-pyridyl)-o-phenylene]-3,3-(2,2-dimethyltrimethylenedioxy)-androstane-5alpha, 17beta-diol as intermediate steps.

$[α]_D^{22}$32 51° 51° (CHCl$_3$; c=0.505)

Example 72

17beta-Hydroxy-17-(prop-1-inyl)-11beta,19-(3-ethinyl-o-phenylene)-4-androsten-3-one a) 11beta,19-(3-hydroxy-o-phenylene)-3,3-(2,2-dimethyltrimethylenedioxy)-androstane-5alpha,17beta-diol 4 g of the methylenedioxy compound obtained according to example 45b) is dissolved in 300 ml of tetrahydrofuran and is added, at −78° C., to 600 mg of lithium, dissolved in 160 ml of liquid ammonia, the reaction mixture is slowly heated to −40° C. over three hours, then the excess lithium is decomposed by addition of ethanol and the ammonia is evaporated. The remaining phase is mixed with water and the aqueous phase is extracted with ethyl acetate. The combined organic phases are dried on sodium sulfate and concentrated by evaporation in a vacuum. After chromatography of the residue on silica gel with a mixture of ethyl acetate/hexane, 2.38 g of the above-mentioned compound is obtained. In addition, 0.45 g of the 4-hydroxy compound already prepared under example 18a) is isolated as by-product.

b) 11beta,19-(3-trifluoromethylsulfonyloxy-o-phenylene)-3,3-(2,2-dimethyltrimethylenedioxy)-androstane-5alpha,17beta-diol Analogously to the directions described under example 19a) 2.3 g of the 3-phenol obtained under a) is reacted with trifluoromethanesulfonic acid anhydride to obtain 1.67 g of the above-mentioned compound.

c) 17beta-Hydroxy-17-(prop-1-inyl)-11beta,19-(3-ethinyl-o-phenylene)-4-androsten-3-one 207 mg of the title compound is prepared by coupling of 1.6 g of the trifluorate with ethinyltrimethylsilane analogously to the directions of example 20a) to 11beta,19-[3-(2-trimethylsilylethinyl)-o-phenylene]-3,3-(2,2-dimethyltrimethylenedioxy)-androstane-5alpha,17beta-diol, chromotrioxidation analogously to the directions of example 21c) to 11beta,19-[3-(2-trimethylsilyethinyl)-o-phenylene]-5alpha-hydroxy-3,3-(2,2-dimethyltrimethylenedioxy)-androstan-17beta-one, desilylation analogously to the directions of 22a) to 11beta,19-(3-ethinyl-o-phenylene)-5alpha-hydroxy-3,3-(2,2-dimethyltrimethylenedioxy)-androstan-17beta-one, propine addition analogously to the directions of example 22b) to 17-(prop-1-inyl)-11beta,19-(3-ethinyl-o-phenylene)-3,3-(2,2-dimethyltrimethylenedioxy)-androstane-5alpha,17beta-diol and its cleavage analogously to the directions of 1c).

$[\alpha]_D^{22} = 32°$ (CHCl$_3$; c=0.5)

Example 73

17-(Prop-1(2)-enyl)-17beta-hydroxy-11beta,,19-(3-bromo-4-dimethylamino-o-phenylene)-4-androsten-3-one 1.5 g of the steroid obtained under example 17 is dissolved in 150 ml of methylene chloride and mixed with 4.7 ml of triethylamine. Then the solution is cooled to 0° C. and at this temperature is mixed with 578 mg of N-bromosuccinimide. After stirring for 3 more hours at 0° C., the reaction mixture is mixed with saturated sodium thiosulfate solution. Then the aqueous phase is separated and extracted with methylene chloride. The combined organic phases are washed with saturated sodium chloride solution, dried on sodium sulfate and concentrated by evaporation in a vacuum. After chromatography on silica gel with a mixture of ethyl acetate/hexane, 1.03 g of the title compound is obtained as yellowish foam.

$^1$H-NMR (CD$_2$Cl$_2$) [$\alpha$]: 7.39 (1H, d J=9 Hz, proton on C-6 of the aromatic substance); 7.0 (1H,d J=9, proton on C-5 of the aromatic substance); 5.85 (1H,s,H-4); 5.6-5.8 (2H,m,protons on C-20 and C-21); 2.75 (6H,s,protons of the dimethylamino group); 0.38 (3H,s,protons on C-18).

We claim:

1. A process comprising cyclizing a compound of formula

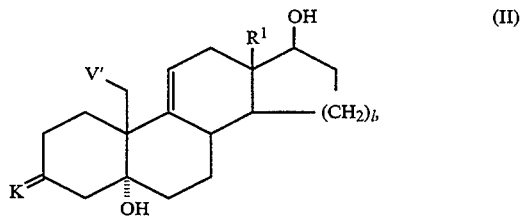

wherein $R^1$ is methyl or ethyl, l is 1 or 2, and

K is a blocked keto group in the form of ketal or thioketal,

V' is a phenyl ring of the formula

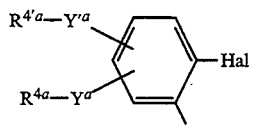

wherein

Hal is fluorine, chlorine, bromine or iodine;

$R^{4a}$ and $R^{4'a}$ being the same or different, are each hydrogen, —OR$^{11}$, —S(O)$_k$R$^{11}$, —N(O)$_n$R$^{11}$R$^{12}$, —O-SO$_2$R$^{13}$, —P(O)(OR$^{14}$)$_2$, —SiR$_3^{14}$ or —SnR$_3^{14}$;

k is 0, 1 or 2;

n is 0 or 1;

$R^{11}$ is hydrogen or C$_1$-C$_8$-alkyl;

$R^{12}$ is hydrogen, C$_1$-C$_8$ -alkyl, cyanide or C$_1$-C$_{10}$-acyl;

$R^{13}$ is perfluorated C$_1$-C$_4$-alkyl;

$R^{14}$ is C$_1$-C$_4$-alkyl;

$R^{11}$ and $R^{12}$, in an —N(O)$_n$R$^{11}$R$^{12}$ group, can together be, with the inclusion of N, a 5- or 6-member heterocyclic ring, which can contain another heteroatom N, O or S;

$Y^a$ and $Y'^a$ being the same or different, are each a direct bond, a straight-chain or branched alkylene group, which can contain double or triple bond(s), having up to 20 carbon atoms, which is unsubstituted or substituted by one or more oxo-, C$_1$-C$_{10}$-acyloxy-, —OR$^{11}$, —S(O)$_k$R$^{11}$ and/or —N(O)$_n$R$^{11}$R$^{12}$ groups;

$R^{4a}$-$Y^a$ and $R^{4'a}$-$Y'^a$ together are a saturated, unsaturated or aromatic, 5- or 6-member ring with 0 to 2 oxygen, sulfur atoms and/or NR$^{11}$ groups; or $R^{4'a}$-$Y'^a$ is H and $R^{4a}$-$Y^a$ is phenyl, naphthyl, 2 -methoxyphenyl, 3-methoxyphenyl, 4-methoxyphenyl, 2-tolyl, 3-tolyl, 4-tolyl, furyl-2, furyl-3, thienyl-2, thienyl-3, pyridyl-2, pyridyl-3, pyridyl-4, thiazoyl or imidazolyl;

with the proviso that k and n are each greater than 0 only if their respective $R^{11}$ group is $C_1$-$C_8$-alkyl, and wherein any hydroxy, mercapto, amino, oxo and/or terminal acetylene groups are protected; or is a 5- or 6-member heteroaromatic ring with 0 to 2 N, O or S atoms of the formula

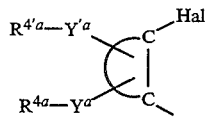

wherein

Hal, $R^{4a}$, $R^{4'a}$, $Y^a$ and $Y'^a$ are as defined above, wherein any hydroxy, mercapto, amino, oxo and/or terminal acetylene groups are protected, to obtain a compound according to formula IVa

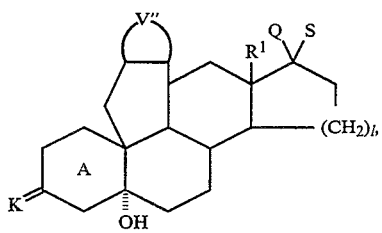

(IVa)

wherein

Q is β-hydroxy,

S is α-hydrogen,

K is a blocked keto group in the form of ketal or thioketal, l is b 1 or 2, $R^1$ is methyl or ethyl, and V″ is a phenyl radical according to the formula

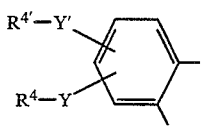

wherein $R^4$ and $R^{4'}$ being the same or different, are each hydrogen, —$OR^{11}$, —$S(O)_kR^{11}$, —$N(O)_nR^{11}R^{12}$, —O—$SO_2R^{13}$, —$p(O)(OR^{14})_2$, —$SiR_3^{14}$ or —$SnR_3^{14}$, k is 0, 1 or 2, n is 0 or 1, $R^{11}$ is hydrogen or $C_1$-$C_8$ -alkyl, $R^{12}$ is cyanide or $C_1$-$C_{10}$-acyl, $R^{13}$ is perfluorated $C_1$-$C_4$-alkyl, $R^{14}$ is $C_1$-$C_4$-alkyl, or $R^{11}$ and $R^{12}$, in an —$N(O)_nR^{11}R^{12}$ group, can also together be, with the inclusion of N, a 5- or 6-member heterocyclic ring, which can contain another heteroatom N, O or S, Y and Y', being the same or different, are each a direct bond or a straight-chain or branched alkylene group, which can contain double or triple bond(s), having up to 20 carbon atoms, and which is unsubstituted or substituted by one or more oxo-, $C_1$-$C_{10}$-acyloxy-, —$OR^{11}$, —$S(O)_kR^{11}$ and/or —$N(O)_nR^{11}R^{12}$;

$R^4$-Y and $R^{4'}$-Y' together are a saturated, unsaturated or aromatic, 5- or 6-member ring with 0 to 2 oxygen, sulfur atoms and/or $NR^{11}$; or $R^{4'}$-Y' is H and $R^4$-Y is phenyl, naphthyl, 2-methoxyphenyl, 3-methoxyphenyl, 4-methoxyphenyl, 2-tolyl, 3-tolyl, 4-tolyl, furyl-2, furyl-3, thienyl-2, thienyl-3, pyridyl-2, pyridyl-3, pyridyl-4, thiazoyl or imidazolyl;

wherein k and n are each greater than 0 only if their respective $R^{11}$ group is $C_1$-$C_8$-alkyl, or V″ is a five-or six-member heteroaromatic ring with 1 to 2 N, O or S atoms of the formula

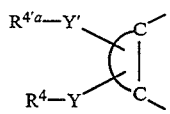

wherein $R^4$, $R^{4'}$, Y and Y' have the meanings indicated above; wherein any hydroxy, mercapto, amino, oxo and/or terminal acetylene groups present are protected.

2. A process according to claim 1, wherein V″ is

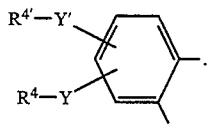

3. A process according to claim 2, further comprising, by use of a dehydrating agent, unblocking keto group K to form a 3-oxo group and a 4(5)-double bond.

4. A process according to claim 3, further comprising oxidizing β-hydroxy group Q to obtain a compound having a 17-oxo group.

5. A process according to claim 4, further comprising protecting the 3-oxo group with a protective group, and subsequently converting the D ring, to a ring of the formula

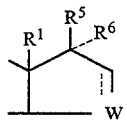

wherein

--- is a single or double bond,

W is —$CH_2$—, =CH—, —$CH_2CH_2$— or =$CHCH_2$—, $R^5$ and $R^6$ are, respectively, —$OR^7$ and —C≡C—U,

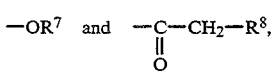

—$OR^7$ and —C—$CH_2$—$R^8$,
                    ‖
                    O

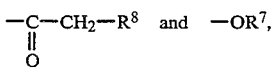

—C—$CH_2$—$R^8$ and —$OR^7$,
‖
O

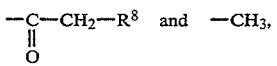

—C—$CH_2$—$R^8$ and —$CH_3$,
‖
O

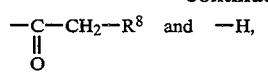

—OR$^7$ and —(CH$_2$)$_m$—CH$_2$—R$^9$,
—OR$^7$ and —CH=CH(CH$_2$)$_k$—CH$_2$—R$^9$,
—OR$^{10}$ and —H,
—OR$^{10}$ and —(CH$_2$)$_k$—C≡C—U, or
R$^5$ and R$^6$ together are

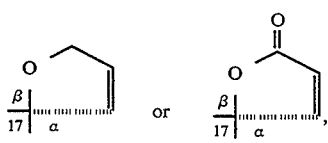

R$^7$ is hydrogen or C$_{m1}$-C$_4$-acyl,
U is hydrogen, halogen, or alkyl, hydroxyalkyl, alkoxyalkyl, or acyloxyalkyl with respectively 1 to 4 carbon atoms in the alkyl and acyl portions thereof,
R$^8$ is hydrogen, hydroxy, or alkyl, O-alkyl or O-acyl, each with respectively 1 to 4 C atoms,
R$^9$ is hydrogen, hydroxy, cyano, or O-alkyl or O-acyl, each with respectively 1 to 4 carbon atoms,
R$^{10}$ is hydrogen, or alkyl or acyl, each with respectively 1 to 10 carbon atoms,
m is 0, 1, 2 or 3, and
is 0, 1 or 2.

6. A process according to claim 5, further comprising removing said protective group from the 3-oxo group and functionalizing ring A to form a ring of the formula a)

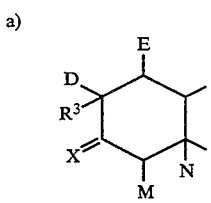

wherein
M and N together are a second bond or M is hydrogen and N is hydroxy,
X is oxygen, two hydrogen atoms, or N~OH,
R$^3$ and D, being the same or different, are hydrogen, nitrile or C$_1$-C$_4$-alkyl, or together are a methylene or ethylene group,
E is hydrogen or C$_1$-C$_4$-alkyl,
D and E together can also be a second bond between carbon atoms 1 and 2 or together are a methylene group,
wherein X is not oxygen when N is hydroxy and M, R$^3$, D and E are all each hydrogen, b)

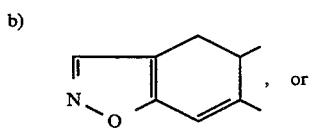, or c)

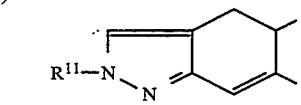

wherein
R$^{11}$ is as defined above.

7. A process according to claim 2, further comprising oxidizing β-hydroxy group Q to obtain a compound having a 17-oxo group.

8. A process according to claim 7, further comprising converting said 17-oxo group to form a D ring of the formula

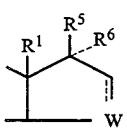

wherein
══ is a single or double bond,
W is —CH$_2$—, =CH—, —CH$_2$CH$_2$— or =CHCH$_2$—,
R$^5$ and R$^6$ are, respectively, —OR$^7$ and —C≡C—U,

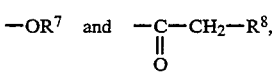

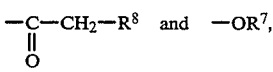

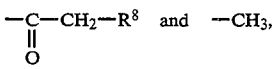

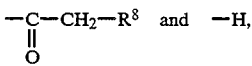

—OR$^7$ and —(CH$_2$)$_m$—CH$_2$—R$^9$,
—OR$^7$ and —CH=CH(CH$_2$)$_k$—CH$_2$—R$^9$,
—OR$^{10}$ and —H,
—OR$^{10}$ and —(CH$_2$)$_k$—C≡C—U, or
R$^5$ and R$^6$ together are

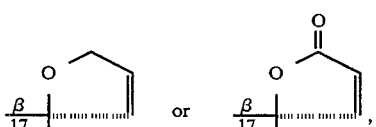

R$^7$ is hydrogen or C$_1$-C$_4$-acyl,
U is hydrogen, halogen, or alkyl, hydroxyalkyl, alkoxyalkyl, or acyloxyalkyl with respectively 1 to 4 carbon atoms in the alkyl and acyl portions thereof,
R$^8$ is hydrogen, hydroxy, or alkyl, O-alkyl or O-acyl, each with respectively 1 to 4 C atoms,
R$^9$ is hydrogen, hydroxy, cyano, or O-alkyl or O-acyl, each with respectively 1 to 4 carbon atoms,
R$^{10}$ is hydrogen, or alkyl or acyl, each with respectively 1 to 10 carbon atoms,
m is 0, 1, 2 or 3, and
k is 0, 1 or 2.

9. A process according to claim 8, further comprising, by use of a dehydrating agent, subsequently unblocking keto group K to form a 3-oxo group and a 4(5)-double bond.

10. A process according to claim 2, wherein said $R^4$-Y is a protected hydroxy group and said process further comprises converting said protected hydroxy group to a hydroxy group.

11. A process according to claim 10, wherein $R^4$-Y is —$OR^{11}$ and $R^{11}$ is $C_{1-8}$-alkyl, and —$OR^{11}$ is converted to —OH.

12. A process according to claim 10, further comprising, by use of a dehydrating agent, unblocking keto group K to form a 3-oxo group and a 4(5)-double bond.

13. A process according to claim 12, wherein hydroxy group $R^{4'}$-Y' is converted to —Y—$OSO_2R^{13}$ and —Y—$SO_2R^{13}$ is subsequently converted to —Y—$SiR_3{}^{14}$.

14. A process according to claim 10, wherein hydroxy group $R^4$—Y is subsequently converted to —Y—$OSO_2R^{13}$, —Y—$SiR_3{}^{14}$ or —Y—$SnR_3{}^{14}$.

15. A process according to claim 14, wherein hydroxy group $R^{4'}$-Y' is converted to —Y—$OSO_2R^{13}$ and —Y—$SO_2R^{13}$ is subsequently converted to —Y—$SiR_3{}^{14}$.

16. A process according to claim 14, further comprising oxidizing β-hydroxy group Q to obtain a 17-oxo group.

17. A process according to claim 16, further comprising converting the D ring, to a ring of the formula

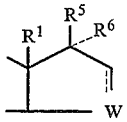

wherein
--- is a single or double bond,
W is —$CH_2$—, =CH—, —$CH_2CH_2$— or =$CHCH_2$—,
$R^5$ and $R^6$ are, respectively, —$OR^7$ and —C≡C—U,

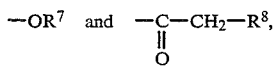

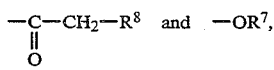

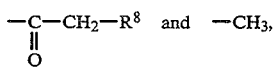

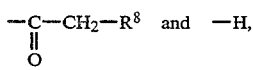

—$OR^7$ and —$(CH_2)_m$—$CH_2$—$R^9$,
—$OR^7$ and —CH=CH$(CH_2)_k$—$CH_2$—$R^9$,
—$OR^{10}$ and —H,
—$OR^{10}$ and —$(CH_2)_k$—C≡C—U, or
$R^5$ and $R^6$ together are

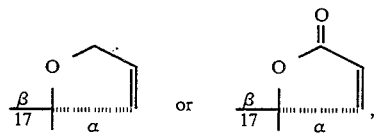

$R^7$ is hydrogen or $C_1$-$C_4$-acyl,
U is hydrogen, halogen, or alkyl, hydroxyalkyl, alkoxyalkyl, or acyloxyalkyl with respectively 1 to 4 carbon atoms in the alkyl and acyl portions thereof,
$R^8$ is hydrogen, hydroxy, or alkyl, O-alkyl or O-acyl, each with respectively 1 to 4 C atoms,
$R^9$ is hydrogen, hydroxy, cyanide, or O-alkyl or O-acyl, each with respectively 1 to 4 carbon atoms,
$R^{10}$ is hydrogen, or alkyl or acyl, each with respectively 1 to 10 carbon atoms,
m is 0, 1, 2 or 3, and
k is 0, 1 or 2.

18. A process according to claim 17, further comprising, by a dehydrating agent, unblocking keto group K to form a 3-oxo group and a 4(5)-double bond.

19. A process according to claim 17, wherein prior to converting the D ring, the $R^4$—Y— group is converted to —Y—H.

20. A process according to claim 7, wherein said $R^4$—Y is a protected hydroxy group and said process further comprises converting said protected hydroxy group to a hydroxy group.

21. A process according to claim 20, wherein hydroxy group $R^4$—Y is subsequently converted to —Y—$OSO_2R^{13}$ —Y—$SiR_3{}^{14}$ or —Y—$SnR_3{}^{14}$.

22. A process according to claim 21, further comprising converting the D ring, to a ring of the formula

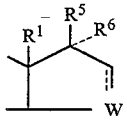

wherein
--- is a single or double bond, W is —$CH_2$—, =CH—, —$CH_2CH_2$— or =$CHCH_2$—, $R^5$ and $R^6$ are, respectively, —$OR^7$ and —C≡C—U,

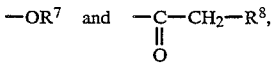

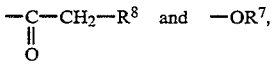

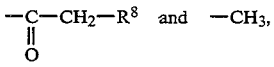

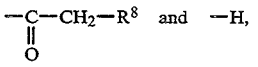

—$OR^7$ and —$(CH_2)_m$—$CH_2$—$R^9$,
—$OR^7$ and —CH=CH$(CH_2)_k$—$CH_2$—$R^9$,
—$OR^{10}$ and —H,
—$OR^{10}$ and —$(CH_2)_k$—C≡C—U, or
$R^5$ and $R^6$ together are

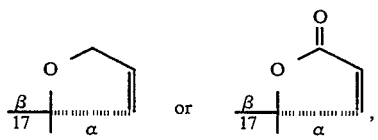

$R^7$ is hydrogen or $C_1$-$C_4$-acyl,

U is hydrogen, halogen, or alkyl, hydroxyalkyl, alkoxalkyl, or acyloxyalkyl with respectively 1 to 4 carbon atoms in the alkyl and acyl portions thereof, $R^8$ is hydrogen, hydroxy, or alkyl, O-alkyl or O-acyl, each with respectively 1 to 4 C atoms, $R^9$ is hydrogen, hydroxy, cyanide, or O-alkyl or O-acyl, each with respectively 1 to 4 carbon atoms, $R^{10}$ is hydrogen, or alkyl or acyl, each with respectively 1 to 10 carbon atoms, m is 0, 1, 2 or 3, and k is 0, 1 or 2.

23. A process according to claim 22, further comprising, by a dehydrating agent, unblocking keto group K to form a 3-oxo group and a 4(5)-double bond.

24. A process according to claim 23, wherein prior to converting the D ring, the $R^4$—Y— group is converted to —Y—H.

25. A process according to claim 7, further comprising, by use of a dehydrating agent, unblocking keto group K to form a 3-oxo group and a 4(5)-double bond.

26. A process according to claim 25, further comprising protecting the 3-oxo group with a protective group, and subsequently converting the D ring, to a ring of the formula

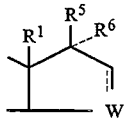

wherein

═ is a single or double bond,

W is —CH$_2$—, ═CH—, —CH$_2$CH$_2$— or ═CHCH$_2$, $R^5$ and $R^6$ are, respectively, —OR$^7$ and —C≡C—U,

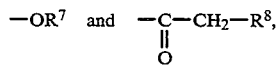

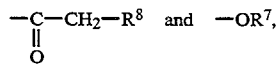

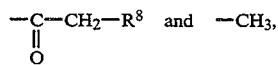

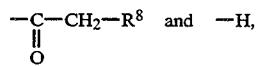

OR$^7$ and —(CH$_2$)$_m$—CH$_2$—R$^9$,

OR$^7$ and —CH═CH(CH$_2$)$_k$—CH$_2$—R$^9$,

—OR$^{10}$ and —H,

—OR$^{10}$ and —(CH$_2$)$_k$—C≡C—U, or $R^5$ and $R^6$ together are

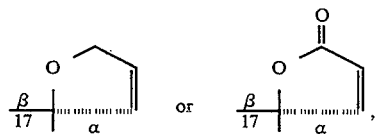

$R^7$ is hydrogen, or $C_1$-$C_4$-acyl,

U is hydrogen, halogen, or alkyl, hydroxylalkyl, alkoxyalkyl or acyloxyalkyl with respectively 1 to 4 carbon atoms in the alkyl and acyl portions thereof, $R^8$ is hydrogen, hydroxy, or alkyl, O-alkyl or O-acyl, each with respectively 1 to 4 C atoms, $R^9$ is hydrogen, hydroxy, cyano, or O-alkyl or O-acyl, each with respectively 1 to 4 carbon atoms, $R^{10}$ is hydrogen, or alkyl or acyl, each with respectively 1 to 10 carbon atoms, m is 0, 1, 2 or 3, and k is 0, 1 or 2.

27. A process according to claim 26, further comprising removing said protective group from the 3-oxo group and functionalizing ring A to form a ring of the formula

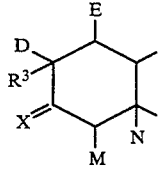

a)

wherein

M and N together are a second bond or M is hydrogen and N is hydroxy,

X is oxygen, two hydrogen atoms, or N~OH, $R^3$ and D, being the same or different, are hydrogen, nitrile or $C_1$-$C_4$-alkyl, or together are a methylene or ethylene group, E is hydrogen or $C_1$-$C_4$-alkyl, D and E together can also be a second bond between carbon atoms 1 and 2 or together are a methylene group, wherein X is not oxygen when N is hydroxy and M, $R^3$, D and E are all each hydrogen,

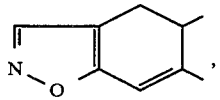

b)

or

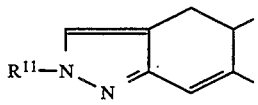

c)

wherein $R^{11}$ is as defined above.

28. A process according to claim 16, further comprising, by use of a dehydrating agent, unblocking keto group K to form a 3-oxo group and a 4(5)-double bond.

29. A process according to claim 28, further comprising protecting the 3-oxo group with a protective group, and subsequently converting the D ring, to a ring of the formula

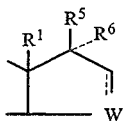

wherein
- ---- is a single or double bond,
- W is —CH$_2$—, =CH—, —CH$_2$CH$_2$— or =CHCH$_2$—,
- R$^5$ and R$^6$ are, respectively, —OR$^7$ and —C≡C—U,

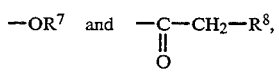

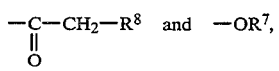

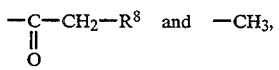

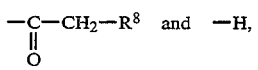

—OR$^7$ and —(CH$_2$)$_m$—CH$_2$—R$^9$,
—OR$^7$ and —CH=CH(CH$_2$)$_k$—CH$_2$—R$^9$,
OR$^{10}$ and —H,
—OR$^{10}$ and —(CH$_2$)$_k$—C≡C—U, or
R$^5$ and R$^6$ together are

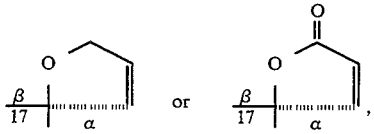

R$^7$ is hydrogen or C$_1$-C$_4$-acyl,
U is hydrogen, halogen, or alkyl, hydroxylalkyl, alkoxyalkyl, or acyloxyalkyl with respectively 1 to 4 carbon atoms in the alkyl and acyl portions thereof,
R$^8$ is hydrogen, hydroxy, or alkyl, O-alkyl or O-acyl, each with respectively 1 to 4 C atoms,
R$^9$ is hydrogen, hydroxy, cyano, or O-alkyl or O-acyl, each with respectively 1 to 4 carbon atoms,
R$^{10}$ is hydrogen, or alkyl or acyl, each with respectively 1 to 10 carbon atoms,
m is 0, 1, 2 or 3, and
k is 0, 1 or 2.

30. A process according to claim 29, further comprising removing said protective group from the 3-oxo group and functionalizing ring A to form a ring of the formula

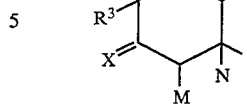

wherein
M and N together are a second bond or M is hydrogen and N is hydroxy,
X is oxygen, two hydrogen atoms, or N∼OH,
R$^3$ and D, being the same or different, are hydrogen, nitrile or C$_1$-C$_4$-alkyl, or together are a methylene or ethylene group,
E is hydrogen or C$_1$-C$_4$-alkyl,
D and E together can also be a second bond between carbon atoms 1 and 2 or together are a methylene group,
wherein X is not oxygen when N is hydroxy and M, R$^3$, D and E are all each hydrogen,

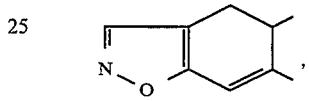

or

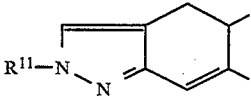

wherein
R$^{11}$ is as defined above.

31. A process according to claim 1, wherein protecting groups for protecting hydroxy, mercapto and keto groups are selected from methoxymethyl, ethoxymethyl, tetrahydropyranyl, ethylenedioxyketal, ethylenedithioketal and 2,2-dimethyltrimethylenedioxyketal.

32. A process according to claim 1, wherein the cyclization is conducted by reductive radical cyclization.

33. A process according to claim 1, wherein cyclization is conducted in liquid ammonia mixed with at least one organic solvent in the presence of an electropositive metal at a temperature of −100°— −30° C.

34. A process according to claim 1, wherein V' is

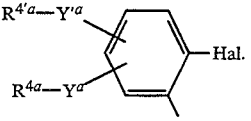

35. A process according to claim 34, wherein Hal is fluorine or chlorine.

* * * * *